US009717734B2

(12) United States Patent
Settineri

(10) Patent No.: US 9,717,734 B2
(45) Date of Patent: Aug. 1, 2017

(54) CHEWABLE LIPID SUPPLEMENTS CONTAINING CAFFEINE FOR INCREASING ALERTNESS, FOCUS AND ENERGY

(71) Applicant: Allergy Research Group, LLC, Alameda, CA (US)

(72) Inventor: Robert Settineri, Irvine, CA (US)

(73) Assignee: ALLERGY RESEARCH GROUP, LLC, Alameda, CA (US)

( * ) Notice: Subject to any disclaimer, the term of this patent is extended or adjusted under 35 U.S.C. 154(b) by 0 days.

(21) Appl. No.: 15/295,878

(22) Filed: Oct. 17, 2016

(65) Prior Publication Data

US 2017/0027947 A1 Feb. 2, 2017

Related U.S. Application Data

(63) Continuation-in-part of application No. 14/815,841, filed on Jul. 31, 2015, now Pat. No. 9,468,668, which
(Continued)

(51) Int. Cl.

| | |
|---|---|
| *A61K 31/522* | (2006.01) |
| *A61K 38/28* | (2006.01) |
| *A61K 31/122* | (2006.01) |
| *A61K 31/661* | (2006.01) |
| *A61K 31/70* | (2006.01) |
| *A61K 31/593* | (2006.01) |
| *A61K 31/375* | (2006.01) |
| *A61K 38/44* | (2006.01) |
| *A61K 31/385* | (2006.01) |
| *A61K 36/31* | (2006.01) |
| *A61K 31/66* | (2006.01) |
| *A61K 31/683* | (2006.01) |
| *A61K 31/7028* | (2006.01) |
| *A61K 36/81* | (2006.01) |
| *A61K 36/23* | (2006.01) |
| *A61K 36/21* | (2006.01) |
| *A61K 36/88* | (2006.01) |
| *A61K 36/48* | (2006.01) |
| *A61K 31/05* | (2006.01) |
| *A61K 36/45* | (2006.01) |
| *A61K 36/73* | (2006.01) |
| *A61K 36/736* | (2006.01) |
| *A61K 36/87* | (2006.01) |

(Continued)

(52) U.S. Cl.
CPC ............ *A61K 31/522* (2013.01); *A23D 9/013* (2013.01); *A23L 29/10* (2016.08); *A23L 29/244* (2016.08); *A23L 33/105* (2016.08); *A23L 33/115* (2016.08); *A23L 33/12* (2016.08); *A61K 9/0056* (2013.01); *A61K 31/05* (2013.01); *A61K 31/122* (2013.01); *A61K 31/16* (2013.01); *A61K 31/375* (2013.01); *A61K 31/385* (2013.01); *A61K 31/593* (2013.01); *A61K 31/66* (2013.01); *A61K 31/661* (2013.01); *A61K 31/683* (2013.01); *A61K 31/685* (2013.01); *A61K 31/7028* (2013.01); *A61K 31/716* (2013.01); *A61K 31/733* (2013.01); *A61K 33/22* (2013.01); *A61K 36/21* (2013.01); *A61K 36/23* (2013.01); *A61K 36/31* (2013.01); *A61K 36/45* (2013.01); *A61K 36/48* (2013.01); *A61K 36/73* (2013.01); *A61K 36/736* (2013.01); *A61K 36/81* (2013.01); *A61K 36/87* (2013.01); *A61K 36/88* (2013.01); *A61K 38/28* (2013.01); *A61K 38/44* (2013.01); *A61K 38/446* (2013.01); *A61K 45/06* (2013.01); *A61K 47/02* (2013.01); *A61K 47/10* (2013.01); *A61K 47/12* (2013.01); *A61K 47/46* (2013.01); *C12Y 111/01006* (2013.01); *C12Y 115/01001* (2013.01); *A23V 2002/00* (2013.01)

(58) Field of Classification Search
CPC .............. A61K 2300/00; A61K 31/683; A61K 31/685; A61K 31/122; A61K 31/16; A61K 31/66; A61K 31/716; A61K 33/22; A61K 31/522; A61K 31/661; A61K 31/7028; A61K 31/733; A61K 47/02; A61K 47/10; A61K 47/12; A61K 47/46; A61K 9/0056
See application file for complete search history.

(56) References Cited

U.S. PATENT DOCUMENTS

| | | | |
|---|---|---|---|
| 4,320,050 | A | 3/1982 | Rebeller et al. |
| 4,812,314 | A | 3/1989 | Barenholz et al. |

(Continued)

FOREIGN PATENT DOCUMENTS

| | | |
|---|---|---|
| CN | 1954079 A | 4/2007 |
| CN | 101316521 A | 12/2008 |

(Continued)

OTHER PUBLICATIONS

Search Report and Written Opinion of International Application No. PCT/US2014/011156 mailed May 1, 2014.
(Continued)

*Primary Examiner* — Mark V Stevens
(74) *Attorney, Agent, or Firm* — Koppel, Patrick, Heybl & Philpott; Michael J. Ram

(57) ABSTRACT

Flavored chewable wafers containing caffeine suitable for increasing alertness and allow an individual to perform tasks in a more focused and energetic manner comprises, formulations of phospholipids, specifically identified concentrations of phosphatidylglycerol, phosphatidic acid, phosphatidylethanolamine, phosphatidylcholine, glycolipids and phosphatidylserine along with inulin and other desirable active ingredients.

10 Claims, 17 Drawing Sheets

Related U.S. Application Data is a continuation-in-part of application No. 14/152,938, filed on Jan. 10, 2014, now Pat. No. 9,095,507, which is a continuation-in-part of application No. 13/208,255, filed on Aug. 11, 2011, now Pat. No. 8,877,239.

(60) Provisional application No. 61/750,991, filed on Jan. 10, 2013.

(51) Int. Cl.

| | | |
|---|---|---|
| *A23D 9/013* | (2006.01) | |
| *A61K 45/06* | (2006.01) | |
| *A61K 9/00* | (2006.01) | |
| *A61K 31/16* | (2006.01) | |
| *A61K 31/685* | (2006.01) | |
| *A61K 31/716* | (2006.01) | |
| *A61K 33/22* | (2006.01) | |
| *A23L 29/10* | (2016.01) | |
| *A23L 29/244* | (2016.01) | |
| *A23L 33/105* | (2016.01) | |
| *A23L 33/115* | (2016.01) | |
| *A23L 33/12* | (2016.01) | |
| *A61K 31/733* | (2006.01) | |
| *A61K 47/02* | (2006.01) | |
| *A61K 47/10* | (2017.01) | |
| *A61K 47/12* | (2006.01) | |
| *A61K 47/46* | (2006.01) | |

(56) References Cited

U.S. PATENT DOCUMENTS

| | | | |
|---|---|---|---|
| 4,851,339 A | 7/1989 | Hills | |
| 5,539,133 A | 7/1996 | Kohn et al. | |
| 5,541,056 A | 7/1996 | Huntley et al. | |
| 5,709,855 A | 1/1998 | Bockow | |
| 6,075,183 A | 6/2000 | Knutzon et al. | |
| 6,217,926 B1 | 4/2001 | Merkle et al. | |
| 6,348,213 B1 | 2/2002 | Barenholz et al. | |
| 6,403,345 B1 | 6/2002 | Kiy et al. | |
| 6,495,532 B1 | 12/2002 | Bathurst et al. | |
| 6,503,700 B1 | 1/2003 | Leung | |
| 6,579,714 B1 | 6/2003 | Hirabayashi et al. | |
| 6,797,835 B2* | 9/2004 | Fussbroich | A23J 7/00 424/489 |
| 6,974,593 B2 | 12/2005 | Henriksen et al. | |
| 7,439,267 B2 | 10/2008 | Granata et al. | |
| 7,476,522 B2 | 1/2009 | Putten et al. | |
| 9,095,507 B2 | 8/2015 | Settineri | |
| 2002/0119928 A1 | 8/2002 | McAnalley | |
| 2004/0001874 A1 | 1/2004 | Davidson et al. | |
| 2004/0237663 A1* | 12/2004 | Farber | A23G 3/0021 73/861.08 |
| 2005/0008690 A1 | 1/2005 | Miller | |
| 2008/0305096 A1 | 12/2008 | Verdegem | |
| 2008/0318909 A1 | 12/2008 | Sparagna et al. | |
| 2009/0004334 A1 | 1/2009 | Nair | |
| 2009/0274660 A1* | 11/2009 | Girsh | A61K 9/0095 424/93.3 |
| 2010/0166838 A1 | 7/2010 | Bollag et al. | |
| 2012/0040014 A1 | 2/2012 | Settineri et al. | |
| 2012/0121520 A1 | 5/2012 | Barron | |

FOREIGN PATENT DOCUMENTS

| | | |
|---|---|---|
| EP | 1181870 | 2/2002 |
| WO | WO88/06441 | 9/1988 |
| WO | WO03/088761 | 10/2003 |
| WO | WO03/105609 | 12/2003 |
| WO | WO2007/059762 | 5/2007 |
| WO | WO2012/021172 | 2/2012 |

OTHER PUBLICATIONS

Office Action P. R. China Patent Application 201180039539.2 dated Jan. 21, 2014.
Written Opinion and Search Report of International Application No. PCT/US2011/001421 mailed Oct. 7, 2011.
Andersson L, et al, Hydrolysis of galactolipids by human pancreatic lipolytic enzymes and duodenal contents, Jun. 1995, vol. 36, Journal of Lipid Research, p. 1392-1400.
Keller, J, et al. Phospholipid changes and lipid oxidation during cooking and frozen storage of raw ground beef, 1973, vol. 38, Journal of Food Science, p. 1200-1204.
Cattleman's Beef Board, The Chemistry of Beef: Executive Summary, May 2007, Item #12814, pp. 1-16.
Lobo et al. (Effects of dietary lipid composition and inulin-type fructans on mineral bioavailability in growing rats, Feb. 2009, Nutrition, vol. 25, pp. 216-225).
European Search Report from Corresponding EP Application No. 14726311.5-1456, dated Nov. 24, 2014.
Nicolson, et al., "Lipid Replacement and Antioxidant Nutritional Therapy for Restoring Mitochondrial Function and Reducing Fatigue in Chronic Fatigue Syndrome and other Fatiguing Illnesses", Journal of Chronic Fatigue Syndrome, vol. 13, No. 1, Sep. 5, 2006, pp. 57-68, XP055151975.
Nicolson, et al., "Reversing Mitochondrial Dysfunction, Fatigue and the Adverse Effects of Chemotherapy of Metastatic Disease by Molecular Replacement Therapy", Clinical & Experimental Metastasis; Official Journal of Themetastasis Research Society, Kluwer Academic Publishers, DC., vol. 25, No. 2, Dec. 5, 2007, pp. 161-169, XP019571219.
Ellithorpe, et al., "Pilot Study: Reduction of Fatigue by Use of a Dietary Supplement Containing Glycophospholipids", The Journal of the American Nutraceutical Association, vol. 6, No. 1, Jan. 1, 2003, pp. 23-28, XP055151750.
NT Factor: "Propax—NT Factor—Nutrition Supplements", Jan. 12, 2010, XP055151759, retrieved from the internet: url:http://www.propax.com/propax-with-nt-factor (retrieved Nov. 7, 2014, the whole document).

* cited by examiner

| HUMAN ORGAN | PC | PG & OTHERS | PE | PS |
|---|---|---|---|---|
| BRAIN - GREY | 39 | 8 | 40 | 13 |
| BRAIN - WHITE | 31 | 37 | 16 | 16 |
| HEART | 40 | 31 | 26 | 3 |
| LUNGS | 53 | 20 | 19 | 8 |
| LIVER | 44 | 25 | 28 | 3 |
| KIDNEYS | 33 | 42 | 24 | 1 |
| SKELETAL MUSCLE | 48 | 23 | 26 | 3 |
| PLASMA | 70 | 27 | 3 | - |
| PLATELETS | 40 | 23 | 28 | 9 |

*PERCENT OF TOTAL PHOSPHOLIPIDS

THE Y-AXIS IS AVERAGE WEIGHT LOST (LB) FOR THE ENTIRE GROUP

THE Y-AXIS IS AVERAGE WEIGHT LOST (LB) FOR THE RESPONDER GROUP

THE Y-AXIS IS AVERAGE HIP MEASURE LOSS IN INCHES FOR THE ENTIRE GROUP

THE Y-AXIS IS AVERAGE HIP MEASURE LOSS IN INCHES FOR THE RESPONDER GROUP

THE Y-AXIS IS AVERAGE WASTE MEASURE LOSS IN INCHES FOR THE ENTIRE GROUP

THE Y-AXIS IS AVERAGE WASTE MEASURE LOSS IN INCHES FOR THE RESPONDER GROUP

THE Y-AXIS IS AVERAGE BODY MASS INDEX CHANGE FOR THE ENTIRE GROUP

THE Y-AXIS IS AVERAGE BODY MASS INDEX CHANGE FOR THE RESPONDER GROUP

THE Y-AXIS IS AVERAGE BASAL METABOLIC RATE CHANGE FOR THE ENTIRE GROUP

THE Y-AXIS IS AVERAGE BASAL METABOLIC RATE CHANGE FOR THE RESPONDER GROUP

THE Y-AXIS IS AVERAGE HUNGER INDEX CHANGE FOR THE ENTIRE GROUP

CHEWABLE LIPID SUPPLEMENTS CONTAINING CAFFEINE FOR INCREASING ALERTNESS, FOCUS AND ENERGY

This application is a continuation-in-part and claims benefit of U.S. patent application Ser. No. 14/815,841 filed Jul. 31, 2015, now U.S. Pat. No. 9,468,668, issued Oct. 18, 2016, which is a CIP of U.S. patent application Ser. No. 14/152,938 filed Jan. 10, 2014, now U.S. Pat. No. 9,095,507 issued Aug. 4, 2015, which is a CIP of Ser. No. 13/208,255 filed Aug. 11, 2011, Now U.S. Pat. No. 8,877,239, all incorporated herein in their entirety by reference hereto, and claims benefit of Provisional Application Ser. No. 61/750,991 filed Jan. 10, 2013.

Chewable wafers for delivery of enriched nutritional supplements are described that include components necessary to maintain or restore cell and mitochondrial health and provide enhanced alertness due to the presence of caffeine, the combination providing a synergistic effect with extended efficacy significantly in excess of that obtained from prior art composition including equivalent concentrations of caffeine. While membrane-essential lipid molecules and chemical precursors for those molecules are provided in the form of supplements suitable for Lipid Replacement Therapy as disclosed in applicants above referenced parent applications, it was highly unexpected that caffeine delivered in combination with those same lipid molecules and chemical precursors would significantly increase the longevity of the effects of caffeine on the individuals consuming the compositions disclosed herein. Liquid Placement Therapy is the use of functional supplements containing cell membrane phospholipids and antioxidants to replace damaged, usually oxidized. Membrane glycophospholipids that accumulate during aging and to address various clinical conditions in order to restore cellular function (Nicholson, G. L. et al, "Lipid Replacement Therapy: A Natural Medicine Approach to Replacing Damages Lipids in Cellular Membranes and Organelles and Restoring Function", *Biochim. Biophys Acta*, 1838(6), June 2014, pp 1657-79). Processes and formulations set forth herein are designed to add to and supplement lipids in cells within the mammalian body including, but not limited to, phosphatidylglycerol (PG), phosphatidylcholine (PC), phosphatidylethanolamine (PE), phosphatidylserine (PS), phosphatidic acid (PA) and related phospho- and glyco-phospholipids containing linoleic acid (LA), other healthy fatty acids, and phospholipid (PL) precursors. In addition, by controlling or modifying growing conditions of lipid source plants or microbes (lipid source materials), selecting specific species that produce the desired lipids, the purification and extraction of enriched compounds from the lipid source materials and the addition of combinations of pre-existing lipid products with other ingredients unique compositions are created. These compositions can then be utilized in the preparation of various chewable formulations specifically designed for use as nutritional treatments to address various health needs and medical and organ-specific deficiencies. Additional applications are as functional foods, medical foods, general health support, increased sports performance, improved quality of life, increased cognitive function, such as mental focus, mental clarity and concentration, increased energy for enhanced physical activity, increased healthful nutrition for metabolic support, for veterinary supplements and to enhance fertility and skin health.

BACKGROUND

Mitochondria are intracellular organelles that convert food energy into cellular energy in the form of high-energy molecules for all cellular metabolic purposes. Mitochondria are encapsulated by two phospholipid (PL) membranes ("inner" and "outer" membranes) that are enriched in certain types of fatty acids, phospholipids and other lipids relative to most other cellular structures in the body. A major lipid component of mitochondrial membranes is cardiolipin (CL). CL can account for as much as 20% of the total lipids in mitochondria, and it is associated with several other PL and protein molecules that are critical in generating cellular energy. For example, CL is associated with cytochrome oxidase in the electron transport system located in the mitochondrial inner membrane. It is also associated with several other PL and protein molecules that are critical in generating cellular energy. CL damage is associated with many pathologies including oxidative stress (Iwase H. T. et al., Biochem. Biophys. Res. Comm. 222(1), 83-89, 1996) and aging (Paradies G. F. M. et al., FEBS Lett. 406(1-2), 136-138, 1997). In Barth's syndrome, remodeling of cardiolipin has been suggested as the cause of the often fatal pathology (Paradies G. F. M. et al., FEBS Lett. 406(1-2), 136-138, 1997; Valianpour, F. et al., Journal of Lipid Res. 44, 560-566, 2003).

Electron transport is initiated when reducing equivalents (electrons) enter the system from Complex I (NADH dehydrogenase) and Complex II (succinate dehydrogenase). The enzymatic components of these complexes face the mitochondrial matrix that is enclosed by the inner mitochondrial membrane. As used herein, the term "face" is used to indicate that chemical constituents of a molecule extend toward a particular constituent of another molecule. Electron transfer continues from Complex I and Complex II to CoQ, Complex III, cytochrome C, and Complex IV along with the generation of high energy molecules such as ATP. The final transfer is to molecular oxygen with the formation of water. The inner membrane separates the matrix from the mitochondrial cytosol which is contained between the mitochondrial inner and outer membranes. The outer membrane is permeable to molecules with a molecular weight of less than 10,000 Da, but the inner membrane is permeable only to small lipid-soluble molecules and substances transferred by transport mechanisms.

There are some tissue-to-tissue and organ-to-organ differences in mitochondria. For example, cardiac mitochondria are unique from the mitochondria of other types of cells in that they possess a Complex I-associated NADH dehydrogenase that faces the mitochondrial cytosol. As a result, cardiac mitochondria are more sensitive to certain types of drugs that can damage mitochondria. Because of the tissue-to-tissue differences in the phospholipid composition of cell and mitochondrial membranes, the administration of nutritional supplements with phospholipid compositions matching the targeted organ, as taught herein, is beneficial in maintaining normal phospholipid balance.

In general, mitochondria are very sensitive to oxidative damage. More specifically, mitochondrial genes and the mitochondrial membranes are sensitive to cellular reactive oxygen species/reactive nitrogen species (ROS/RNS) that cause oxidative damage. In the case of membrane phospholipids, oxidation modifies their structure. This can affect lipid fluidity, permeability and membrane function. (Conklin, K. A., Nicolson, G. L., "Molecular Replacement In Cancer Therapy: Reversing Cancer Metabolic And Mitochondrial Dysfunction, Fatigue, And The Adverse Effects Of Cancer Therapy" Curr. Therapy Rev. 4: pp 66-76, (2008)).

Over 50 million people in the US suffer from chronic degenerative disorders. While it is not clear that mitochondrial defects cause these problems, it is clear that mitochondrial dysfunction occurs in chronic degenerative diseases because mitochondrial function is measurably disturbed. Even autoimmune diseases such as multiple sclerosis, Sjögrens syndrome, lupus and rheumatoid arthritis appear to exhibit a mitochondrial dysfunction.

Mitochondrial dysfunction is associated with a wide range of solid cancers, is proposed to be central to the aging process, and is found to be a common factor in the toxicity of a variety of physical and chemical agents. Symptoms of mitochondrial pathologies include muscle weakness or exercise intolerance, heart failure or rhythm disturbances, dementia, movement disorders, stroke-like episodes, deafness, blindness, droopy eyelids, limited mobility of the eyes, vomiting, and seizures.

In addition, abnormal mitochondria are involved in various diseases, including inherited diseases involving mitochondrial DNA (mtDNA) changes. Mutation and inheritance can cause changes to mtDNA and nuclear DNA (nDNA).

Cardiolipin (CL) is a major component of mitochondrial lipids. Mammalian CL has four acyl chains, and consists of two molecules of phosphatidylglycerol (FIG. 1). Up to 90% of the fatty acids incorporated in mammalian cardiolipin consist of only linoleic acid (LA) which is an unsaturated omega-6 fatty acid with Holman nomenclature 18:2(n-6). LA is readily available in plant oils, especially in safflower, grapeseed and sunflower oils (FIG. 2).

The biosynthesis of CL occurs through several steps leading up to the combination of phosphatidylglycerol with cytidine diphosphate diacylglycerol (FIG. 3). A detailed description of the biosynthesis is set forth in U.S. Pat. No. 6,503,700 to Leung, which is incorporated herein by reference, a portion of which states:

"CDP-diacylglycerol (CDP-DAG) is an important branch point intermediate just downstream of phosphatidic acid (PA) in the pathways for biosynthesis of glycerophosphate-based phospholipids (Kent, Anal. Rev. Biocheni. 64: 315-343, 1995). In eukaryotic cells, PA, the precursor molecule for all glycerophospholipids, is converted either to CDP-DAG by CDP-DAG synthase (CDS) or to DAG by a phosphohydrolase. In mammalian cells, CDP-DAG is the precursor to phosphatidylinositol (PI), phosphatidylglycerol (PG), and cardiolipin (CL). Diacylglycerol is the precursor to triacylglycerol, phosphatidylethanolamine, and phosphatidylcholine in eukaryotic cells. Therefore, the partitioning of phosphatidic acid between CDP-diacylglycerol and diacylglycerol must be an important regulatory point in eukaryotic phospholipid metabolism (Shen et al., J. Biol. Chem. 271:789-795, 1996). In eukaryotic cells, CDP-diacylglycerol is required in the mitochondria for phosphatidylglycerol and cardiolipin synthesis and in the endoplasmic reticulum and possibly other organelles for the synthesis of phosphatidylinositol (PI). PI, in turn, is the precursor for the synthesis of a series of lipid second messengers, such as phosphatidylinositol-4,5-bisphosphate ($PIP_2$), DAG and inositol-1,4,5-trisphosphate ($IP_3$). Specifically, $PIP_2$ is the substrate for phospholipase C that is activated in response to a wide variety of extracellular stimuli, leading to the generation of two lipid second messengers; namely, DAG for the activation of protein kinase C and $IP_3$ for the release of $Ca^{++}$ from internal stores (Dowhan, Anal. Rev. Biochem. 66: 199-232, 1997)."

Remodeling of CL has been observed in the aging process, whereby the acyl chain LAs are replaced with the highly unsaturated fatty acids docosahexaenoic acid and arachidonic acid. In light thereof, as set forth herein, it is contemplated that lipid replacement therapy by providing PG with linoleic acid acyl groups can repair or reverse cardiolipin remodeling associated with aging and other pathologies.

*Spirulina* genus is a cyanobacteria group, commonly referred to as an alga. *Spirulina* as a food supplement has been common for possibly thousands of years. As a nutrient supplement, it is generally collected, dried or lyopholized, and powdered. Specific extraction methods for various components are discussed below. *Spirulina* naturally produces about 48% linoleic acid, and is also a significant source of PG (Bujard-E. U., Braco, U., Mauron, J., Mottu, F., Nabholz, A., Wuhrman, J. J., Clement, G., $3^{rd}$ International Congress of Food Science and Technology, Washington 1970).

*Spirulina* as a whole food has been shown to have several pharmacological effects. (Torres-Duran, P. V., Ferreira-Hermosilo, A. F., Juarez-Oropeza, M. A. Lipids in Health and Disease 6:33, 2007). Methods for extracting phytopigments from *Spirulina* have been described (U.S. Pat. No. 4,851,339, Hills). Pigments were extracted using non-polar organic solvents, the pigments were absorbed onto a starch gel, the solvent removed, and the pigments re-extracted in alcohol.

*Spirulina* species were combined with omega fatty acids to provide a composition for treating or preventing inflammation and/or pain by topical administration (U.S. Pat. No. 5,709,855, Bockow). An extraction process for obtaining a high proportion of long-chain polyunsaturated fatty acids having from 20 to 22 carbon atoms, where the raw material is of plant origin, alginate, or carrageenan residues is disclosed in U.S. Pat. No. 5,539,133, Kohn, et al.)

Calcium salts were used to make phycocyanine water soluble as an extraction method, particularly in *Spirulina* species (U.S. Pat. No. 4,320,050, Rebeller, et al.). The pigment was extracted with an aqueous solution containing calcium at 0.02 to 0.2 grams per liter, at a temperature from 15 to 45° C. for 15 minutes to 1 hour. The process required two repetitions. A further organic extraction was required to obtain other phytopigments such as carotenoids and xanthophylls.

Microalgae, for instance, *Spirulina* species is also another source of PLs. Environmental factors affect the fatty acid composition of *Spirulina* (Funteu, F. et al., Plant Phys. and Bioch. 35(1), 63-71, 1997) and can be used to manipulate the yields of targeted fatty acids such as PG. In particular, alteration of the growth media with phosphate and manganese salts can affect PG yields. Further, different species contain different ratios of fatty acids, and high-yield species can be identified (Muhling, M. et al., Journal of Applied Phycology, vol 17:22, 137-146, 2005).

Some sources of PL contain toxins that can contaminate lipid extractions. For example, many cyanobacteria species can produce toxins as a natural defense mechanism. The cultures can also be contaminated with other species that produce microcystins which exhibit neurotoxicity, hepatotoxicity, dermatotoxicity and cytotoxicity). Microcystins are cyclic heptapeptides with variations in amino acids at seven positions. Species that are toxic that can contaminate cultured cyanobacteria include *Microcystis, Anabaena*, and *Aphanizomenom* genuses.

Biological concentrates or extracts that are claimed to improve mitochondrial function include marine oils from sharks, codfish, salmon, and other species; various vegetable oils; and lecithin. Fish oil extracts include desirable components such as omega-3 fatty acids. A fish oil supplement called Omacor® or Lovaza® contains 90% omega-3 fatty acids and is a pure, clinically proven and FDA-approved prescription drug (U.S. Pat. No. 7,439,267, Granata, et al.)

Safflower, sunflower, grape seed, and olive oil and others are claimed to have high linoleic acid contents that promote cardiac health and lower cholesterol levels. Linoleic acid and related cardiolipin precursors are described in US published patent application 2008/0318909 for treating cardiac related symptoms and diseases. U.S. Pat. No. 6,348,213, Barenholz, et al., describes directly injecting PC intravenously to reverse age-related changes in lipid composition of heart muscle cells.

Lecithin is an oil or powder extract of soy beans or egg yolks. Lecithin is sometimes used as a synonym for its major constituent phosphatidylcholine (PC). Other components of lecithin include the phospholipids phosphatidylinositol (PI), phosphatidylethanolamine (PE), phosphatidylglycerol (PG), phosphatidylserine (PS), and phosphatidic acid (PA). In addition, glycophospholipids are present as galactolipids, with one (monogalctosyl-) or two (digalactosyl-) diacylglycerol. Lecithin is comprised largely of PC. It has been known for over one hundred years and there are numerous patents regarding processing and modification of lecithin. As discussed below, while the compounds disclosed herein use a lecithin base they are subjected to a unique fractionation and recombination procedure to enrich specific and nonspecific lipid components and to generate new compositions of matter tailored to address specific health requirements of the individual being treated.

A prior known composition, marketed as NT Factor, and referred to herein as NT1, as set forth in Table 1, has previously been shown to improve mitochondrial health. The prior NT Factor has been available commercially with a proprietary blend of ingredients added as nutritional supplements including, but not limited to, magnesium oxide (6 mg), magnesium glycinate, (0.03 mg) chromium polynicotinate, (1.8 mg), potassium citrate (5 mg), alpha lipoic acid (10 mg), *Bifidobacterium bifidum* (5 mg), blackstrap molasses (3 mg), boron as calcium borogluconate, (0.03 mg), bromelain from pineapple, (2400 gelatin digestive units per gram, 100 mg), beet root fiber (5 mg), fructo-oligosaccharides from beet or cane sugar (250 mg), *Lactobacillus acidophilus* (3.57 mg of microencapsulated, providing 250 million active organisms), L-Arginine, as L-Arginine HCl (13 mg), odor modified garlic from *Allium sativa* bulb, minimum of 10,000 ppm allicin potential, 10 mg, PABA, para-aminobenzoic acid (50 mg), pantethine, (a coenzyme A precursor) (50 mg), rice bran extract (250 mg), *Spirulina, Arthrospira platensis*, microalgae (10 mg), sulfur, from OptiMSM (28.85 mg) or a lesser amount (11.15 mg) added to augment sulfate when magnesium sulfate is replaced with magnesium oxide, taurine (13 mg) and coenzyme Q10.

TABLE 1

| NT FACTOR (NT1) (Prior Art Formulation) | |
|---|---|
| Vitamin E (as d-alpha tocopherol succinate) | 20 IU |
| Calcium (as calcium carbonate, calcium pyruvate, d-calcium phosphate) | 160 mg |
| Phosphorus (as di-calcium phosphate) | 50 mg |
| Magnesium (as magnesium oxide) | 50 mg |
| Alpha-ketoglutaric Acid | 120 mg |
| L-carnitine-L-tartrate | 90 mg |
| L-tyrosine | 60 mg |

TABLE 1-continued

| NT FACTOR (NT1) (Prior Art Formulation) | |
|---|---|
| Pantethine (as coenzyme A precursor) | 50 mg |
| Sulfur | 11.15 mg |
| NT Factor ®* (phosphoglycolipids from soy) | 1350 mg |

*NT1 contains a proprietary composition designated NT Factor ® (a registered trade mark of Nutritional Therapeutics, Inc. Islandia, NY) which comprises approximately 93% PC and lyso-PC of which around 24% is18:2 linoleic acid U.S. Pat. No. 4,812,314, Barenholz et al., describes the use of egg PC delivered parentally to produce a change in the lipid composition of heart muscles as indicated by a drop in serum CPK level, an increase in longevity and an improved fertility.

Lipid replacement therapy, also referred to as molecular replacement therapy, using NT1 has been shown to be an effective nutritional support for various health deficiencies. One example is in the use for cancer patients undergoing chemotherapy. A review of research shows that NT1, combined with antioxidants and other nutrients, repairs damage caused by oxidative stress. By replacing damaged lipid molecules in cell membranes and membranes of mitochondria, the energy generating component in cells is improved, and both acute and chronic adverse effects of chemotherapy have been reduced in a majority of chemotherapy patients who followed a regimen of NT Factor plus antioxidants and other nutrients. (Nicolson G L, Conklin K A, Reversing mitochondrial dysfunction, fatigue and the adverse effects of chemotherapy of metastatic disease by molecular replacement therapy, Clinical & Experimental Metastasis 2007 Dec. 5).

Phospholipids have been extracted from marine oils (US Published Application 20090028989). The lipid fraction was dissolved in a non-polar solvent, where phospholipids formed large micelles that were separated from other lipids and non-polar toxins by microfiltration. An aqueous multi-step process was also used to extract phospholipids from egg yolks (U.S. Pat. No. 6,217,926, Merkle et al.).

While lecithin and lecithin fractions or extracts are beneficial for lipid replacement therapy for somatic cells, they are not formulated to contain the specific ratios of phospholipid species that are found in mitochondrial membranes in different organs. However, because of their phylogenetic similarities to mitochondria, many bacteria species such as *Spirulina* contain appreciable concentrations of PG as found in heart tissues. Growth factors, conditions and selection of species each influence the distribution of fatty acids in the culture. U.S. Pat. No. 7,476,522, Putten, et al., describes enrichment of gamma-linolenic acids from a ciliate culture by adding suitable precursors to the culture medium. U.S. Pat. No. 6,579,714, Hirabayashi, et al., describes a culture apparatus for algae that produce high levels of highly unsaturated fatty acids, photosynthetic pigments, and/or polysaccharides. Growing conditions for *Colpidium* genus, a protozoan, were optimized to maximize gamma-linolenic acid yields (U.S. Pat. No. 6,403,345, Kiy, et al.) *Spirulina* (*S. platensis*) can be made to produce a GLA content of the extractable oil between 12 and 26% (Mahajan G., Kamat, M., 1995; Appl. Microbiol. Biotechnol., 43, 466-9; Nichols, B. W., Wood, B. J. B., 1968; Lipids, 3, 46-50).

Different methods for enhancing the growth of cultured microorganisms appear in the patent literature. As an example, a method of increasing growth in cultured microorganisms by controlling turbulence has been disclosed (U.S. Pat. No. 5,541,056, Huntley, et al.)

There are several transgenic methods of increasing protein and fatty acid expression in plants (e.g., U.S. Pat. No. 6,075,183, Knutzon, et al.; U.S. Pat. No. 6,503,700, Leung). US Published Application 2010/0166838 describes the use of PG, which is a precursor for cardiolipin, as improving mitochondrial function and energy production. PG has also been mentioned as a factor for increasing the solubility of water-insoluble drugs (U.S. Pat. No. 6,974,593, Dec. 13, 2005, Henriksen et al.) Lysophosphatidic acids are used in compositions that inhibit apoptosis in (U.S. Pat. No. 6,495, 532, Bathurst et al.)

The effect of caffeine consumption on the human body is well understood. Caffeine, whether consumed in beverages such as coffee, tea, energy drinks or as in a pill form such as NoDoz®, is used by so many people to keep them feeling alert and awake. Caffeine works by counteracting the effect countering a substance in your brain known as adenosine. Adenosine builds in the brain during the day as a result of normal brain activity. Receptors in the brain sense the amount of the adenosine being built up, with increased levels signaling the brain that the end of the day is approaching, the individual feels tired, and should sleep, which results in the decrease in adenosine. Caffeine has a chemical structure similar to adenosine molecules so that it actually binds to the receptors, but does not activate the receptors, Because the receptors are blocked by the caffeine molecules, the brain thinks there is less adenosine than is actually present there, the individual remains alert and does not feel tired or sleepy and the dopamine and glutamate molecules, the brain's natural stimulants, are not inhibited.

The strength of these effects can vary from person to person and it depends on various different factors, and particularly an individual's level of tolerance to caffeine. In particular the body can build up a tolerance to and continued use of caffeine or the number and frequencies of caffeine intake will result in a decrease in the effect of caffeine consumption. For example, a first cup of coffee, will probably have a strongly. However, if an individual is a chronic coffee drinker consuming multiple cups a day (i.e., 3-5) for many years, the expected effects of caffeine ingestion may not be felt at all. This tolerance can be reversed by abstention for a period of time to allow the brain to return to normal chemical balance. However, as with the withdrawal of many drugs ceasing caffeine consumption can also result in withdrawal symptoms which can be quite severe.

SUMMARY

Disclosed herein are chewable wafers that can include therein various nutritional materials and phospholipids described herein. Particularly included herein by reference are those various materials and compositions set forth in U.S. patent application Ser. No. 13/208,255 incorporated herein in its entirety by reference in this application. This includes the use of animal tissues, plant species, fungi, yeast, protozoa and bacteria as a source of various phospholipids including, but not limited to PG. Bacteria can contain from trace amounts of PG to up to 70% of the phospholipids. In plants PG forms 20 to 30% of the phospholipids, found mainly in chloroplasts. In addition to identifying biological sources producing significant amounts of PG, the linoleic acid form of PG is a preferred form of PG for use in maintaining human mitochondrial health. Other organ specific phospholipids such as 18:1 PS are also suitable, for example, to improve mental functions.

Lipid containing compounds referred to as NT Factor have been known and used in the past as dietary supplements (see Table 1). The wafer compositions set forth herein contemplate inclusion therein of the above described NT Factor which has never been available in a chewable wafer form. Inclusion of New Lipid Formulation A is also contemplated. New Lipid Formulation A is specifically enriched in phosphatidic acid. New Lipid Formulation C is specifically enriched in phosphatidylcholine. New Lipid Formulation E is specifically enriched in phosphatidylethanolamine. New Lipid Formulation G is specifically enriched in phosphatidylglycerol. New Lipid Formulation I is specifically enriched in phosphatidylinositol. New Lipid Formulation S is specifically enriched in phosphatidylserine. These enriched formulae are then used for targeted delivery to mitochondrial and cellular membranes for Lipid Replacement Therapy—a nutritional procedure that results in natural replacement of damaged cellular lipids with the correct lipids or a correct balance of lipids for healthy and normal function as well as lipids which can have tailored acyl chains per length and unsaturations. While soy is a common plant source of lecithin, lecithin can be extracted from various different plant sources, for example safflower, sunflower or other oil seeds. Lecithin from different sources, or from the same source grown in different years, can have different concentrations of lipids. Blends of lecithin from different sources can be used to prepare a "standardized" or reproducible composition or to produce a composition enriched in specific lipids.

A new class of compounds or compositions, referred to as Cyanithins, are also disclosed in U.S. patent application Ser. No. 13/208,255 and are incorporated herein by reference. The Cyanithins comprise microbial or plant extracts with phospholipids analogous to those found in lecithin fractions from plant extracts. Cyanithin A is specifically enriched in phosphatidic acid. Cyanithin C is specifically enriched in phosphatidylcholine. Cyanithin E is specifically enriched in phosphatidylethanolamine. Cyanithin G is specifically enriched in phosphatidylglycerol. Cyanithin S is specifically enriched in phosphatidylserine. The New Lipid Formulation and Cyanithins can be combined or fortified with specific nutrients to provide targeted health benefits for both general health and as well as to treat specific ailments involving mitochondrial damage and cell membrane damage. In addition, the lipid profile, particularly the fatty acid profile of specific or general phospholipid bases can be improved by adding triglycerides or other fatty acid sources that are rich in, or comprise a pure specific fatty acid or a combination of specific fatty acids. These new mixtures are hereinafter referred to as "Combinations".

Disclosed herein are chewable wafers that include caffeine and nutrient and probiotic compositions that increase mitochondrial function, as well as bioavailability of virtually all nutrients and, unexpectedly provide the known and desired effects of caffeine in an enhanced manner and also extend those effects over a period of time much greater than the time benefit experienced from the delivery of the same quantities of caffeine from prior art caffeine sources or supplements.

The various New Lipid Formulations and Cyanithins, which include inulin, as well as Combination formulas with lecithins and specific fatty acids provide cell and mitochondrial lipids that increase the transport of nutrients such as vitamins, antioxidants, glucose, and others. These lipids replace damaged or missing lipids in membrane structures and restore and revitalize the ability of cells and mitochondria to pass molecules of vital interest into and out of cellular and subcellular compartments. The Inulin appears to aid in this transport function.

Those New Lipid Formulation and Cyanithins, with inulin, as well as Combination formulas with lecithins and specific fatty acids also increase cellular energy required for cellular transport and other functions by repairing mitochondrial membranes and as a result increase the efficiency of electron transport to produce high energy molecules such as ATP and NADH.

In addition, the various New Lipid Formulations and Cyanithins, with inulin, as well as Combination formulas with lecithins and specific fatty acids can be fortified with various combinations of probiotics with or without inclusion of prebiotics such as fructo-oligosaccharides (FOS) and other nutrients that foster healthy bacteria in the digestive tract. Specifically targeted species of bacteria successfully facilitate the passage of nutrients and lipids from the digested matter in the digestive tract through the walls of the digestive system and into the circulatory system. The combination of increased bioavailability by increased absorption from the digestive system as well as increased nutrient absorption through individual cells and subcellular structures represents a novel and important advance in pharmaceutical and nutraceutical science.

Additional nutrients can be also be added. Nutritional supplements targeting cell membrane and mitochondrial health typically contain:
  a) coenzyme Q10 (hereafter referred to as CoQ10);
  b) L-carnitine in various forms such as acetyl L-carnitine, acetyl L-carnitine arginate dihydrochloride (patented), carnosine, L-carnitine fumarate, and L-carnitine tartrate among others (hereafter referred to as L-carnitine);
  c) alpha-lipoic acid in two forms, and
  d) phosphatidylcholine (hereafter referred to as PC).
In addition, a variety of antioxidant vitamins such as A, B, D, E and K are often included.

These new nutrient supplement compositions for stimulating and maintaining mitochondrial and cell health comprise enriched concentrations of lipids for replacing aged, damaged or remodeled lipids in cell and mitochondrial membranes. Described herein are improved compositions comprising new and unique Lipid Formulations and Cyanithins and Combinations containing specially grown, purified and extracted concentrates of specific phospholipids and glycophospholipids and specific fatty acids from biological sources, such as *Spirulina* or other species, as well as Combinations from existing lecithins and specific fatty acid sources These new formulations, and the extraction, fractionation, combination and purification procedures to prepare them, are unique in both their compositions and the utility to address mitochondrial defects and deficiencies as well as other organ, disease or system-specific malfunctions.

Described herein are chewable wafers (also referred to as chewable tablets) and their method of manufacture as an improved method of delivering therapeutic lipid compositions in combination with caffeine. Currently available products comprise large pills, capsules and water dispersible powder. A major deficiency of these products is that consumers object to the size of the pills or capsules, the number of pills or capsules and the volume of water based solutions they have to consume on a daily basis to receive a proper therapeutic dosage. The compositions set forth herein provide a good tasting, chewable wafer caffeine/lipid delivery system more acceptable to consumers which has enhanced ability to provide metal alertness and reduce the urge to sleep while at the same time providing the desired effect for a time period unseen with prior art caffeine supplements of equivalent dosage.

The ability to provide a chewable wafer also provides the opportunity to readily produce numerous variations of the caffeine/lipid compositions with varying concentrations of the various ingredients as well as including different vitamins, minerals and other nutrients deemed beneficial to maintaining health and addressing various nutritional deficiencies. This now offers to medical and health care practitioners as well as the general consumer of over-the-counter products the ability to specifically target a particular area of nutritional support while at the same time extending the period of alertness and reducing the feeling of fatigue. While the description below details manufacture of a particular embodiment, based on the teachings herein one skilled in the art will readily recognize how to prepare various other therapeutic wafers. For example to support prostate health the base chewable wafer composition obtained as shown in FIG. 24 can be then be supplemented by addition of prostate supporting nutrients such as Lycopene, Saw Palmetto Pygeum and Stinging nettle. Alternatively, these materials can be added during the processing as shown in FIG. 24.

DESCRIPTION OF DRAWINGS

The following examples are illustrative of the various embodiments of the present invention, and should not be regarded as limiting. For the present invention to be easily understood and readily practiced, the invention will be described, for purposes of illustration and not limitation, in conjunction with the following figures wherein.

DETAILED DISCUSSION

The NT Factor listed in Table 1 is a commercially available composition described as follows:

"NT Factor is a mixture of cellular lipids that is rich in phospholipids and glycophospholipids, and in particular, polyunsaturated phosphatidylcholine and other membrane lipids. It also contains essential fatty acids and other lipids that are important in mitochondrial function and cellular membrane health and probiotic microorganisms to aid in intestinal uptake (Ellithorpe R R, Settineri R, Nicolson G L. Pilot Study: Reduction of fatigue by use of a dietary supplement containing glycophospholipids. JANA 2003).

NT Factor® is a nutrient complex extracted and prepared using proprietary processes. It is composed only of food and food components listed as:

Phosphoglycolipids (also referred to as glycophospholipids)—includes polyunsaturated phosphatidylcholine, glycolipids and other polyunsaturated phosphatidyl nutrients.

Bifido and *Lactobacillus* Bacterium—freeze-dried and microencapsulated in a state of suspended animation with the potential to form healthy microflora colonies.

Growth Media—foods and bacteria growth factors to support microflora colonies including rice bran extract, arginine, beet root fiber, black strap molasses, glycine, para-amino benzoate, leek, pantethine (bifido growth factor), taurine, garlic, calcium borogluconate, potassium citrate, *spirulina*, bromelain, natural vitamin E, calcium ascorbate, alpha-lipoic acid, oligosaccharides, B-6, niacinamide, riboflavin, inositol, niacin, calcium pantothenate, thiamin, B-12, folic acid, chromium picolinate."

U.S. patent application Ser. No. 13/208,255, incorporated herein by reference, provides new and unique compositions which provide significant improvements over prior available lipid compositions such as NT Factor (NT1) for the maintenance of health, the improvement of physiological indicators (weight loss, body mass, metabolic rate, hunger, fatigue, cognitive function, energy, and others) and the treatment of acute and chronic heath and disease conditions. Also disclosed herein are methods of recovering lipids and new sources for lipid compositions to be used in lipid therapy.

Figure 1:
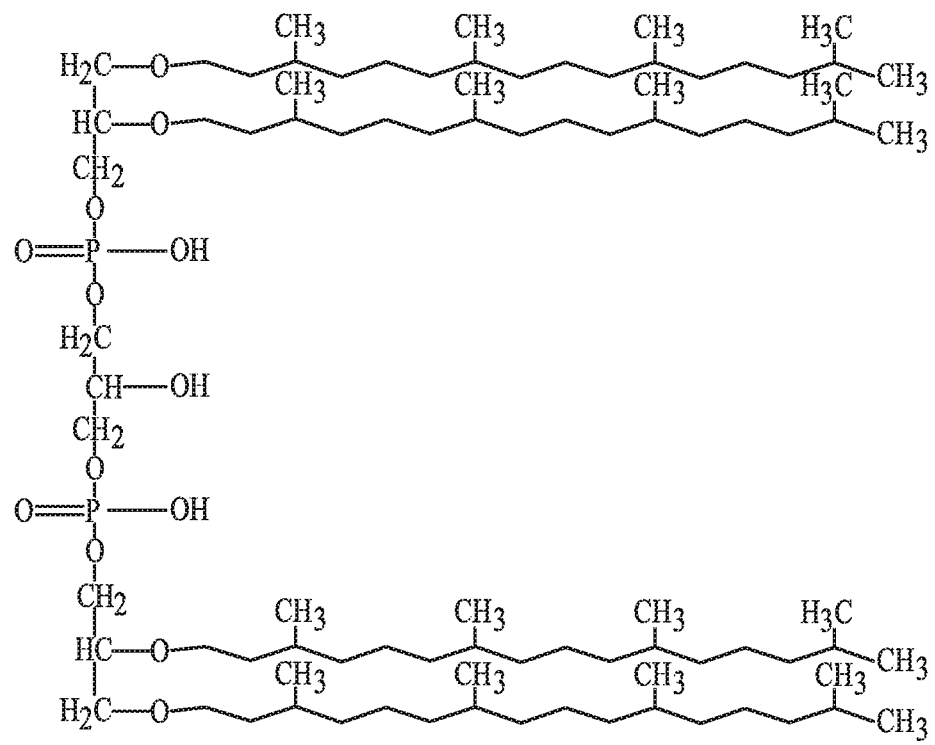
FIG. 1 is a representation of the cardiolipin molecule.
Figure 2:
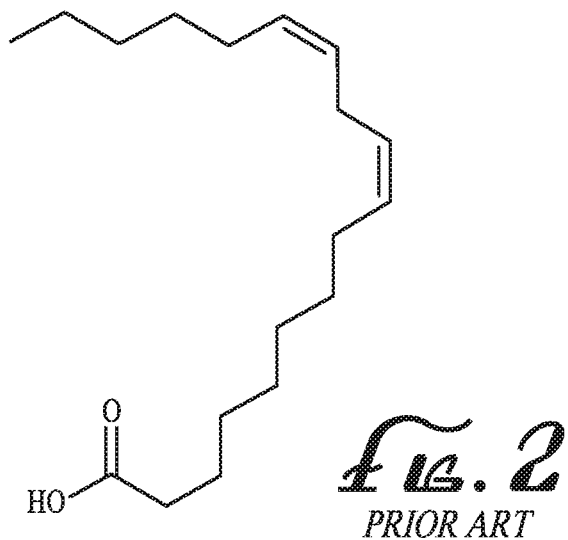
FIG. 2 is a representation of the linoleic acid molecule.
Figure 3:
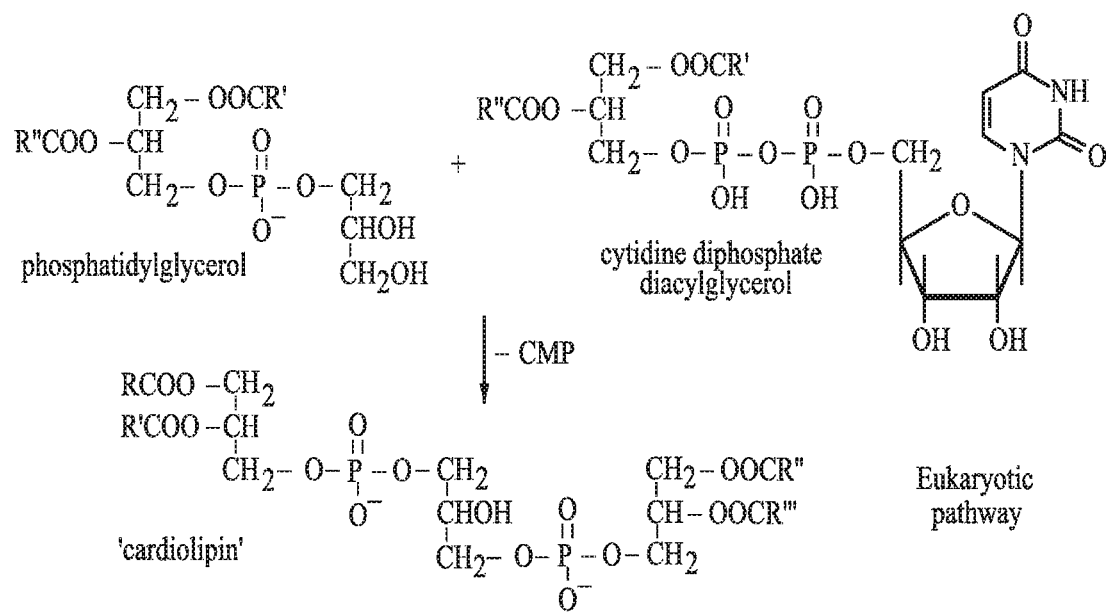
FIG. 3 is a formula showing the biosynthesis of cardiolipin in eukaryotes.
Figure 4:
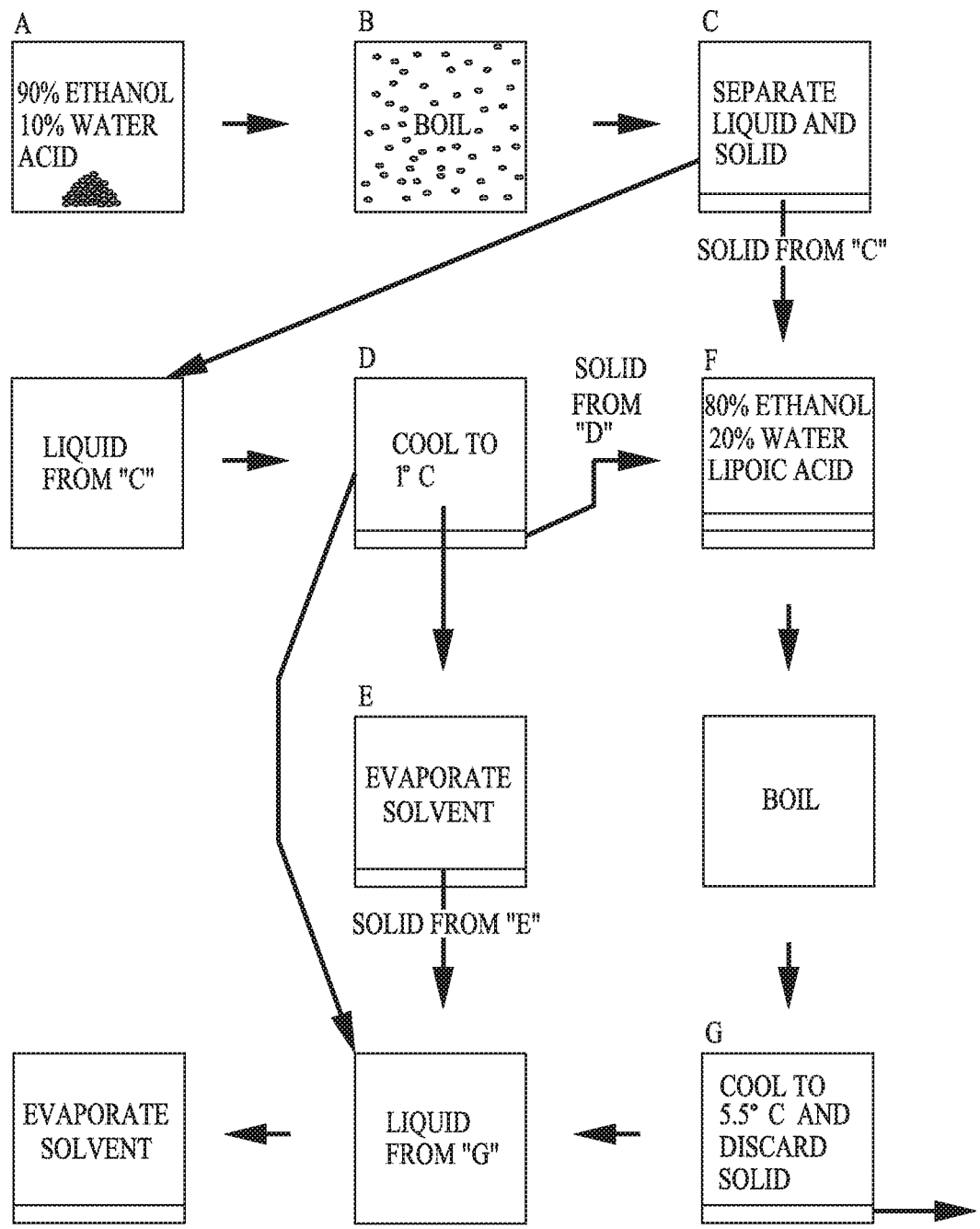
FIG. 4 is a schematic diagram showing the novel extraction method for preparing new Lipid Formulation A, C, E, G and S.

Shown schematically in FIG. 4 is a method for extraction and/or fractionation of lecithin mixtures to provide an enriched source of lipids and phospholipids for cellular and mitochondrial lipid replacement therapy. Lecithin is an enriched source of PC, PI, PE, PS and PA, but does not contain significant amounts of PG. This deficiency is addressed by the compositions and procedures set forth herein.

New Lipid Formulations disclosed therein are designed to be similar to mitochondrial and cell membrane lipid mixtures. The New Lipid Formulations maximize the lipid replacement process and maximize cellular health and membrane function.

Figure 5:
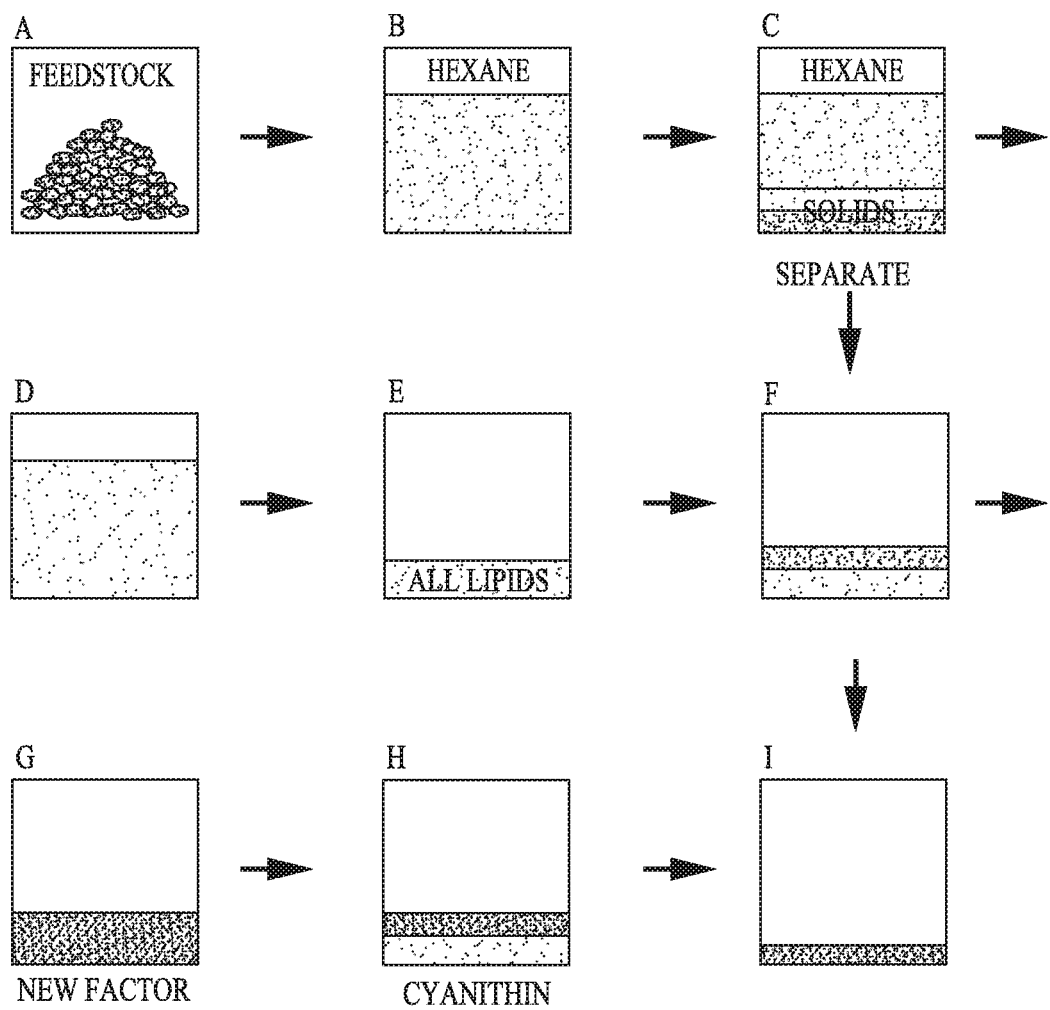
FIG. 5 is a schematic of the purification method to obtain the Cyanithins.

Also disclosed, and shown schematically in FIG. 5, is a method for extraction/fractionation and purification of biologic matter to enrich specific phospholipid and glycophospholipid species and antioxidant species to produce new compositions referred to herein as Cyanithins.

A specific embodiment comprises an extraction and purification process for *Spirulina* and other species including plant, animal, fungal, and single celled organisms and bacteria including algae. The extraction and purification processes remove toxic heavy metals that have oxidative properties, as well as environmental toxins such as PCBs, dioxins, organophosphates, microcystins, and others. In addition, the processes enrich the content of natural antioxidants such as tocopherol, and phytopigments which are naturally associated with photosynthetic organisms, such as chlorophyll as well as many others. The process specifically enriches the PG (or other target PL) concentration containing the LA fraction of lipids and, for other purposes, stearic or oleic (18 carbon) and palmitic (16 carbon) fatty acids.

Improved absorption of nutrients and lipids at the cellular and subcellular level results from providing essential membrane component phospholipids. These components include specific lipids that replace or repair damaged membrane lipids and allow the increased passage of essential molecules into and out of cellular and subcellular compartments.

Additionally, described herein are prebiotic and probiotic materials as well as growth media which may be used in combination with essential lipids, antioxidants, vitamins, and other nutrients that promote the growth of bacteria in the digestive tract, specifically of the type that promote the enhanced absorption of lipids, nutrients, antioxidants and other desirable molecules into the circulatory system.

New Lipid Formulation A and Cyanithin A are enriched in phosphatidic acid and glycophospholipids. New Lipid Formulation C and Cyanithin C are enriched in phosphatidylcholine and glycophospholipids. New Lipid Formulation E and Cyanithin E are enriched in phosphatidylethanolamine and glycophospholipids. New Lipid Formulation G and Cyanithin G is enriched in phosphatidylglycerol and glycophospholipidsl. New Lipid Formulation I and Cyanithin I are enriched in phosphatidylinositol and glycophospholipids. New Lipid Formulation S and Cyanithin S are enriched in phosphatidylserine and glycophospholipids. These New Lipid Formulations and Cyanithins are produced by use of the processes set forth in FIGS. 4 and/or 5 to separate and concentrate desired lipids which can then be combined to provide new Compositions with specific desired lipid profiles.

A new process for enriching specific fatty acids of phospholipids is disclosed. In a first embodiment, the 18:2 linoleic acid content enrichment of phospholipids is set forth. In a typical procedure, a triglyceride mixture rich in linoleic acid is used to dissolve de-oiled lecithin at a ratio of approximately 6 parts lecithin to 4 parts triglycerides. High linoleic acid content oils can be obtained, for example, from oil seeds such as safflower, sunflower, and grape seeds. The combined lipid nutrient is referred to as Combination A.

The Combination A can be sprayed onto or otherwise combined with a carrier to provide a dry powder. Typically, a carrier such as maltodextrin is used. Tapioca dextrin and dessicants can also be added to improve the handling properties for different uses such as foods, beverages, cosmetics, topical skin health and wound healing, nutraceuticals, functional foods, medical foods, premixes, veterinarian uses, and pharmaceuticals. The powder produced typically contains up to about 88% of Combination A, but the loading factor may be varied to standardize chosen components such as linoleic acid or specific phospholipids.

A further embodiment is the enrichment of phosphatidylserine with oleic acid (18:1) by reconstituting dry powder containing PS with an oil that is rich in oleic acid such as canola oil, olive oil, pecan oil, high-oleic safflower oil, or high-oleic sunflower oil. This can facilitate the post-digestion and absorption kinetics of the reassembly of PS into a form that matches the form found in mammalian brain and other tissues.

A further embodiment is enrichment of specific phospholipids with palmitic acid (16:0). This can facilitate the post-digestion and absorption kinetics of a reassembly of PG into a form that matches the form found in mammalian lung fluid or other tissues.

A further embodiment is enrichment of specific phospholipids with α- or γ-linolenic acid. This may facilitate the post-digestion and absorption kinetics of a reassembly of phospholipids into a form that matches the form found in mammalian tissues.

A further embodiment is supplying improved feedstocks for enzymatic conversion to particular phospholipid species. For instance, for producing PS for human neural health, a feedstock lecithin from a high-oleic acid content oil is preferably used. While soy lecithin is typically used, canola lecithin will yield a higher quantity of PS with oleic acid acyl chains, which more closely mimics the PS found in mammalian brains. In another instance, the feedstock for mitochondrial-healthy lipids is preferably higher in linoleic acid such as is found in lecithins from safflower, sunflower, and grapeseed oils. Specifically, high-linoleic safflower, sunflower, and grapeseed lecithins are identified as treatments for general health as well as specific mitochondrial and cardiac health.

A further embodiment is an enriched New Lipid Formulation containing inulin powder. Specifically, edible oils with desired fatty acids are combined with inulin to produce a powder. This powder is preferentially loaded with from about 12.5% to about 50% of the oil and can be used in the manufacture of foods, beverages, nutraceuticals and pharmaceuticals.

The New Lipid Formulations, Cyanithins, and Combinations, alone or in combination, have a wide variety of uses including, but not limited to pharmaceuticals, medicinals, nutritional supplements, functional foods, medical foods, ointments, and solubilizing agents. The chewable wafers described herein provide a new and useful way for delivering any nutritional compositions and particularly the lipid compositions set forth herein.

In the past, oral delivery systems include tablets and capsules. The chewable wafer disclosed herein provide a new, convenient method for oral delivery of beneficial compositions.

Disclosed in U.S. patent application Ser. No. 13/208,255, incorporated herein by reference, is a unique fractionation method for lecithin or other lipid concentrates from plant sources and a unique extraction/fractionation and purification method for biological materials, such as *Spirulina* or other species, or combinations thereof, to produce compounds, compositions and formulations that are enriched with phospholipids, such as PG and other PLs, natural antioxidants, and other added pre- and probiotics and nutrient factors. As used herein the term "biological materials" is used to identify single or multicell organisms, such as bacterial and single-celled organisms such as bacteria and algae including, but not limited to, *Aquifex, Thermotoga, Bacteroides, Cyophaga, Planctomyces, Cyanobacteria, Proteobacteria, Spirochetes*, Gram positives, Green Filamentous bacteria, *Pydrodicticum*; Archea, including: *Thermoproteus, T. celer, Methanococcus, Methanobacterium, Methanoscarcina*, Halophiles; Eucaryota including: *Entamoebae*, Slime molds, Fungi, Ciliates, Flagellates, Trichomonads, Microsporidia, and Diplomonads. On the other hand "plant materials" is used to identify agricultural products used as a source, including prior plant sources listed in the literature (soy, etc.) as well as vascular plants including, but not limited to eudicots, monocots, basal angiosperms, gymnosperms, ferns and lycophytes; bryophytes including hornworts, mosses and liverworts; charophytes including harophyceae, colecochaetophyceae, zygnemophyceae, klebsormidiophyceae, chlorokybophyceae; chlorophytes including trebouxiophyceae, chlorophyceae, ulvophyceae, and prasinophyte grade; rhodophytes and glaucophytes. One embodiment consists of an enriched PL formula produced from plant lecithins. Other compositions are enriched in phosphatidic acid, phosphatidylcholine, phosphatidylethanolamine, phosphatidylglycerol, phosphatidylinositiol or phosphatidylserine. These enriched formulae provide the basis for targeted delivery to mitochondrial and cellular membranes in a process referred to as lipid replacement therapy, which is a nutritional procedure that replaces damaged cellular lipids with the correct lipids for healthy and normal function. In addition, the length of the acyl chains and the level of saturation in the compounds can be tailored to optimize the beneficial results obtained by delivery of these compositions.

The Cyanithin formulae are based on microbial extracts (with biological materials as the starting materials) which are analogous to lecithin fractions derived from plant materials. The New Lipid Formulation A, C, E, G, I and S and Cyanithins A, C, E, G, I and S can be combined or fortified with specific nutrients to provide targeted health benefits for both general health and specific ailments involving mitochondrial damage and cell membrane damage.

In addition, each Cyanithin formula can be enriched with particular fatty acids suited for an intended end purpose. For instance, Cyanithin S can be enriched with oleic acid for neural health. Cyanithin C and G can be enriched in linoleic acid for mitochondrial health. Cyanithin G can be enriched in palmitic acid for lung and skin health.

In addition, the feedstocks used to produce the different Cyanithins can be chosen to be enriched in a particular fatty acid to produce a higher yield of the phospholipid intended for a given purpose, for example to match the natural biological endpoint). For instance, the feedstock for PS can be rich in oleic acid. Current art uses soy phospholipids for feedstock; however, using canola or another high-oleic acid content feedstock will yield more "correct" 18:1 PS. In another instance, the feedstocks for treatment of mitochondrial and cardiac disease targeting healthy cardiolipin preferably have a high linoleic acid concentration.

Nutrient and probiotic compositions that increase mitochondrial function can also increase the bioavailability of virtually all nutrients through at least the three specific means listed below and the phospholipid formulations and Cyanithins can be improved by adding specific or general mixtures of fatty acids, or other specific or general lipids, producing new combinations referred to as Compositions.

First, the New Lipid Formulations A, C, E, G, I and S and the Cyanithins and Combinations provide cell and mitochondrial lipids that increase the transport of nutrients such as vitamins, antioxidants, glucose, and others. The lipids that are provided replace damaged or missing lipids in membrane structures and restore and revitalize the ability of cells and mitochondria to pass molecules of vital interest into and out of cellular and subcellular compartments.

Second, New Lipid Formulations A, C, E, G, I and S and the Cyanithins and Combinations increase cellular energy required for cellular transport and other functions by repairing mitochondrial membranes and thereby increase the efficiency of electron transport to produce high energy molecules, such as ATP and NADH.

Third, New Lipid Formulation A, C, E, G, I and S and the Cyanithins and Combinations can be fortified with probiotic and prebiotic nutrients that foster healthy bacteria in the digestive tract. Specifically targeted species of bacteria facilitate the passage of nutrients and lipids from the digested matter in the digestive tract successfully through the walls of the digestive system and into the circulatory system. The combination of increased bioavailability as a result of increased absorption from the digestive system as well as increased nutrient absorption through individual cells and subcellular structures represents a novel and important advance in pharmaceutical and nutraceutical science. These material can be incorporated within the chewable wafers described herein.

Evaluation of NT Factor (NT1)

NT Factor (NT1) has been tested to determine its effectiveness in reversing the myriad maladies associated with mitochondrial aging and lipid remodeling. Of particular relevance is the reversal of the negative side effects of chemotherapy. Chemotherapy causes excess cellular oxidative stress through the intentional production of reactive oxygen species (ROS) and reactive nitrogen species (RNS) that are targeted toward cancer cells. Additionally, many cancers cause an increase in reactive oxygen species (ROS) and reactive nitrogen species (RNS). Oxidative stress also causes undesirable side effects in normal cells and is indicated as a factor in natural or premature aging, chronic fatigue, and others. (Nicolson, G. L. Lipid replacement therapy: a nutraceutical approach for reducing cancer-associated fatigue and the adverse effects of cancer therapy while restoring mitochondrial function. Cancer Metastasis Rev. 29(3): 543-552 (2010); Nicolson, G. L. "Metabolic Syndrome And Mitochondrial Function: Molecular Replacement And Antioxidant Supplements To Prevent Membrane Oxidation And Restore Mitochondrial Function". *J. Cell. Biochem.* 100: 1352-1369 (2007); Nicolson, G. L. and Ellithorpe, R. "Lipid Replacement And Antioxidant Nutritional Therapy For Restoring Mitochondrial Function And Reducing Fatigue In Chronic Fatigue Syndrome And Other Fatiguing Illnesses". *J. Chronic Fatigue Syndr.,* 13(1): 57-68 (2006)).

The ability to reverse the side effects of chemotherapy provides an indication of possible success in addressing other problems associated with oxidative stress in humans and other species. Examples of diseases and syndromes where mitochondrial function is impaired are: neurodegenerative diseases (ALS, MS, Alzheimer's Disease, Parkinson's Disease, peripheral neuropathies, etc.) and other neurological disorders, PAD, stroke, chronic pain, neurobehavioral diseases (ASD, ADD, ADHD, Asperger's Syndrome, etc.), Metabolic Disease and Diabetes, Coronary Heart Disease-ASHD, Vascular Diseases, Autoimmune Diseases, Rheumatic Diseases such as RA, osteoarthritis, Lupus, Scleroderma, Polymyositis, Bursitis, Fatiguing Illnesses such as CFS, Fibromyalgia Syndrome, Gulf War Illness, Asthma and other respiratory disorders, GI disorders such as IBS, IC, CD, fertility, pregnancy and neonatology, hearing loss, chronic infections (such as hepatitis, prostatitis, urinary and bladder infections, *mycoplasma, chlamydia,* HIV etc.), stress, all forms of surgery such as organ transplant, tissue repair, reconstructive surgery, all forms of cancer, vision care, dental care, alcoholism, aging, etc.

NT Factor (NT1) has been tested in both human clinical studies and animal models. Seidman et al. found that NT Factor prevented hearing loss associated with aging in 18-20 month old rats. NT Factor shifted the threshold hearing from 35-40 db in controlled aged animals to 13-17 db in the test group. The results were significant (p<0.005). They also found that NT Factor preserved cochlear mitochondrial function as measured in Rhodamine-123 transport assays, increasing mitochondrial function by 34%. Rhodamine-123 is transported into mitochondria where it is reduced only under conditions where mitochondria are fully functional. (Seidman, M., Khan, M. J., Tang, W. X., et al. Influence of lecithin on mitochondrial DNA and age-related hearing loss. Otolaryngol Head Neck Surg. 127: 138-144 (2002)).

NT Factor (NT1) has been used in a vitamin and mineral mixture (Propax™; www.propax.com) in cancer patients to reduce the effects of cancer therapy, such as chemotherapy-induced fatigue, nausea, vomiting and other side effects associated with chemotherapy (Colodny L., Lynch K., Farber C., Papish S., et al. *JANA* 2:17-25, 2000).

In a twelve week double-blinded, crossover, placebo controlled, randomized trial on cancer patients receiving chemotherapy, Propax™ (containing NT Factor) supplementation resulted in improvement from fatigue, nausea, diarrhea, impaired taste, constipation, insomnia and other quality of life indicators. Sixty-four percent (64%) of the patients in the study reported significant improvement in these and other chemotherapy-induced side effects and an additional 29% showed beneficial results as evidenced by a stabilization of side-effects (no further increase in side effects). In subsequent treatment of the control group with the Propax™ supplements used in the study, the patients now receiving the Propax™ supplement reported rapid improvement in nausea, impaired taste, tiredness, appetite, sick feeling and other indicators. Propax™ including NT Factor was used in a pilot study with severely fatigued, aged subjects (>60 years-old) with a variety of clinical diagnoses to reduce fatigue, as measured by the Piper Fatigue Scale (Piper B. F., Linsey A. M., Dodd, M. *J. Oncol. Nursing Forum,* 14:17-23, 1987; Piper B. F., Dribble S. L., Dodd M. *J. Oncol. Nursing Forum,* 25:667-684, 1998). It was found that fatigue was reduced approximately 40%, from severe to moderate fatigue, after eight weeks of using Propax containing NT Factor. The results were highly significant (p<0.0001) (Ellithorpe R. R., Settineri R., Nicolson G. L. *JANA,* 6(1):23-28, 2003).

Figures 6, 7:
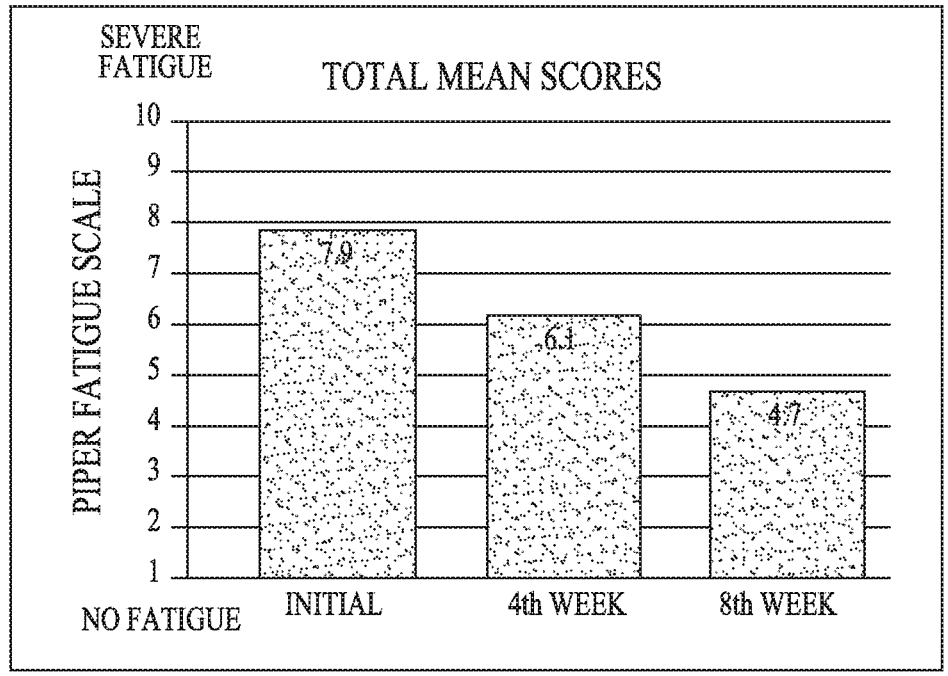
FIG. 6 is a chart showing the efficacy of prior available NT Factor.
FIG. 7 is an example of PL distributions in various human organs.

Another study examined the effects of NT Factor (NT1) on fatigue in moderately and mildly fatigued subjects. The study was designed to determine if their mitochondrial function, as measured by the transport and reduction of Rhodamine-123, in concert with improvements in fatigue scores, improved with administration of NT Factor. The results of this clinical trial are shown in FIG. 6 (Agadjanyan, M., Vasilevko, V., Ghochikyan, A., Berns, P., Kesslak, P., Settineri, R. A. and Nicolson, G. L.; Nutritional Supplement (NT Factor) Restores Mitochondrial Function and Reduces Moderately Severe Fatigue in Aged Subjects. *J. Chronic Fatigue Syndr.,* 11(3): 23-36 (2003)).

After eight or twelve weeks of NT Factor, there was a 33% or 35.5% reduction in fatigue, respectively. The results obtained using a validated instrument for measuring fatigue were highly significant (p<0.001). In the lipid replacement trial with moderately fatigued patients reductions in fatigue paralleled the significant gains in mitochondrial function. In addition, there was good correspondence between fatigue and mitochondrial function (FIG. 6). Mitochondrial function was significantly (p<0.001) improved by the use of NT Factor for just eight weeks.

After 12 weeks of NT Factor use mitochondrial function was similar to that found in young, healthy adults (FIG. 6). 12 weeks after NT Factor use was discontinued, the subjects' fatigue and mitochondrial function was re-measured. Their fatigue and mitochondrial function were intermediate between the starting values and those found on eight or 12 weeks of NT Factor, indicating that continued use of the supplement is likely required to maintain lower fatigue scores and show improvements in mitochondrial function. The results indicate that mitochondrial lipid replacement therapy can significantly restore mitochondria function (Nicolson, G. L. and Ellithorpe, R. *J. Chronic Fatigue Syndr.*, 13(1): 57-68, 2006).

Based on these studies, it was concluded that the decline of energy production with aging and in certain disease conditions appears to be related, in part, to mitochondrial membrane lipid peroxidation by ROS and RNS and the failure to repair or replace the damaged membrane molecules. Membrane damage and subsequent mitochondrial dysfunction by ROS can also lead to modifications (especially mutations and deletions) in mitochondrial DNA (mtDNA). The mitochondrial theory of aging proposes that the development of chronic degenerative diseases is the result, in part, of accumulated mtDNA mutations and deletions and oxidative damage to mitochondrial membranes over time (Wei Y. H., Lee H. C. *Exp. Biol. Med.*, 227:671-682, 2002; Sastre J., Pallardo F. V., Garcia de la Asuncion J., Vina J., *Free Radical Res* 32(3): 189-198, 2000; Kowald A. *Exp. Gerontol.*, 34:605-612, 1999).

These studies link the development of certain chronic diseases with the degree of mitochondrial membrane lipid peroxidation and mtDNA damage. Thus the damage to mtDNA and mitochondrial membranes seems to be involved in the etiology of age-associated degenerative diseases leading to changes in the expression of genes important for cell survival as well as the phenomenon of aging itself. Restoration of mitochondrial membrane integrity and fluidity are important for the optimal functioning of the electron transport chain. Declines in energy production with aging and disease coupled with increases in oxidative stress can modify membrane lipids and increase mitochondrial membrane permeability and activate cellular death programs (apoptosis) (Koboska, J., Coskun, P., Esposito, L., Wallace, D. C. *Proc. Nat. Acad. Sci. USA* 98:2278-2283, 2001). Together these factors likely play a major role in the aging process and they also affect the development of age-related degenerative diseases (Johns, D. R. N. Engl. J. Med. 333: 638-44, 1995).

Effects of New Lipid Formulation on Fatigue Reduction within One Week

Previous studies of the original proprietary formulation of NT Factor (the composition shown in Table 1) showed reduction of fatigue at two and three month intervals. However, significant and unexpected improvements in the level of change and the rapidity of improvement was found utilizing a New Lipid Formulation listed in Table 2 below (also referred to herein as NT2).

TABLE 2

NEW LIPID FORMULATION (NT2)

| Species | Percent Total* | Percent 18:2 (LINOLEIC ACID) |
|---|---|---|
| DGDG | 5.88 | 1.23 |
| MGDG | .301 | .149 |
| PG | 2.37 | .275 |
| Lyso-PG | .057 | .023 |
| PC | 31.62 | 11.61 |
| Lyso-PC | .982 | .614 |
| PE | 18.86 | 6.86 |
| Lyso-PE | .698 | .350 |
| PI | 24.87 | 3.30 |
| PS | .471 | .067 |
| PA | 13.88 | 5.63 |
| Total | 99.99 | 30.11 |

A clinical study was conducted to measured fatigue levels at the end of one week post-treatment. An online survey for fatigue was used to assess the effects of the New Lipid Formulation in combination with an antioxidant/vitamin mixture, the combination referred to as NT2 B-Vitamin Complex. The NT2 B-Vitamin Complex used in the study comprised NT2 with the addition of an antioxidant/vitamin mixture as listed below in Table 3:

TABLE 3

NT2 B-Vitamin Complex

| Daily Dose Size 5 Tablets Amount Per Daily Dose | | % Daily Value** |
|---|---|---|
| Vitamin E (as d-alpha tocopheryl succinate, mixed tocopherols) | 50 IU | 167% |
| Thiamin (Vitamin B-1) (as thiamine HCl) | 3.75 mg | 250% |
| Riboflavin (Vitamin B-2) | 4.25 mg | 250% |
| Niacin (Vitamin B-3) (as niacinamide, niacin) | 100 mg | 500% |
| Vitamin B-6 (as pyridoxine HCl) | 10 mg | 500% |
| Folate (as folic acid) | 800 mcg | 200% |
| Vitamin B-12 (as methylcobalamin, cyanocobalamin) | 1,000 mcg | 16,667% |
| Biotin | 750 mcg | 250% |
| Pantothenic acid (as d-calcium pantothenate) | 25 mg | 250% |
| Calcium (as dicalcium phosphate, carbonate, pyruvate, borogluconate, ascorbate and d-Calcium pantothenate) | 400 mg | 40% |
| Phosphorus (as dicalcium phosphate) | 125 mg | 13% |
| Magnesium (as magnesium oxide) | 125 mg | 31% |
| OptiMSM ™ Methylsulfonylmethane | 364 mg | † |
| Alpha Keto Glutaric Acid | 300 mg | † |
| L-Carnipure ® L-Carnitine L-tartrate | 225 mg | † |
| L-Tyrosine | 150 mg | † |
| NT 2 | 4,000 mg | † |

† Daily Value not established.
**Daily Values are based on a 2,000 calorie per day diet.
Other ingredients: Vegetable stearic acid, croscarmellose sodium, vegetable stearate, microcrystalline cellulose, silicon dioxide, pharmaceutical glaze.

The NT2 B-Vitamin Complex significantly reduced fatigue as gauged by the Piper Fatigue Scale (PFS) (a validated survey instrument which was adapted to online use) within one week by a mean of 36.8% (p<0.001) in a group of 67 subjects with mean age of 57.3 years and various levels of fatigue. This is a significant improvement over the results using the NT Factor formulation described above. There was no difference between the response of males and females to the supplement and no adverse events occurred during the study.

Test subjects had a measurable fatigue (3-10 on the PFS). Each participant took the suggested daily dose divided into 3 tablets in the morning and 2 at night of the NT2 B-Vitamin Complex (the composition described above) for one week. All subjects repeated the PFS assessment at the end of the first week on line without access to their previous scores. The PFS is composed of 22 numerically scaled questions rated from 0 (no fatigue) to 10 (severe) fatigue. These questions measure four dimensions of subjective fatigue: behavioral/severity (6 questions); affective/meaning (5 questions); sensory (5 questions); and cognitive/mood (6 questions). The answers are used to calculate the four sub-scale/dimensional scores and the total fatigue scores. The standardized alpha (Cronbach's alpha) did not drop below 0.90 for any of the subscales, and the standard alpha for the entire scale of 22 questions was 0.96, indicating excellent reliability for an established instrument.

The NT2 B-Vitamin Complex improved the overall fatigue scores of moderately fatigued subjects as measured by the PFS (Table 4). The initial PFS group average (mean±standard error mean) total fatigue score was 9.56±0.36, and after one week of supplement this improved to 6.02±0.295 or a 36.8% reduction in fatigue. The mean decrease in fatigue value was significant by t-test ($p<0.001$) and Wilcoxon signed-rank ($p<0.001$) analyses. There were no adverse events during the course of the study.

The Piper Fatigue Scale can be further dissected into subcategories that include overall fatigue, behavior/severity, affective meaning, sensory and cognitive/mood (Table 5). All of these subcategories showed reductions of 34.6% to 40.6% at the end of the one-week trial, indicating that there were improvements in all subcategories of fatigue.

The NT2 B-Vitamin Complex formula resulted in a 35.4% reduction in fatigue by the end of one week. In comparison, the prior available NT Factor formula (NT1) (Table 1) required 8 to 12 weeks to effect a lesser or equivalent fatigue reduction. This finding is a substantial improvement over prior performance of an older, different lipid formulation with the new NT2 B-Vitamin Complex formula as described herein.

TABLE 4

Results from Piper Fatigue Scale Survey with the NT2 B-Vitamin Complex Treatment

| Category | n | Mean Age ± S.E.M. | Mean Fatigue Level ± S.E.M. | | Percent Reduction |
|---|---|---|---|---|---|
| | | | Day 0 | Day 7 | |
| Male | 31 | 59.2 ± 2.4 | 4.3 ± 0.20 | 2.8 ± 0.18 | 34.4 |
| Female | 36 | 55.6 ± 2.0 | 4.4 ± 0.25 | 2.7 ± 0.20 | 39.2 |
| All subjects | 67 | 57.3 ± 1.5 | 4.3 ± 0.16 | 2.8 ± 0.13*# | 36.8 |

*t-test p < 0.001
Wilcoxon signed-rank p < 0.001

TABLE 5

Results from Subcategories of the Piper Fatigue Scale Survey with the NT2 B-Vitamin Complex Treatment

| Category | Mean Fatigue Level ± S.E.M. | | Percent Reduction |
|---|---|---|---|
| | Day 0 | Day 7 | |
| Overall Fatigue | 4.3 ± 0.16 | 2.8 ± 0.13 | 36.8 |
| Behavior/Severity | 4.8 ± 0.05 | 2.9 ± 0.03 | 37.8 |
| Affective/Meaning | 4.3 ± 0.03 | 2.8 ± 0.05 | 34.6 |

TABLE 5-continued

Results from Subcategories of the Piper Fatigue Scale Survey with the NT2 B-Vitamin Complex Treatment

| Category | Mean Fatigue Level ± S.E.M. | | Percent Reduction |
|---|---|---|---|
| | Day 0 | Day 7 | |
| Sensory | 4.2 ± 0.04 | 2.7 ± 0.01 | 33.9 |
| Cognitive/Mood | 4.1 ± 0.04 | 2.4 ± 0.02 | 40.6 |

(Nicolson, G. L., Ellithorpe, R., Ayson-Mitchell, C., Jacques, B and Settineri, R, Lipid Replacement Therapy with a Glycophospholipid-Antooxidant-Vitamin Formulation Significantly Reduces Fatigue Within One Week. J. American Nutraceutical Association, 13(1): 10-14 (2010))

Lipids Energy Drink (NT3) Survey Results

Following are test results for a new lipids liquid formulation, referred to herein as NT3, which contained only the phospholipid composition (NT2) listed in Table 2 above, delivered as a liquid energy drink.

TABLE 6

Lipids Energy Drink (NT3)

Serving Size 2 FL OZ.

| Amount Per Serving (59 ml | | % Daily value |
|---|---|---|
| Calories | 3.65 | <2.0% |
| Calories from Fat | 2.55 | † |
| Calories from Saturated Fat | 0.00 | † |
| Total Fat: | 0.27 g | <2.0% |
| Saturated Fat | 0.06 g | <2.0% |
| Trans Fat | 0.00 g | † |
| Monounsaturated Fat | 0.03 g | † |
| Polyunsaturated Fat | 0.17 g | † |
| Cholesterol | 0.00 mg | <2.0% |
| Total Carbohydrates | 0.06 g | <2.0% |
| Dietary Fiber | 0.00 g | <2.0% |
| Sugars | 0.02 g | † |
| Sugar Alcohols | 0.00 g | † |
| Other Carbohydrates | 0.04 mg | † |
| Sodium | 0.16 g | <2.0% |
| Protein | 0.00 g | 0 |
| NT Lipids 3 | 600.00 mg | † |

† Daily Value not established.
**Daily Values are based on a 2,000 calorie per day diet.
Other ingredients: Purified Water, Innulin, Safflower Oil, Natural Mixed Berry Flavor, Stevia, Red Beet, Citric Acid The effects of the Lipids Energy Drink (NT3) were evaluated on a population of 55 volunteers (29 men and 26 women) with an average age of 56 years. This study was performed to determine the effects of this newly formulated composition of phospholipids on energy levels, fatigue, cognitive function and mental clarity. 600 mg of the formula was suspended in two ounces of water with mixed berry flavoring along with stevia as a sweetener. Specific lipids described herein were administered in a two ounce drink to a general population of twenty-nine men and women (average age of 56 years). Before the drink was given to the subjects, they fill out the Piper Fatigue Survey questionnaire (PFS). Immediately after completing the survey each volunteer drank the NTF Lipid (NT5) supplement. Two hours post treatment they filled out the PFS questionnaire again. A supplementary questionnaire was also used in addition to the PFS and filled out after the two hours post-treatment period.

Figure 8:
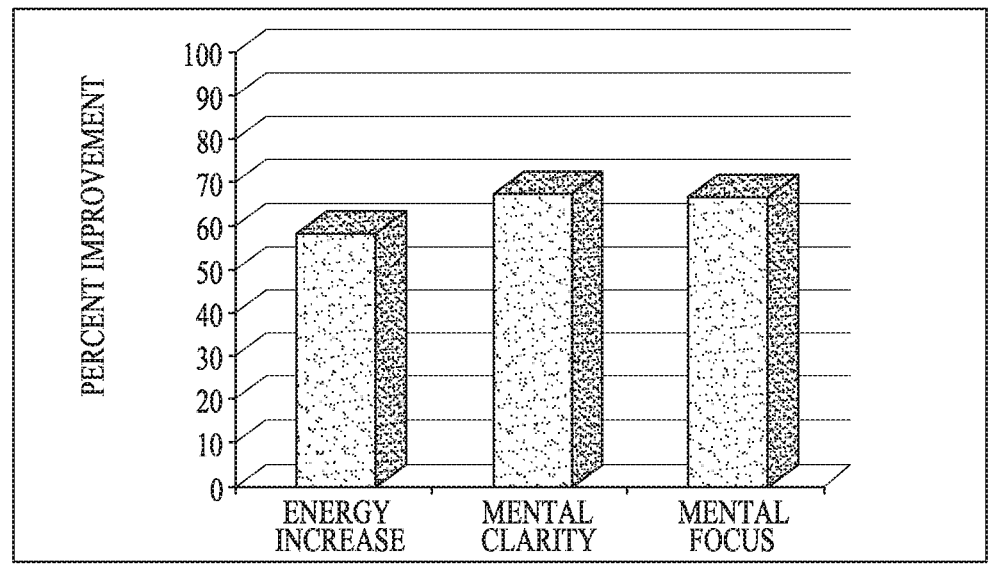
FIG. 8 is a chart showing short-term efficacy of lipids treatment.

Results: PFS responses of pre and post treatment were compared and statistically analyzed by means of a paired two-tailed t-Test. Overall fatigue was reduced by 36.2% ($P<0.0006$) at the end of the two hour test period. The subscales of Behavioral/Severity, Affective/Meaning, Sensory, and Cognitive/Mood were reduced after NT3 administration by 32.3% (P<0.0007), 34.1% (P<0.0016), 29.8% (P<0.024) and 27.6% (P<0.0001) respectively (Table 7). Ninety-one percent of the participants claimed they felt a boost of energy within a several hour period after drinking the NT3 composition. The group scored a 59 percent improvement in energy or "energy increase," a 68 percent improvement in mental clarity and a 67 percent improvement in mental focus (FIG. 8).

TABLE 7

NT3 Lipids Piper Fatigue Survey Results

| Parameter | Pre-treatment | Post-treatment | % Reduction | P Value |
|---|---|---|---|---|
| Overall Fatigue | 3.29 ± 0.33 | 2.10 ± 0.25 | 36.2 | <0.0006 |
| Behavior/Severity | 2.54 ± 0.10 | 1.72 ± 0.10 | 32.3 | <0.0007 |
| Affective/Meaning | 2.99 ± 0.14 | 1.97 ± 0.16 | 34.1 | <0.0016 |
| Sensory | 4.06 ± 0.42 | 2.85 ± 0.68 | 29.8 | <0.0242 |
| Cognitive/Mood | 3.59 ± 0.11 | 1.88 ± 0.10 | 47.6 | <0.0001 |

Figure 21:
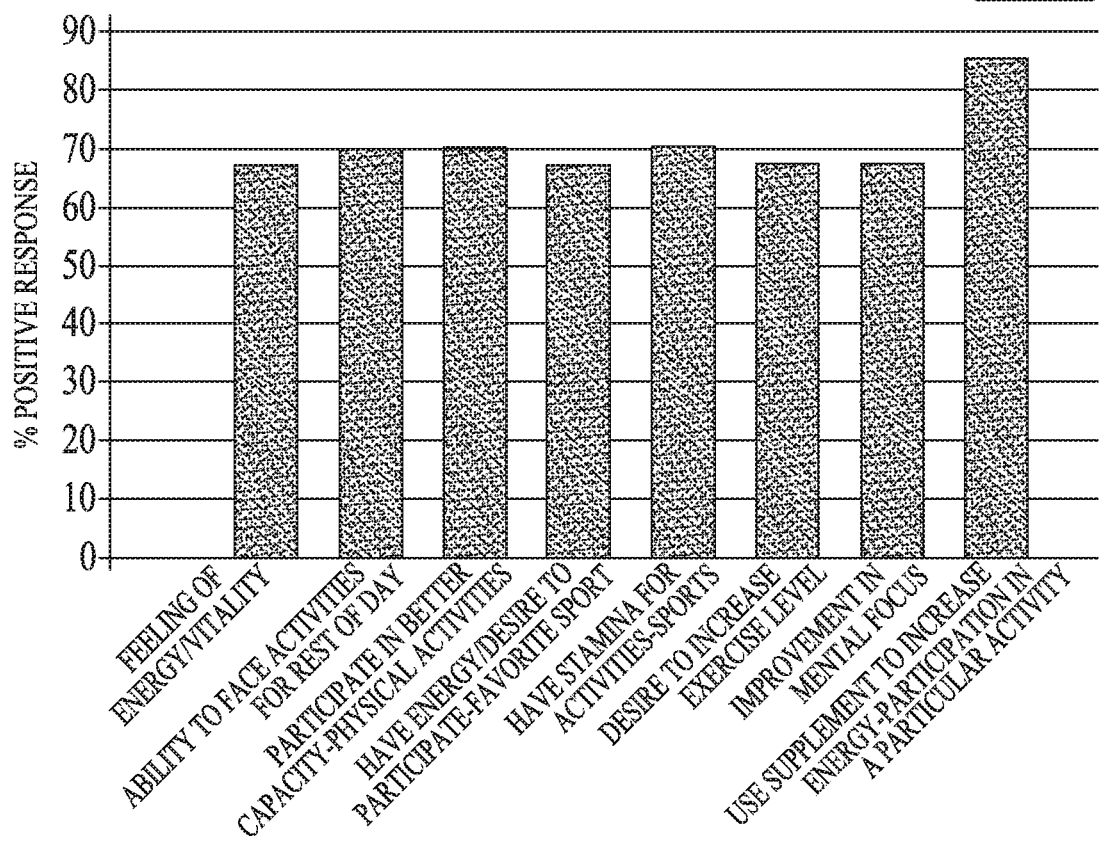
FIG. 21 is a chart showing energy assessment of a new Lipid Formulation.
Figure 22:
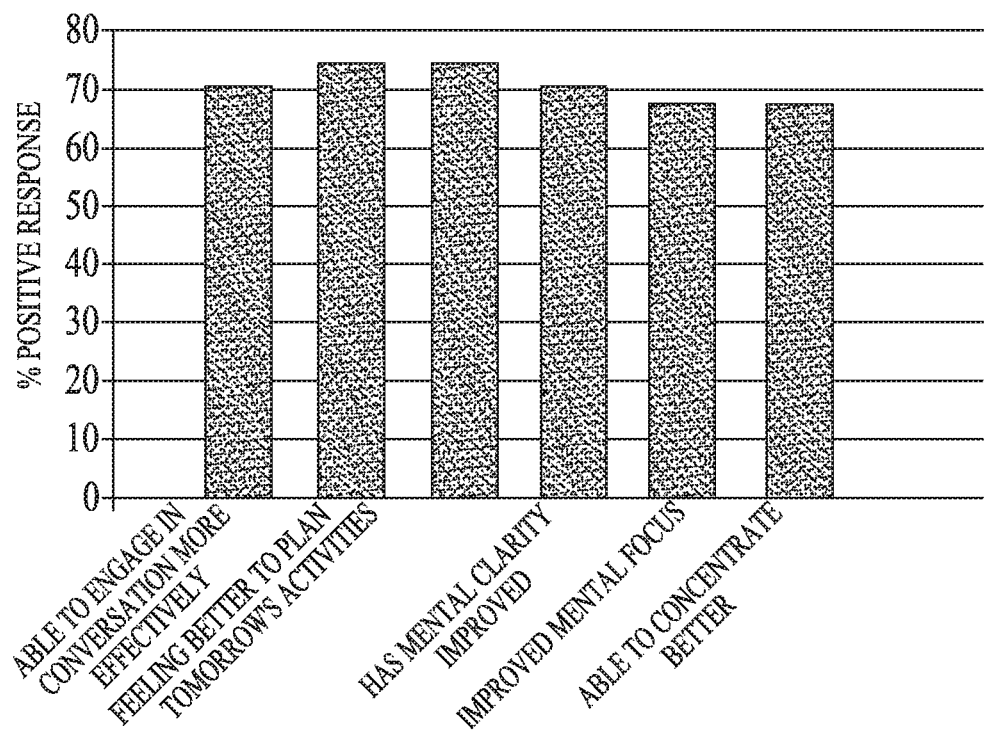
FIG. 22 is a chart showing change in cognitive function.
Figure 23:
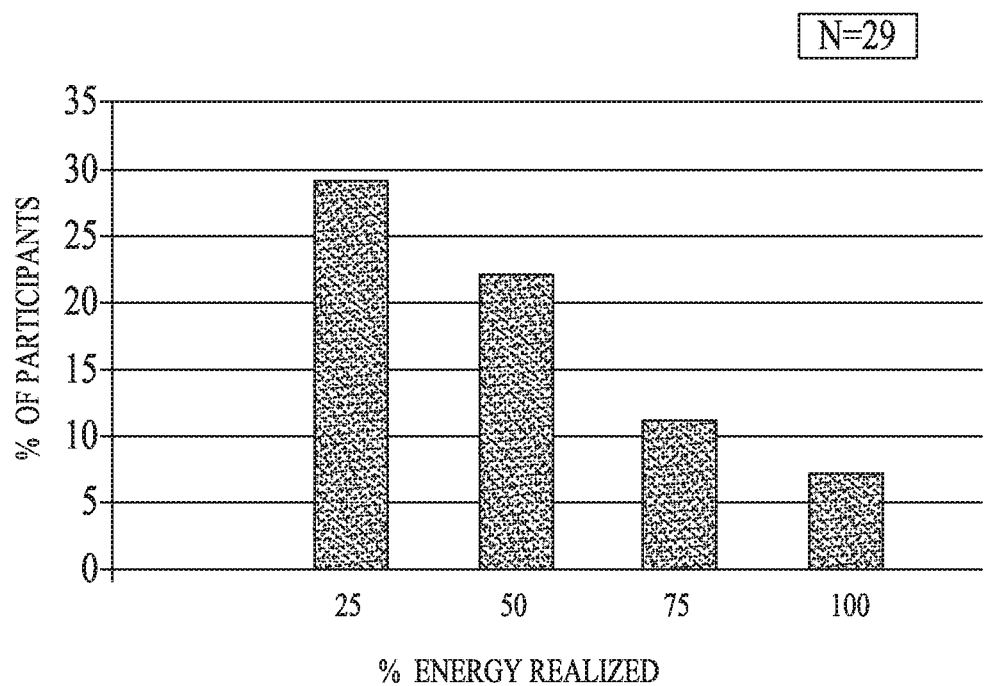
FIG. 23 is a chart showing energy time assessment.

Within the same trial, a supplemental questionnaire was answered by the participants two hour post treatment. Responses showed approximately 70% of the respondents experience increased energy, increased mental clarity, increased mental focus and increased concentration within one hour after taking the supplement. (FIGS. 21, 22). Twenty-five percent of the test group reported a feeling of increased energy within 15 minutes, seven percent reported a feeling of increased energy within 30 minutes, twenty-one percent within 45 minutes and eighteen percent reported increased energy within one hour after taking the supplement (FIG. 23).

The ability to significantly affect a fatigue reduction (energy increase) within a two hour period and the increased feeling of energy, mental clarity, mental focus and concentration by use of the NT5 composition has shown improvement over prior art. It should be noted that the prior NT Factor alone has not been found to be effective in this short time frame. Previously NT Factor was studied in clinical setting for a minimum of two months where a 45% reduction in overall fatigue was shown compared to this recent study of significant reduction of fatigue within a two hour period.

These data show a perception of increased energy and cognitive function within several hours after taking the Lipids Energy Drink NT3 supplement. This study reveals an improvement over prior art, utilizing the Lipids Energy Drink (NT3) phospholipid formula by demonstrating relatively immediate beneficial responses as opposed to the prior lipid composition (NT1) which required two to three months, as reported in previous proprietary phospholipid formulae studies, to obtain comparable anti-fatigue results.

TABLE 8

LIPIDS WITH ADDITION OF PHASEOLUS (NT4)

Serving Size 2 Tablets
Amount Per Serving

| | | % Daily Value** |
|---|---|---|
| Calcium (as dicalcium phosphate, calcium pyruvate, calcium borogluconate, calcium ascorbate) | 79 mg | 7.9% |
| Phosphorus (as dicalcium phosphate) | 60 mg | 6% |
| NT 2 | 500 mg | † |
| White Kidney Bean Extract (phaseolus vulgaris) | 500 mg | † |
| OptiMSM ® | 46 mg | † |

† Daily Value not established.
**Daily Values are based on a 2,000 calorie per day diet.
OptiMSM ® is a dietary food supplements containing methylsulfonylmethane available from Cardinal Associates, Inc. Vancouver Washington
Other ingredients: Dicalcium phosphate, microcrystalline cellulose, vegetable stearic acid, vegetable stearate, croscarmellose sodium, silicon dioxide, pharmaceutical glaze.

Effect of NT2 Lipids with Addition of *Phaseolus* (NT4) on Weight, Girth, Body Mass, Appetite and Fatigue A weight loss clinical trial using an all natural oral supplement mixture containing an FDA-approved amylase inhibitor is described herein.

The objective was to determine if subjects could safely lose weight without increasing appetite and fatigue and without changing eating or exercise patterns or using drugs, herbs or caffeine. A two-month open label clinical trial was initiated with 30 patients who used an oral mixture (Healthy Curb™) of NT4 comprising an amylase inhibitor (500 mg white kidney bean extract) plus 500 mg of NT2 thirty minutes before each meal. Weight and measurements were taken weekly, appetite was assessed and fatigue was determined using the Piper Fatigue Scale (Piper B F, Dribble S L, Dodd M J, et al. The revised Piper Fatigue Scale: Psychometric evaluation in women with breast cancer, *Oncol Nursing Forum* 1998; 25:667-684). Sixty-three percent of the participants lost an average of 6 pounds along with 2.5 and 1.5 inch reductions in waist and hip circumference, respectively, and the entire group of participants lost an average of 3 pounds with average reductions of 1.5 and 1 inch waist and hip circumference, respectively. Participants experienced gradual and consistent weight loss along with waist and hip, body mass index (BMI) and basal metabolic rate (BMR) reductions during the entire trial. There was a 44% reduction in overall hunger with reduced cravings for sweets evidencing the occurrence of notable appetite suppression. Using the Piper Fatigue Scale the entire test group showed an average of 23% decrease in overall fatigue. Blood lipid profiles generally improved, suggesting improved cardiovascular health, and no adverse effects were noted clinically or found in blood chemistry (Nicolson, G. L., Ellithorpe, R., and Settineri, R. Dietary Supplement Healthy Curb for Reducing Weight, Girth, Body Mass, Appetite And Fatigue While Improving Blood Lipid Values With NTFactor Lipid Replacement Therapy. J. Invest Myalgic Encephalomyelitis 3(1): 39-48 (2009). While the article title refers to NT Factor the lipid composition used was NT2, not NT1).

Conclusions: The vast majority of the subjects in this trial lost weight, showed decreased waist and hip measurements and overall body mass. Their overall fatigue was reduced, and they experienced marked appetite suppression. The NT2 formulation was found to be completely safe and void of any side effects and was extremely well tolerated and appears to be a safe and effective means for people to manage weight without changes in eating or exercise patterns.

Figure 9:
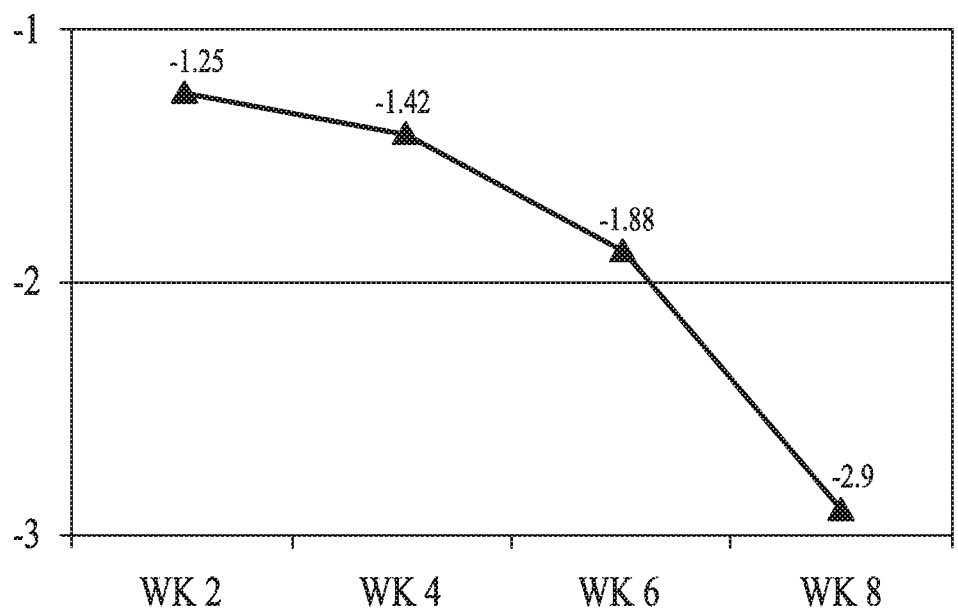
FIG. 9 is a chart showing average weight loss over eight weeks for the entire group.
Figure 10:
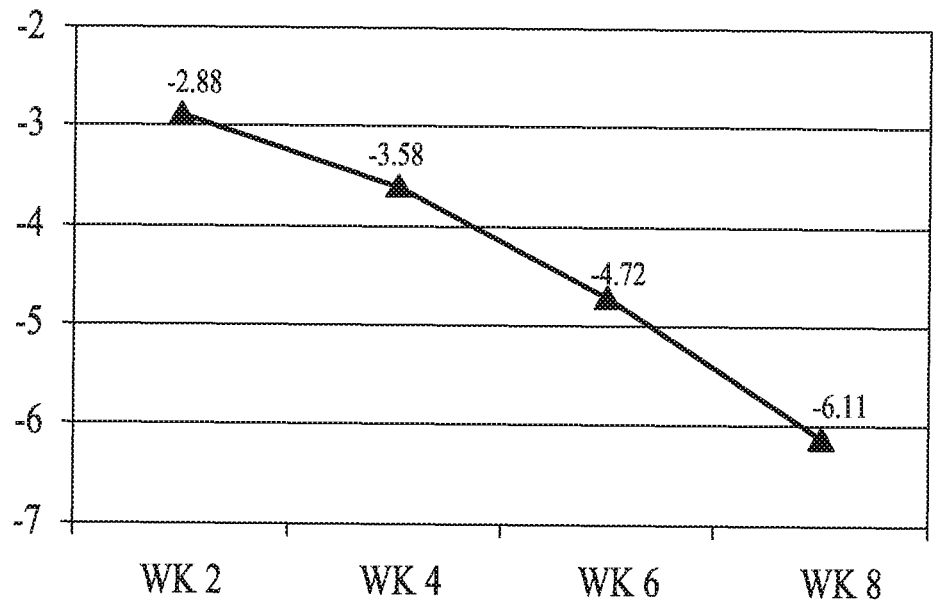
FIG. 10 is a chart showing average weight loss over eight weeks for the responder group.
Figure 11:
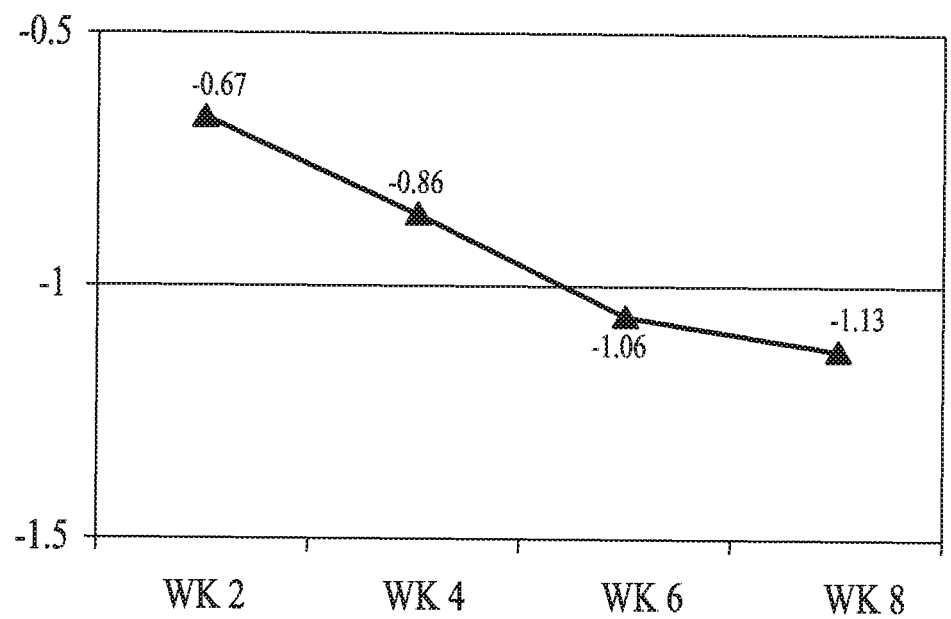
FIG. 11 is a chart showing average hip measurement loss for the entire group.
Figure 12:
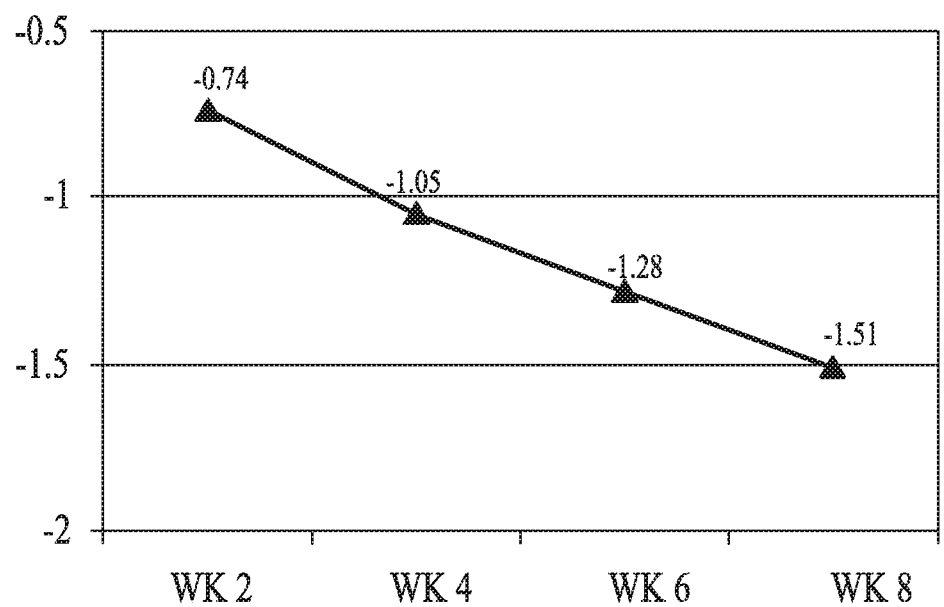
FIG. 12 is a chart showing average hip measurement loss for the responder group.
Figure 13:
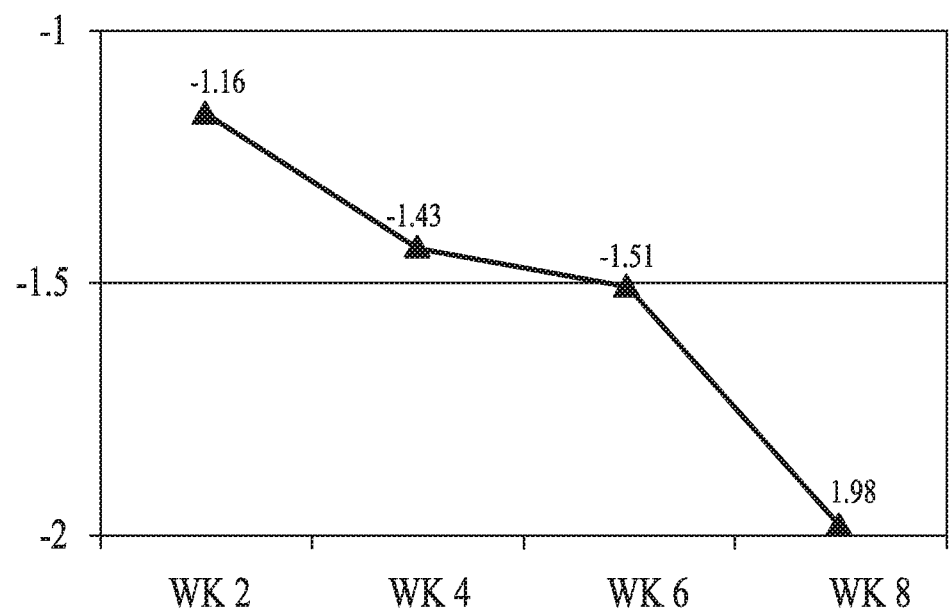
FIG. 13 is a chart showing average waist measurement loss for the entire group.
Figure 14:
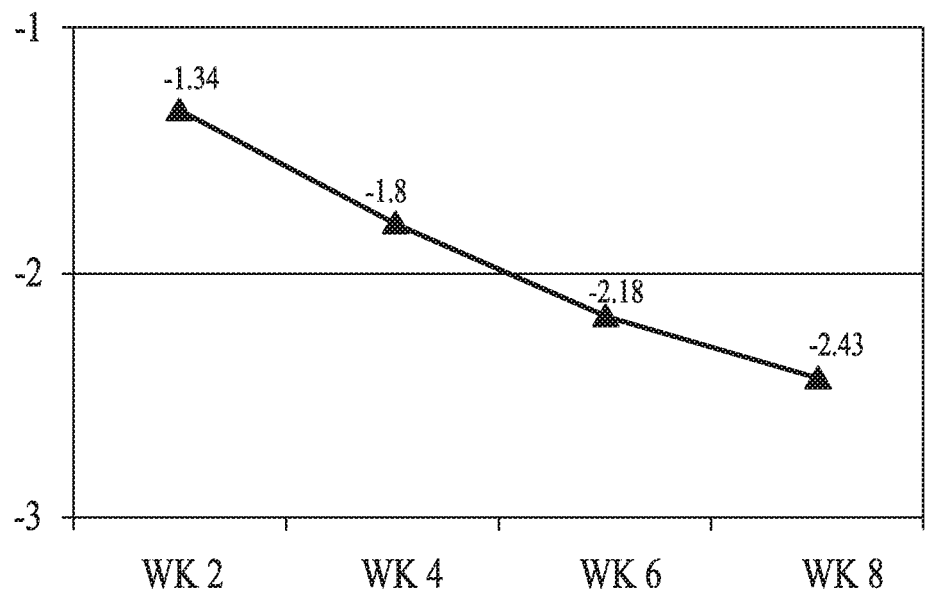
FIG. 14 is a chart showing average waist measurement loss for the responder group.

Weight and Girth Reduction: The entire group of participants lost an average of 3 pounds (FIG. 9) with average reductions of 1.5 and 1 inches in hip and waist circumference, respectively (FIGS. 10, 11). Sixty-three percent of the participants (responder group) lost an average of 6 pounds (FIG. 12) along with 2.5 and 1.5 inches reduction in hip and waist circumference, respectively (FIGS. 13, 14), and participants experienced gradual and consistent weight loss along with waist and hip reductions during the entire trial.

Figure 15:
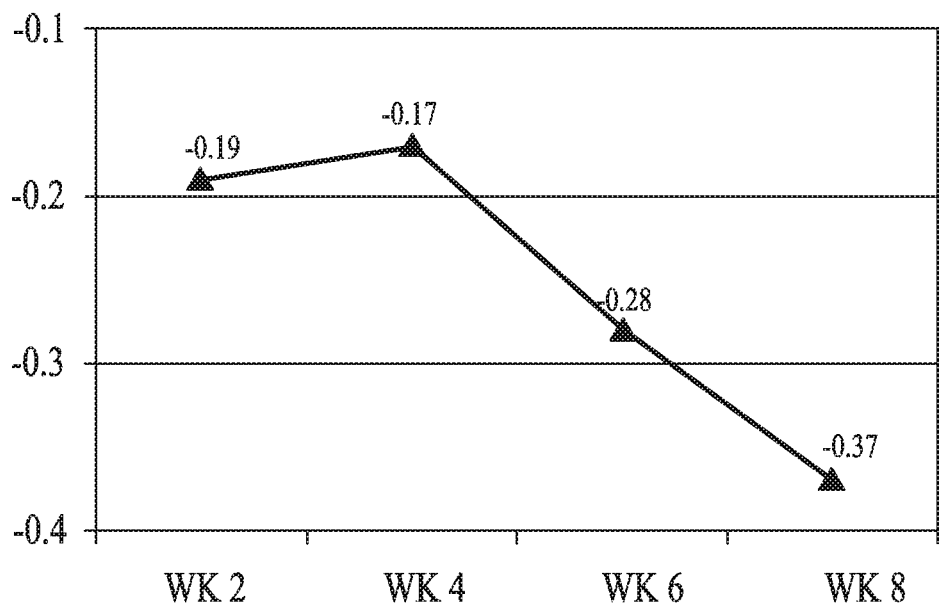
FIG. 15 is a chart showing average body mass index loss for the entire group.
Figure 16:
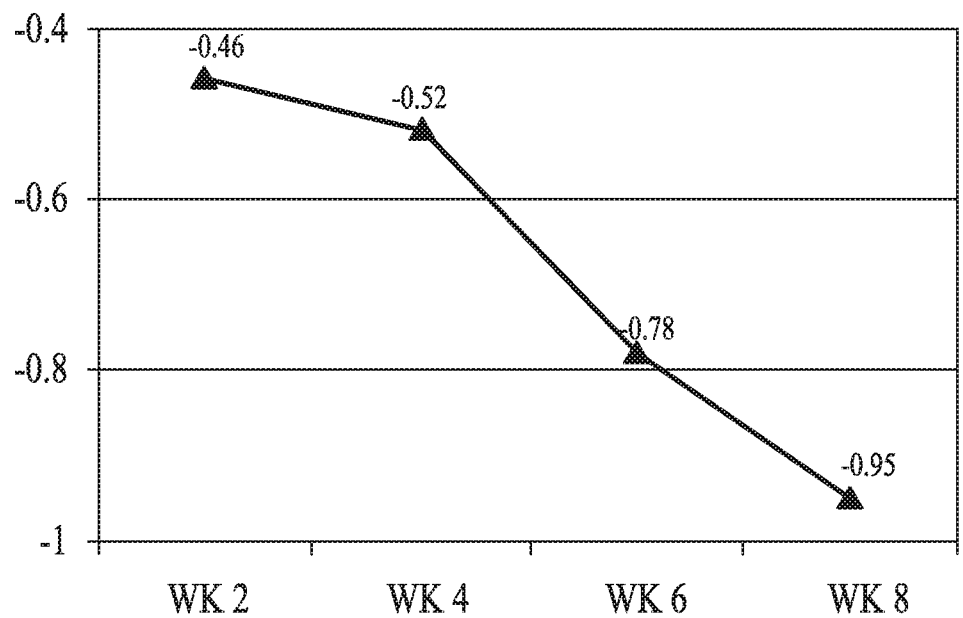
FIG. 16 is a chart showing average body mass index loss for the responder group.

Body Mass Index Reduction: Body mass index (BMI) was calculated as the weight (in pounds) times 703 divided by height (inches) squared. There was a reduction in average BMI in the entire group of 0.18 (FIG. 15) and in the responder group of 0.49 (FIG. 16).

Figure 17:
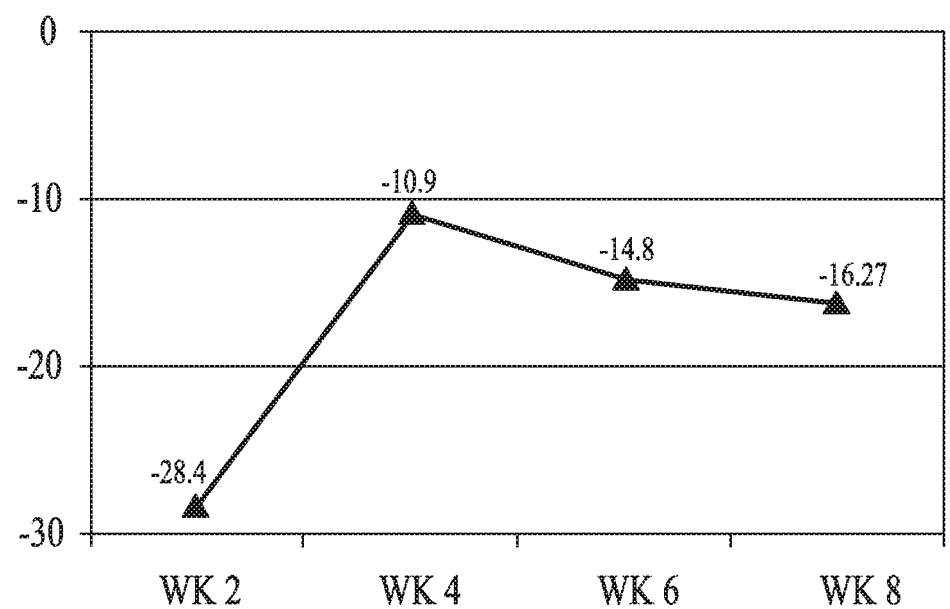
FIG. 17 is a chart showing average basal metabolic rate gain for the entire group.
Figure 18:
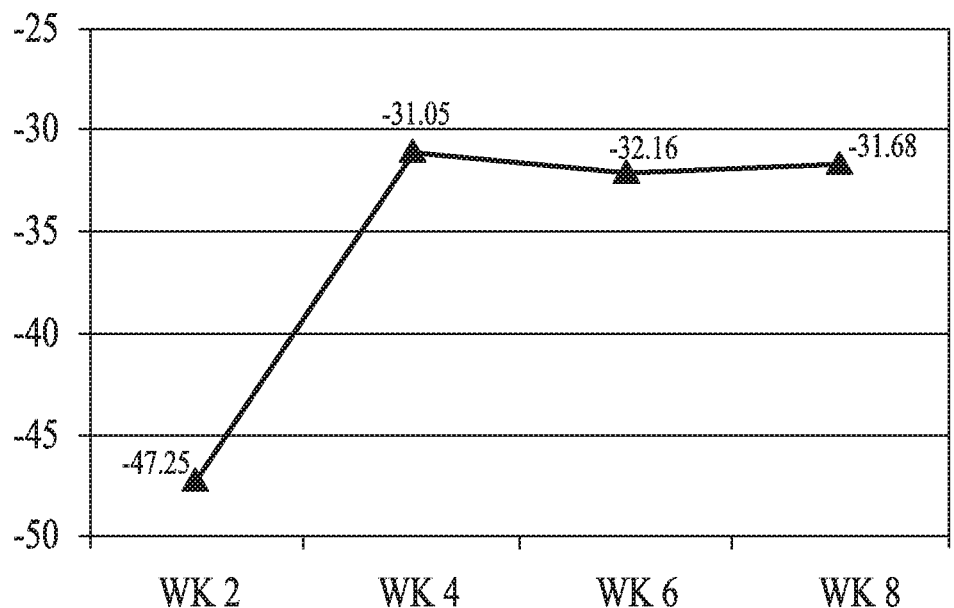
FIG. 18 is a chart showing average basal metabolic rate gain for the responder group.

Basal Metabolic Rate Reduction: Basal Metabolic Rate (BMR) uses the variables of height, weight, age and gender to calculate a rate of resting metabolism. The overall change in BMR and change in the responder group are shown in FIGS. 17, 18. These were calculated as follows:

Women: BMR=655+(9.6×weight in kilos)+(1.8×height in cm)−(4.7×age)

Men: BMR=66+(13.7×weight in kilos)+(5×height in cm)−(6.8×age in years)

Figure 19:
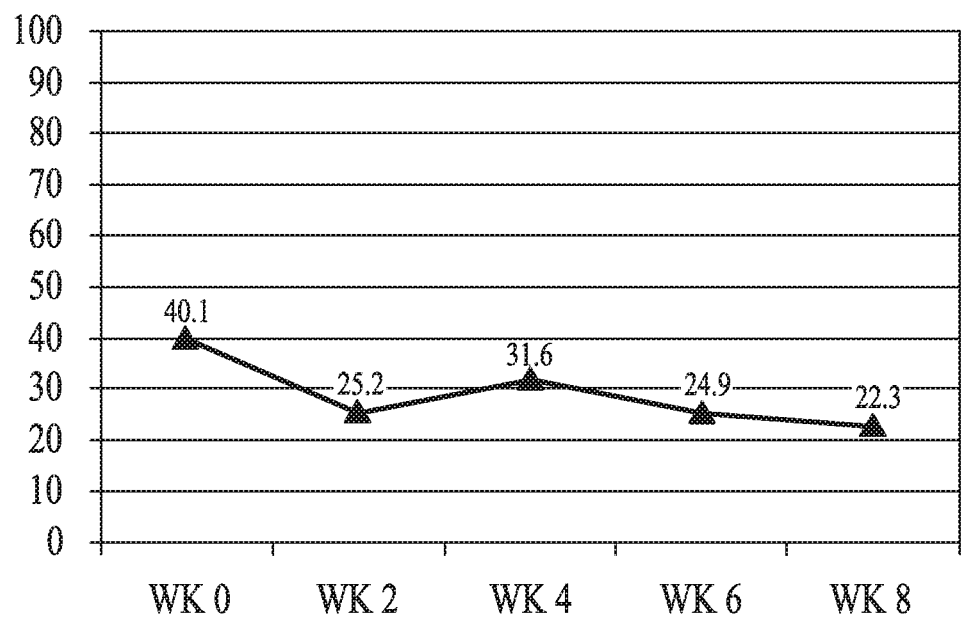
FIG. 19 is a chart showing average hunger index for the entire group.

Appetite Suppression: There was a 44% reduction in overall hunger (FIG. 19) with reduced cravings for sweets; therefore, notable appetite suppression occurred.

Figure 20:
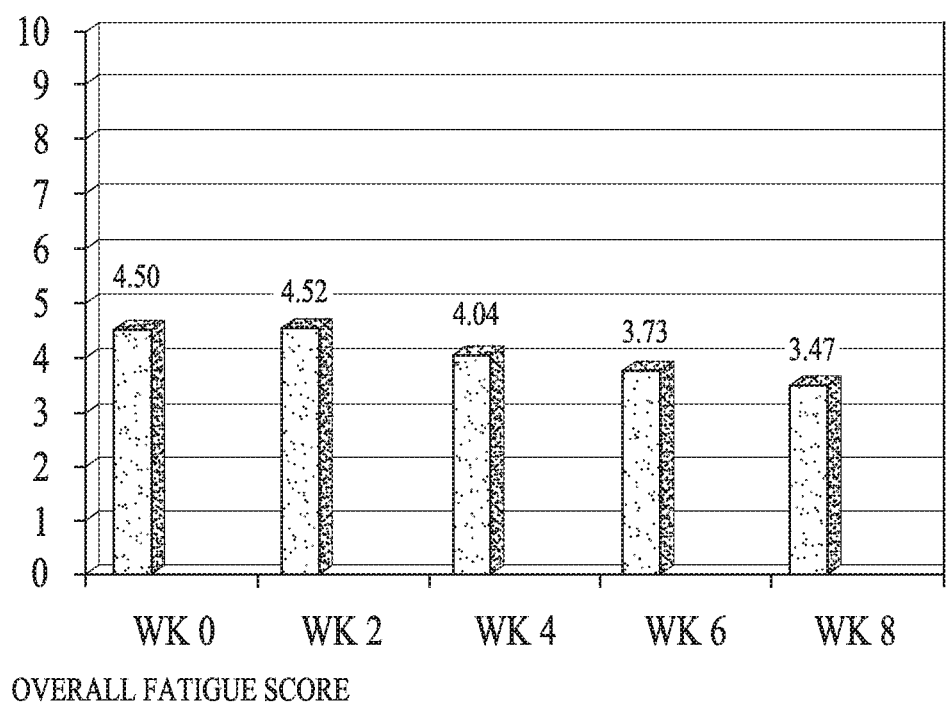
FIG. 20 is a chart showing overall fatigue score for the entire group.

Fatigue Suppression: Using the Piper Fatigue Scale the entire test group showed an average of 23% decrease in overall fatigue during the trial (FIG. 20).

Blood Lipid Profiles: Blood lipid profiles generally improved (Table 9), suggesting improved cardiovascular health, and no adverse effects were noted clinically or found in blood chemistries (data not shown).

TABLE 9

BLOOD LIPID CHEMISTRY

| Measurement | Day 0 | Day 60 |
| --- | --- | --- |
| Glucose | 104.8 mg/dl | 104.4 mg/dl |
| Cholesterol | 209.6 mg/dl | 200.7 mg/dl |
| Triglycerides | 142.6 mg/dl | 129.2 mg/dl |
| HDL | 56.9 mg/dl | 58.0 mg/dl |
| LDL (Calc) | 124.2 mg/dl | 116.8 mg/dl |
| VLDL (Calc) | 28.5 mg/dl | 25.8 mg/dl |
| Cholesterol/HDL Ratio | 3.9 | 3.7 |
| HDL/LDL Ratio | 2.4 | 2.1 |

Participants experienced gradual and consistent weight loss along with waist and hip, body mass index (BMI) and basal metabolic rate (BMR) reductions during the trial. The NT2 use in this trial is an improvement over prior art and is shown for the first time to suppress appetite, control weight, increase energy and reduce fatigue. Furthermore, no adverse effects were reported, and blood chemistries and lipid analyses indicated that subjects actually had improved lipid profiles at the end of the trial.

While it has been generally shown that mitochondrial function can be improved by delivery of phospholipids compositions, it is shown herein that the benefits of phospholipids delivery can be significantly enhanced by a new phospholipid formulation (NT2). Further benefits can be obtained by tailoring the composition to the specific organ, disease state or identified deficiency to be treated. This is not a mere optimization of the composition. Instead it requires the preparation of a specific combination of lipids and fatty acids as well as unique formulations obtained from new sources, including biological sources, to obtain a specific intended end result. As explained below, for normal functioning of each body organ and the cells within that organ, an organ-specific combination of phospholipids is required. In addition this organ-specific combination of phospholipids may be different, when used to treat different diseases. In any event, delivery of selected phospholipids to return the membrane, cell, organ or system to proper phospholipid balance, irrespective of whether the change is a cause or effect, is set forth herein as an effective approach to addressing that abnormality.

While commercially available phospholipids can be combined to form desired compositions for delivery to maintain normal phospholipids balance on a whole body basis or an organ specific basis or to address specific disease related phospholipids imbalances, an extraction, purification, fractionation and combination/composition procedure for plant, animal, fungal, algal, protozoan, and bacteria species is also disclosed herein. A lipid and phospholipid profile, which is enriched in specific phospholipid fractions such as PG, is thus obtained. This profile, aside from it being enriched in certain phospholipid fractions is similar to that resulting from use of extraction processes on lecithin from egg yolks, soy beans, and other sources, These procedures when used on plant, animal, fungal, algal, protozoan, and bacteria species can be used to prepare specifically desired compositions.

As an example, the composition of a particular embodiment of a New Lipid Formulation comprises the following phospholipids: PC 19-29%, preferably about 24%, PE 15-25%, preferably about 20%, PA 3.5%-10%, preferably about 7%, PI10-18%, preferably about 14%, PG 2-10%, preferably about 5%, glycolipids 10-20%, preferably about 15%, other phospholipids including phosphatidylserine (PS) 5-11%, preferably about 8%, the balance being other materials (all percentages listed herein are weight %.) for a total weight, of about 1,350 mg per unit where a daily dosage may be multiple units New Lipid Formulation A and Cyanithin A are enriched in phosphatidic acid and glycophospholipids based on phosphatidic acid. New Lipid Formulation C and Cyanithin C are enriched in phosphatidylcholine and glycophospholipids based on phosphatidylcholine. New Lipid Formulation E and Cyanithin E are enriched in phosphatidylethanolamine and glycophospholipids based on phosphatidylethanolamine. New Lipid Formulation G and Cyanithin G are enriched in phosphatidylglycerol and glycophospholipids based on phosphatidylglycerol. New Lipid Formulation I and Cyanithin I are enriched in phosphatidylinositol. New Lipid Formulation S and Cyanithin S are enriched in phosphatidylserine and glycophospholipids based on phosphatidylserine. A de-oiled new Lipid Formulation can be combined with triglyceride or other oils enriched in the particular fatty acid that is desired for an endpoint Combination product. For example, new Lipid Formulation A can be enriched with high linoleic acid oils such as safflower, sunflower, or grape seed oil. New Lipid Formulation S can be enriched in high oleic oils such as canola, pecan and other oils The composition of a particular Combination A which includes New Lipid Formulation A enriched with linoleic acid (sourced from safflower or sunflower) is listed in Table 10.

TABLE 10

COMBINATION A

| Species | Percent Total* | Percent 18:2 |
| --- | --- | --- |
| DGDG | 3.34 | 1.23 |
| MGDG | 0.18 | .149 |
| PG | 1.42 | .275 |
| Lyso-PG | 0.03 | .023 |
| PC | 18.97 | 11.61 |
| Lysp-PC | 0.59 | .614 |
| PE | 11.316 | 6.86 |

TABLE 10-continued

COMBINATION A

| Species | Percent Total* | Percent 18:2 |
|---|---|---|
| Lyso-PE | 0.42 | .350 |
| PI | 14.92 | 3.30 |
| PS | 0.28 | .067 |
| PA | 8.32 | 5.63 |
| Total Phospholipids | 51.67 | 24.48 (23.1) |
| Safflower Oil | 40 | 65-88 |
| Total Combination A | 99.67 | 58-67 |

As an example and not a restriction, a PC-enriched source of lipids can be obtained from either raw material or extracted lipids by the extraction described below and shown schematically in FIG. 4. An example of the process used for the extraction of lecithin to produce a New Lipid Formulation, such as NT2, comprises the following steps.

a) 120 grams of lecithin or a plant extract is combined with 6.25 to 25 grams of a suitable acid (see below) in 250 to 320 ml of 90% ethanol/10% water solution (Step A).

b) The mixture is brought to a boil and then removed from the heat (Step B).

c) The cooled mixture separates into a solvent (liquid) fraction and an insoluble fraction (Step C).

d) The solvent (liquid) fraction from Step C is cooled to 1° C. and the solvent (liquid) fraction is separated from a second insoluble fraction which forms on cooling (Step D).

e) The insoluble fraction separated in Step C and the second insoluble fraction from Step D are reserved for Step F below (Step E).

f) The solvent (liquid) fraction from Step D is concentrated, in Step E, by evaporating the ethanol/water mixture to leave a third solid fraction (Step F) Alternatively, the liquid fraction from Step D is used directly in Step H.

g) The insoluble fractions from Steps C and D are combined in 90 ml of 80% ethanol/20% water with 1 to 4 grams of a suitable acid (see below) (Step G) and brought to a boil.

h) The boiled solution from Step G is cooled to 5.5° C. to separate the solvent with dissolved material from the insoluble fraction (Step H) and the insoluble fraction is discarded.

i) The solvent fraction from Step D (or the dried material after evaporation in Step E) is combined with the solvent fraction from Step G and the liquid is evaporated.

While 90/10 ethanol/water is specified in the procedure above, one skilled in the art based on the teachings herein will recognize that a broad range of alcohol/water combinations can be use, including up to 100% alcohol or even less than 10% alcohol, and other alcohols including but not limited to methanol, iso-propanol, butanol, etc., as well as chemically modified alcohols commonly used in solvent extraction procedures can be used. Still further, combinations of alcohols and other alcohol compatible solvents can be used in place of water. By varying the composition of the alcohol extractant solution (varying concentrations or using different alcohols), the composition of the resultant lipid end product can also be tailored based on the solubility of each lipid constituent to obtain the desired phospholipids in the end product.

The dried soluble fraction may be reconstituted, for example using water, glycerin, pantethine or other suitable carrier, or combined with other suitable carriers or excipients such as, but not limited to disintegrants, binders, drug solubilizers, coatings, fillers, antioxidants, antiadherents, diluents, flavors, colors, lubricants, glidants, preservatives, sorbents, sweeteners, texturants, fragrances, etc., to place the resultant phospholipids into a usable form. One skilled in the art will recognize the numerous alternative suitable carriers or excipients. These include but are not limited to calcium stearate, crospovidone (PVP), dicalcium phosphate (DCP), hydroxypropyl cellulose, hydroxypropyl methyl cellulose (HPMC), magnesium stearate, maltodextrin, MCC (microcrystalline cellulose), polyethylene glycol (PEG), silicon dioxide, sodium carboxymethyl cellulose (CMC), sodium croscarmellose (CMC-Na), sodium starch glycolate, waxy maize starch. The dried soluble fractions resulting from the process of FIG. 4 comprise the various new Lipid Formulations when lecithin, plant materials, particularly oil seed precursors, or other lipid containing raw materials are used as a starting material.

Suitable acids for use in the FIG. 4 process include, but are not limited to lipoic acid, piperic acid, Arrhenius acids, Bronsted acids, Lewis acids, monoprotic acids, polyprotic acids, weak acids, strong acids, mineral acids, sulfonic acids, carboxylic acids.

A second extraction process, shown schematically in FIG. 5, can be employed using biological feedstocks to produce different new compositions referred to as Cyanithins. In an embodiment of this extraction the steps, with reference to FIG. 5, are as follows:

a) Supply a suitable feedstock (algal, bacterial . . . ). (step A)

b) The feedstock is extracted using a non-polar, non-toxic solvent suitable for processing food derivatives, with hexane being a preferred solvent, at a sufficient temperature and for a sufficient time (approximately 30 min.-5 hours at room temperature to about 60° C.), to extract the soluble lipids and other soluble components from feed stock. (step B)

c) The extract-containing hexane solution is separated from the extracted feedstock using a centrifuge or the solid material is settled out or filtered from the liquid and the solid is discarded. (Step C)

d) The separated organic solution (hexane or other solvent with dissolved material (Step D) is exposed to a vacuum, nitrogen bubbling or other evaporative process to separate the solute which is an oil containing the lipids, the oil being free of the organic solvent. (Step E)

e) The oil is de-gummed by adding a small amount of water to the oil (Step F), mixing the water with the oil phase and separating the "gum" that forms (step G).

f) The gum material is dried or lyophilized to produce phospholipids referred to as Cyanithin. (Step H)

Further refinement of the phospholipid component (Cyanithin) can then be made using the extraction protocol shown in FIG. 4.

The extraction procedure using non-polar solvent extraction to obtain a lipid extract, followed by de-gumming the solvent-free oil with a small amount of water to obtain the PL fraction (Cyanithins) can be applied to other feed stocks. Examples of various new feed stocks include plants, animals, single-celled organisms that are eukaryotes, single-celled organisms that are prokaryotes, including algae, and yeast or fungi. Targeted microorganisms may include Bacteria, including: *Aquifex, Thermotoga, Bacteroides, Cyophaga, Planctomyces, Cyanobacteria, Proteobacteria, Spirochetes*, Gram positives, Green Filamentous bacteria, *Pydrodicticum; Archea*, including: *Thermoproteus, T. celer, Methanococcus, Methanobacterium, Methanoscarcina,* Halophiles; Eucaryota including: *Entamoebae*, Slime molds, Animals, Fungi, Plants, Ciliates, Flagellates, Trichomonads, Microsporidia, and Diplomonads.

Further, the feed stocks can be selected for particular natural (or altered) lipid profiles to directly provide enriched new compositions or Cyanithins. For instance, species such as micro-algae that contain phosphatidylglycerol may be selected as feedstock. Lipids that are sought in these microalgae species include the precursors to cardiolipin and phosphatidylglycerol and may include, phosphatidic acid, diacylglycerol, cytidine diphosphate diacylglycerol (CDP-DAG), glycerol-3-phosphate, 3-sn-phosophatidyl-1'-sn-glycerol 3'-phosphatidic acid, phosphatidylglycerol; complex lipoamino acids such as alanylphosphatidylglycerol and lysulphosphatidylglycerol, phosphatidylserine, phosphatidylthreonine; betaine lipids such as diacylglyceryltrimethylhomoserine, diacylglyceryl hydroxymethyltrimethyl-beta-alanine, and diacylglycerylcarboxyhydroxymethylcholine; lysophospholipids such as lysophosophatidylglycerol, lysobisphosphatidylglycerol, lysophosphotidylcholine, lysophosphatidylserine; glycophospholipids such as glycosyldiacylglycerols, phosphatidylglucose, sphingolipids.

In addition, the extracts obtained from these precursor feed stocks may be enriched with suitable fatty acids such as palmitic acid, linoleic acid, alpha-linolenic acid, fatty acids 16:0, 18:0, 18:1; n-3 (omega-3); positions sn-1 and sn-2; 18:2 (n-6). Other acyl chains may be selected depending on the deficiency in the organ or organism being extracted.

Still further, cultured or natural growing conditions may be manipulated by growing selected micro-algae under conditions that foster enrichment of phosphatidylglycerol or result in other the presence of other targeted lipids. For example, conditions that may be purposely manipulated include, but are not limited to adjusting light and dark cycles, adjusting temperature of the growth medium; varying nutrient factors such as manganese salts added to promote the metabolism of lipids, adjusting the pH of the growth medium; adjusting salinity of the growth medium; regulating or adjusting the concentration of the growing species and selecting a feedstock for adding to the growth culture all to enhance and maximize the production of phosphatidylglycerol or other targeted lipids.

Cyanithin from microorganisms is a new class of supplements that are intended for replacing the characteristic lipids found in tissue-specific mitochondrial membranes as well as tissue-specific cell membranes. The extraction and enrichment of lipids, particularly phospholipids, from micro-algae and other organisms offers a wide variety of phospholipids and glycophospholipids for treating specific human disorders. The phospholipid composition of different human organs varies considerably. Specifically designed phospholipid profiles of the New Lipid Formulations or Cyanithin, which can be enriched by addition of other compounds are preferred for restoring health for a variety of organ-specific treatments or disease conditions, as well as in halting or reversing the effects of aging and disease. FIG. 7 lists examples of specific organ or tissue phospholipid profiles. Table 21 lists examples of various formulations to address specific diseases or organs. Examples of specific diseases that can be treated with the new compositions alone or in combination with Cyanithins, are addressed below.

Cyanithins and/or the newly disclosed compositions can be tailored with specific phospholipid profiles for specific mitochondria or cell membrane therapies depending on the disease and the organ or tissue affected. On the other hand, the base extracts or Cyanithins (not adjusted for tissue specificity) can be used for example for general health, anti-aging, improvement in quality of life and general disease treatment.

Lecithin and Cyanithin Preparation, Extraction, and Purification Process

With reference to FIGS. 4 and 5, methods for processing various natural materials, for example, to enhance concentrations of phosphatidylglycerol, comprises preliminary preparation, extraction or concentration of a natural (biological) material, for example microalgae.

Examples of various materials that can be processed include, but are not limited to Bacteria, for example, *Aquifex, Thermotoga, Bacteroides, Cyophaga, Planctomyces, Cyanobacteria, Proteobacteria, Spirochetes*, Gram positives, green filamentous bacteria, *Pydrodicticum*; Archea, including *Thermoproteus, Thermococcus celer, Methanococcus, Methanobacterium, Methanoscarcina*, Halophiles; Eucaryota including: *Entamoebae*, Slime molds, Animals, Fungi, Plants, Ciliates, Flagellates, Trichomonads, Microsporidia, and Diplomonads. These microalgae are preferred because they produce or possess limited quantities of undesirable compounds.

Examples of targeted compounds are cardiolipin and precursors to cardiolipin and phosphatidylglycerol which include, but are not limited to, phosphatidic acid, diacylglycerol, cytidine diphosphate diacylglycerol (CDP-DAG), glycerol-3-phosphate, 3-sn-phosophatidyl-1'-sn-glycerol 3'-phosphatidic acid, phosphatidylglycerol; complex lipoamino acids such as alanylphosphatidylglycerol and lysulphosphatidylglycerol, phosphatidylserine, phosphatidylthreonine; betaine lipids such as diacylglyceryltrimethylhomoserine, diacylglyceryl hydroxymethyltrimethyl-beta-alanine, and diacylglycerylcarboxyhydroxymethylcholine; lysophospholipids such as lysophosophatidylglycerol, lysobisphosphatidylglycerol, lysophosphotidylcholine, lysophosphatidylserine; glycophospholipids such as glycosyldiacylglycerols, phosphatidylglucose, sphingolipids.

These precursors can include suitable fatty acids such as palmitic acid, linoleic acid, stearic acid, oleic acid, alpha-linolenic acid, fatty acids 16:0, 18:0, 18:1; n-3 (omega-3); positions sn-1 and sn-2; 18:2 (n-6).

As a first step, water is removed from the microalgae or other material. The dry material is then frozen at a temperature between 373° K and 0° K and maintained at a controlled pressure. Alternatively, the sample can be boiled between 273° K and 400° K at a selected.

Alternative processing can include filtering or centrifuging the sample to concentrate the sample and/or remove undesirable materials or fractions, solid and liquid phase, or organic and aqueous phases. As an alternative, it can be adequate for the fractions to separate into different layers caused by gravity or increased gravity.

Some of the undesirable compounds that may be found in less preferential micro-algae include microcystins, natural and exogenous toxins, toxic metals, harmful oxidants, organophosphates and other pesticides or fertilizers, and nucleic acids. However, the less desired micro-algae can be purified to reduce or remove these undesirable compounds for example by enhancing the concentration of desirable components in one phase. The separation of fractions into different phases or layers can be enhanced or caused by the addition of gaseous, liquid, or solid chemicals to the sample or subsequent phases or modifying separation conditions to decrease the concentration of undesirable components in one phase.

The species processed can be chosen specifically for its lipid profile to provide enriched target lipids for Cyanithin or new Lipid Formulations A, C, E, G, I, or S.

The concentration, extraction, and purification of microalgae, bacteria, single celled organisms, plants, plant extracts, animal tissues and animal extracts can provide concentrates of natural antioxidants, proteins, and beneficial biomolecules. In addition, certain biological pigments, can be recovered including, but not limited to chlorophyll-a, xanthophyll, beta-carotene, echinenone, myxoxanthophyll, zeaxanthin, canthaxanthin, diatoxanthin, 3'-hydroxyechinenone, beta-cryptoxanthin, oscillaxanthin, plus the phycobiliproteins c-phycocyanin and allophycocyanin.

concentrations of the various measured phospholipids recovered from the solids phase by hexane extraction. In a like manner row D shows the results of extraction of the liquid phase using an ethanol/glycerol solution and row E shows the concentrations in the solid phase after the ethanol/glycerol extraction. Rows F and G show the results for the liquid and solid phases following an ethanol/α-lipoic acid extraction.

TABLE 11

LECITHIN EXTRACTED WITH ETHANOL, GLYCERIN, AND LIPOIC ACID

| # | Sample | DGDG | MGDG | PG | L-PG | L-PC | L-PE | PC | PE | PI | PS | PA | Total nm/mgs |
|---|--------|------|------|-----|------|------|------|-----|-----|-----|-----|-----|------|
| A | Comm. lecithin | 37 | 2 | 15 | >1 | 6 | 4 | 200 | 120 | 158 | 3 | 88 | 633 |
| B | EtOHE | 23 | 2 | 12 | >1 | 5 | 3 | 164 | 77 | 46 | 1 | 35 | 369 |
| C | EtOHH | 8 | >1 | 4 | >1 | >1 | 2 | 43 | 52 | 134 | 3 | 55 | 301 |
| D | GlycE | 31 | 2 | 13 | >1 | 6 | 4 | 183 | 92 | 51 | 1 | 34 | 417 |
| E | GlycH | 12 | >1 | 5 | >1 | 1 | 2 | 53 | 72 | 159 | 3 | 71 | 377 |
| F | AlphaE | 12 | >1 | 5 | >1 | 2 | 1 | 86 | 38 | 8 | >1 | 11 | 164 |
| G | AlphaH | 2 | >1 | 1 | >1 | >1 | >1 | 9 | 27 | 84 | 2 | 38 | 165 |

Sample size was 0.100 to 0.102 mg. Variability is due to recovery efficiency of extraction and analysis. The important information obtained is not the quantity of each phospholipid; of importance is the ratio of phospholipids in each extraction.
A: a powdered lecithin containing a high level of natural, functional phospholipids from soybean lecithin
B: 90% EtOH extraction;
C: Hexane wash of solid phase from B;
D: 90% EtOH + 5% glycerol extraction;
E: Hexane wash of the solid phase from D
F: 90% EtOH + α-lipoic acid
G: Hexane wash of the solid phase from F The lipid, phospholipid and phytopigment as well as other beneficial biomolecule fractions obtained from the starting biological material, referred to as Cyanithin, are analogous to the lecithin fraction extracted from plants.

Three groups of experiments were performed to test various extraction procedures on lecithin (*Triticum* species) as well as two species of algae (*Spirulina* and *Chlorella*). The extractions were conducted to determine if there is any chemical reactivity during extractions with ethanol, ethanol with glycerin, and ethanol with alpha-lipoic acid when compared with a commercial lecithin starting material. The individual samples were then analyzed for total major species of phospholipids, including DGDG, MGDG, PG, LysoPG, LysoPC, LysoPE, PC, PE, PI, PS, and PA.

In each extraction, the 120 grams of the starting material was placed in a test tube with solvent. The test tube was placed in boiling water for ten minutes, followed by centrifuging at room temperature. The liquid extract was poured off and the residue was re-processed in alcohol, as in FIG. 4, or hexane followed as shown in FIG. 5, and the liquid extract was recovered.

Example 1

The starting material was a commercially available lecithin (*Triticum* species).

Table 11 below lists the quantity of the identified phospholipids. Row A lists the quantities, in mgs, of the measured phospholipids in the starting material. The starting material was boiled, cooled and the liquid phase separated from a solid residue. Rows B through G show the compositions of the starting material after extraction using various different solvent combinations. Row B lists the concentrations of the various measured phospholipids in the liquid phase obtained by ethanol extraction. Row C lists the Examination of the data indicates that some species are of lesser importance: The lyso-phospholipids, MGDG and PS do not individually represent more than 1% of any sample or extraction. Table 12 below lists the quantity in grams of only the major constituents. Table 13 lists the percent of the phospholipids in the liquid phase versus the solid phase. In the above Table 11 there is an extraction step missing for the α-lipoic acid extractions. See example 3 below for more comparable data on α-lipoic acid extraction characteristics.

TABLE 12

COMPOSITION OF DIFFERENT PHASES

| # | Sample | DGDG | PG | PC | PE | PI | PA | Total, nm/mg |
|---|--------|------|-----|-----|-----|-----|-----|------|
| A | Commercial lecithin | 37 | 15 | 200 | 120 | 158 | 88 | 633 |
| B | EtOHE | 23 | 12 | 164 | 77 | 46 | 35 | 369 |
| C | EtOHH | 8 | 4 | 43 | 52 | 134 | 55 | 301 |
| D | GlycE | 31 | 13 | 183 | 92 | 51 | 34 | 417 |
| E | GlycH | 12 | 5 | 53 | 72 | 159 | 71 | 377 |

DGDG is digalactosyldiacylglycerol.

TABLE 13

EFFICIENCY OF EXTRACTIONS (First extract versus total extract):

| # | Sample | DGDG | PG | PC | PE | PI | PA |
|---|--------|------|-----|-----|-----|-----|-----|
| A | Commercial lecithin | 37 | 15 | 200 | 120 | 158 | 88 |
| B | EtOHE | 74% | 75% | 79% | 60% | 26% | 39% |
| D | GlycE | 72% | 72% | 78% | 56% | 24% | 32% |

The ethanol extraction preferentially extracts PG and PC from the lecithin, the process is about 50-60% efficient at extracting PE, and only 25% efficient at extracting PI. Accordingly, ethanol extraction provides a composition with enhanced quantities of PG and PC, about the same concentration of PE while excluding PI. This is important because PE and PI are the $3^{rd}$ and $2^{nd}$ major constituents of the starting material behind PC which is the major constituent. Thus compositions with greater amounts of PG and PC can be obtained which do not include PI. On the other hand, PI becomes concentrated in the solid phase.

Table 14 sets forth the percentages of the various measured phospholipids in the starting material compared to the concentrations in the extracts. The total phospholipid extraction from the starting material using 95% ethanol extraction is 55% of the staring material while 90% ethanol plus 5% glycerin extracts 53%.

TABLE 14

PERCENT COMPOSITION OF ETHANOL EXTRACTED LECITHIN VERSUS UNEXTRACTED LECITHIN:

| # | Sample | DGDG | PG | PC | PE | PI | PA | Total, % |
|---|--------|------|----|----|----|----|----|----------|
| A | Commercial lecithin | 6% | 2% | 32% | 19% | 25% | 14% | 98% |
| B | EtOHE | 6% | 3% | 44% | 21% | 12% | 9% | 95% |
| C | EtOHH | 3% | 1% | 14% | 17% | 44% | 18% | 99% |
| D | GlycE | 7% | 3% | 44% | 22% | 12% | 8% | 96% |
| E | GlycH | 3% | 1% | 14% | 19% | 42% | 19% | 98% |

One skilled in the art will recognize that, based on the teachings herein, repetitive extractions can further enhance the amounts of soluble phospholipids while reducing the quantity of the less soluble phospholipids.

Example 2

The same procedure as described above was repeated with the same starting material (commercially available lecithin) but with different extraction liquids (or different concentrations).

Tables 15 and 16 list the quantities (grams) and percentages of the various phospholipids in each extraction.

TABLE 15

ETHANOL EXTRACTS OF LECITHIN AUGMENTED WITH GLYCERIN AND LIPOIC ACID

| # | Sample | DGDG | PG | L-PG-PC&PE | PC | PE | PI | PA | Total, nm/mg |
|---|--------|------|----|------------|-----|-----|-----|-----|--------------|
| 1A | EtOH | 13 | 12 | 9 | 160 | 64 | 28 | 25 | 311 |
| 2A | EtOH + αL | 14 | 12 | 9 | 168 | 78 | 26 | 27 | 335 |
| 3A | EtOH + Gl | 11 | 10 | 6 | 125 | 67 | 34 | 23 | 278 |
| 4A | Et + Gl + αL | 14 | 12 | 7 | 146 | 79 | 43 | 27 | 329 |
| 1B | EtOH | 9 | 5 | 3 | 43 | 80 | 156 | 58 | 357 |
| 2B | EtOH + αL | 8 | 4 | 3 | 47 | 74 | 142 | 58 | 340 |
| 3B | EtOH + Gl | 8 | 4 | 3 | 44 | 67 | 133 | 55 | 316 |
| 4B | Et + Gl + αL | 7 | 3 | 3 | 36 | 55 | 107 | 44 | 256 |

Sample List:
1A. 90% ethanol extraction
2A. 90% ethanol plus α-lipoic acid extraction
3A. 85% ethanol plus 5% glycerol extraction
4A. 85% ethanol plus α-lipoic acid plus 5% glycerol extraction
1B. Hexane extract of 1A-residual solids
2B. Hexane extract of 2A-residual solids
3B. Hexane extract of 3A-residual solids
4B. Hexane extract of 4A-residual solids

TABLE 16

PERCENT COMPOSITION OF ETHANOL, GLYCERIN AND LIPOIC ACID EXTRACTS

| # | Sample | DGDG | PG | L-PG-PC&PE | PC | PE | PI | PA | Total % |
|---|--------|------|----|------------|-----|-----|-----|-----|---------|
| 1A | EtOH | 4% | 4% | 3% | 51% | 21% | 9% | 8% | 100% |
| 2A | EtOH + αL | 4% | 4% | 3% | 50% | 23% | 8% | 8% | 100% |
| 3A | EtOH + Gl | 4% | 4% | 2% | 45% | 24% | 12% | 8% | 99% |
| 4A | Et + Gl + αL | 4% | 4% | 2% | 44% | 24% | 13% | 8% | 99% |
| 1B | EtOH | 3% | 1% | 1% | 12% | 22% | 44% | 16% | 99% |
| 2B | EtOH + αL | 2% | 1% | 1% | 14% | 22% | 42% | 17% | 99% |
| 3B | EtOH + Gl | 3% | 1% | 1% | 14% | 21% | 42% | 17% | 99% |
| 4B | Et + Gl + αL | 3% | 1% | 1% | 14% | 21% | 42% | 17% | 99% |

It was concluded that the extractions were affected by extraction constituents primarily to the extent that the addition of glycerol reduces the amount of PC that is extracted in the first step.

Experiment 3-Extractions of Three Different Lecithin Starting Materials

TABLE 17

| # | Sample | DGDG | PG | L-PG-PC&PE | PC | PE | PI | PA | Total, mgs |
|---|---|---|---|---|---|---|---|---|---|
| 1A | Lecithin 1 | 13 | 12 | 9 | 160 | 64 | 28 | 25 | 311 |
| 5A | Liquid Lecithin | 17 | 14 | 9 | 164 | 86 | 28 | 16 | 336 |

TABLE 17-continued

| # | Sample | DGDG | PG | L-PG-PC&PE | PC | PE | PI | PA | Total, mgs |
|---|---|---|---|---|---|---|---|---|---|
| 6A | Lecithin 3 | 12 | 10 | 5 | 121 | 57 | 32 | 21 | 261 |
| 1B | Lecithin 1 | 9 | 5 | 3 | 43 | 80 | 156 | 58 | 357 |
| 5B | Liquid Lecithin | 12 | 6 | 3 | 64 | 82 | 160 | 43 | 375 |
| 6B | Lecithin 3 | 4 | 1 | 1 | 14 | 27 | 98 | 22 | 170 |

TABLE 18

| # | Sample | DGDG | PG | L-PG-PC&PE | PC | PE | PI | PA | Total, % |
|---|---|---|---|---|---|---|---|---|---|
| 1A | Lecithin 1 | 4% | 4% | 3% | 51% | 21% | 9% | 8% | 100% |
| 5A | Liquid Lecithin | 5% | 4% | 3% | 49% | 26% | 8% | 5% | 100% |
| 6A | Lecithin 3 | 5% | 4% | 2% | 46% | 22% | 12% | 8% | 261 |
| 1B | Lecithin 1 | 3% | 1% | 1% | 12% | 22% | 44% | 16% | 99% |
| 5B | Liquid Lecithin | 3% | 2% | 1% | 17% | 22% | 43% | 11% | 99% |
| 6B | Lecithin 3 | 2% | >1% | >1% | 8% | 16% | 58% | 13% | 98% |

All extractions identified as 1A-9A show the liquid phase concentrations using 90% ethanol on a boiled starting material; the samples identified as 1B-9B show the concentrations in materials recovered from the residue solid phase from the ethanol extraction, by hexane extraction.

Based on the data in Tables 17 and 18 it was concluded the lecithin 1 granules have slightly less PC than lecithin 3. Otherwise the compositions are very similar. Liquid lecithin has a similar profile, but total phospholipids are much lower in the liquid lecithin.

Example 4

Extractions of *Chlorella, Spirulina*, and Lecithin 1 with *Spirulina* to Separate Cyanithins and Combinations

TABLE 19

Extractions of *Chlorella, Spirulina*, and Lecithin 1 with *Spirulina*

| # | Sample | DGDG | MGDG | PG | L-PG-PC&PE | PC | PE | PI | PA | Total, nm/mg |
|---|---|---|---|---|---|---|---|---|---|---|
| 7A | *Chlorella* | 41 | 166 | 13 | >1 | 11 | 4 | 2 | 1 | 240 |
| 8A | *Spirulina* | 4 | 22 | 8 | 1 | >1 | >1 | >1 | >1 | 35 |
| 9A | Alc + *Spiru* | 11 | 11 | 12 | 17 | 104 | 57 | 38 | 4 | 253 |
| 7B | *Chlorella* | 1 | 20 | >1 | >1 | >1 | >1 | >1 | 0 | 22 |
| 8B | *Spirulina* | >1 | 2 | >1 | >1 | >1 | 0 | 0 | 0 | 2 |
| 9B | Alc + *Spiru* | 4 | 2 | 1 | 1 | 12 | 11 | 48 | 38 | 117 |

*Chlorella* is a genus of single-celled green algae.
*Spirulina* is a microscopic blue-green algae.

TABLE 20

Extractions of *Chlorella, Spirulina*, and Lecithin 1 with *Spirulina*

| # | Sample | DGDG | MGDG | PG | L-PG-PC&PE | PC | PE | PI | PA | Total % |
|---|---|---|---|---|---|---|---|---|---|---|
| 7A | *Chlorella* | 17% | 69% | 5% | >1% | 5% | 2% | 1% | >1% | 99% |
| 8A | *Spirulina* | 11% | 63% | 23% | 3% | >1% | >1 | >1 | >1 | 100% |

TABLE 20-continued

Extractions of Chlorella, Spirulina, and Lecithin 1 with Spirulina

| # | Sample | DGDG | MGDG | PG | L-PG-PC&PE | PC | PE | PI | PA | Total % |
|---|--------|------|------|-----|------------|-----|-----|-----|-----|---------|
| 9A | Alc + Spiru | 4% | 4% | 5% | 7% | 41% | 23% | 15% | 2% | 97% |
| 7B | Chlorella | 5% | 91% | >1% | >1% | >1% | >1% | >1% | 0 | 96% |
| 8B | Spirulina | >1% | ~100% | >1% | >1% | >1% | 0 | 0 | 0 | 100% |
| 9B | Alc + Spiru | 3% | 2% | 1% | 1% | 10% | 10% | 41% | 32% | 100% |

7A. Chlorella
8A. Spirulina
9A. Lecithin 1 plus Spirulina
7B. Chlorella
8B. Spirulina
9B. Lecithin 1 plus Spirulina Based on the data in Tables 19 and 20 it is concluded that Spirulina's predominant phospholipid is PG, but the total lipid content and the make-up of the lipid acyl groups suggest that Spirulina alone is a less preferred source of lipids. Further co-extracting Spirulina and Lecithin 1 did not evidence any lipid conversions.

Chlorella produced nearly 70% monogalatosyldiacylglyceride (MGDG) in the first extraction. This is of significance as it identifies another source for extraction and conversion to PG or PC. MGDG is the major lipid in plastids (Douce R, Joyard J. Biochemistry and function of the plastid envelope. Annu. Rev. Cell Biol., 6:173-216, 1990.) Plastids are responsible for photosynthesis, forming chloroplasts, chromoplasts, and leucoplasts (several forms of un-pigmented plastids). Plastids are similar to mitochondria in that they have their own DNA (circular, like mtDNA, with 75 to 250 kilobases). Eukaryotes like euglena endosymbiotically engulf green algae, using the photosynthetic apparatus encased in two membranes. MGDG is polar but not charged—it does not form bilayers and may be the most abundant polar lipid in nature (Gounaris K, Barber J. Monogalactosyldiacylglycerol: The most abundant polar lipid in nature. Trends in Biochemical Sciences, 8:10 378-381, 1983).

MGDG and DGDG both contain large amounts of linolenic acid (18:3n-3) and the specific trienoic acid (16:3n-3). In higher plants, linolenic acid is so prevalent that these plants are called "18:3" plants. In angiosperms, linolenic acid is concentrated in sn-1 and sn-2, and 16:3n-3 is absent. Glycolipids act as surfactants.

Further analysis of acyl group composition in the MGDG fraction shows that about 10% (17/166) is 34:5, while nearly 90% (138/166) is 34:4. In addition, DGDG is (29/42) 34:4 and (4/42) 34:5. The only other significant DGDG and MGDG are 36:4: (3.5/42) and (6/166), respectively.

The recovery of MGDG or the acyl groups associated with MGDG or DGDG in Chlorella demonstrate that the extraction of chlorella, and possibly Spirulina, as well as other algae can be valuable sources for extraction to recover the desired phospholipids and that plant or bacterial product with high percentages of the desired compounds can be isolated and extracted using the process set forth herein.

Monogalactosyldiacylglycerol containing two linolenic acid (18:3 n-3) acyl groups has been described in fruits of rose hips (Rosa canina) and was shown to be an anti-inflammatory agent (inhibition of cell migration). This may be directly related to the clinically observed anti-arthritis properties of rose hip herbal remedies (Larsen E et al., J Nat Prod 2003, 66, 994).

Other studies reported that galactosyl diglycerides from various sources have antitumor-promoting (Shirahashi H et al., Chem Pharm Bull, 44, p 1404, 1996), oxygen scavenging (Nakata K, J Biochem, 127, p 731, 2000), and virus neutralizing (Nakata K et al., J Biochem, 127, 191, 2000) activities. More recently, DGDG synthesized or isolated from Clinacanthus leaves from Thailand exhibited anti-herpes simplex virus activity (Janwitayanuchit W et al., Phytochemistry, 64, p 1253, 2003).

Further, specific Cyanithin and Combinations or New Lipid Formulations can be combined in many different formulations specifically tailored to address cellular, organ, or systemic diseases.

Still further, the specific Cyanithin and Combinations or New Lipid Formulations can be combined with one or more nutrients, growth factors, or product formulations to synergistically generated health benefits and to enhance their health effect, or to enhance their bioavailability or enhance their solubility. The effects of adding the Compositions, Cyanithins or New Lipid Formulations to other formulations can increase the individual cellular and subcellular capability to absorb nutrients; match the lipid profile of healthy targeted organs; combine phospholipid fractions of known type and acyl groups to match the lipid profile of healthy targeted organs; and provide the specific lipids for treating membranes of organisms, organs, cells, and subcellular components.

Probiotics can also be added to a formulation to enhance the absorption of nutrients through the intestinal wall.

The prior NT Factor or New Lipid Formulations, Cyanithins and Combinations can be used alone or in combination for delivery using the new chewable wafer composition. All of the above described compositions, previously available for delivery only in a liquid of gel composition, and the nutritional and medicinal benefits previously described, can now be provided in a convenient chewable composition as described herein below.

The prior NT Factors, New Lipid Formulations or Cyanithins, alone or in combination, can be used in the chewable wafers. The amount of New Lipid Formulations, Cyanithins, and Combinations in the food product is preferably from at least 0.1 g/kg to 1000 g/kg.

The New Lipid Formulations, Cyanithins and Combinations alone or in combination, specifically formulated to address the phospholipids deficiencies or imbalances of various diseases may now be delivered in an edible wafer to treat the following diseases (provided as examples and not to limit the scope of the invention):

Mitochondrial dysfunction diseases: Huntington disease, Kearns-Sayre syndrome, Leigh syndrome, Leber's hereditary optic neuropathy (LHON), migraine and encephalopathy, mental retardation, myoneurogenic gastrointestinal encephalopathy (MNGIE), neuropathy, ataxia, retinitis pigmentosa, and ptosis (NARP); neuropathy, obesity, myoclonus epilepsy with ragged-red fibers, Parkinson's disease, stroke, subacute sclerosing encephalopathy, Wolff-Parkinson-White syndrome. Adult onset Alexander disease, GFAP, NDUFV1, Alpers-Huttenlocher disease, Alzheimer/Parkinsonism—amino acid disorders, nuclear mutations; amyotrophic lateral sclerosis (ALS), anemia, ataxias, Barth: Tafazzins; Xp28, cardiomyopathy, carnitine disorders, Cartilage-Hair hypoplasia. CNS: Infantile & Childhood onset Syndromes: congenital muscular dystrophy—nuclear mutation, cramps, deafness; Maternal (mtDNA): Point mutations—Syndromic (HAM; MELAS; MERRF): tRNA; —Non-syndromic & amino-glycoside induced: 12s rRNA; Nuclear mutations: DIDMOAD: WFS1; 4p16, deafness-dystonia: DDP protein; Xq22, diabetes, diabetes mellitus and deafness (DAD); dystonia, encephalopathies. Eye: blindness, gyrate atrophy, LHON, optic atrophy, Wolfram, WFS1, 4p16; WFS2, 4q22; ophthalmoplegia, external (PEO); Dominant: Multiple mtDNA deletions; Maternal: mtDNA point mutations; Recessive: mtDNA depletion; Multiple mtDNA deletions; Sporadic: Single mtDNA deletion; Immune (HyperThyroid); Fatigue & Exercise intolerance: fatal infantile myopathy with severe mtDNA depletion; Finnish neonatal metabolic syndrome (GRACILE); Friedreich ataxia: Frataxin 9q13; functional defects, gastrointestinal, HAM: mtDNA tRNA Ser; Huntington's chorea, hypoglycemia, Infantile CNS: mtDNA & Nuclear mutations, Kearns-Sayre; Single mtDNA deletion: Leber's optic neuropathy, (LHON); mtDNA: MTND genes, Leigh's syndrome; mtDNA & Nuclear mutations: Leukodystrophy. Longevity: maple syrup urine disease, MELAS: mtRNA Leu+other, Menkes: ATPase 7a; Xq12, MERRF: mtRNA Lys & Ser, MILS, MNGIE: Thymidine phosphorylase; 22q13, multiple symmetric lipomatosis: mtRNA Lys & nuclear; myalgias, myoglobinuria, myopathy syndromes, Infantile myopathies, Fatal: mtDNA depletion, "Later-onset": mtDNA depletion, inflammatory myopathy, inclusion body myositis: Mpl mtDNA deletions, mtDNA depletion: "Later-onset;" PM+COX-muscle fibers: Mpl mtDNA deletions, NARP/MILS: mt ATPase6, neoplasms, neuropathy syndromes, CMT 2A2: MFN2; 1p36, CMT 2K: GDA P1; 8q21, CMT 4A: GDA P1; 8q21, sensory neuropathy: recessive; sporadic, occipital horn syndrome: ATPase 7a; Xq12, Pancreas, paraganglioma, PGL1: SDH Subunit D; 11q23, PGL3: SDH Subunit C; 1q21, PGL+Pheochromocytoma: SDH Subunit B; 1p36, Parkinson's, Pearson's: mtDNA deletion, rhabdomyolysis: mtDNA, Selenium deficiency, Spastic paraparesis, SPG7: Paraplegin; 16q24, SPG13: HSPD1; 2q24, SPG31: REEP1; 2p12, HHH: Ornithine transporter; 13q14, spinal muscular atrophy: TK2; 16q22, Stuve-Wiedemann syndrome: 1p34, Sudden infant death (SIDS): mtDNA tRNA Leu. Systemic disorders: Toxic: AZT (Zidovudine), copper, germanium, trichloroethylene, Valproate: precipitates seizures in MELAS, Wilson's disease: ATPase 7B; 13q14.

Diseases affecting the heart and cardiovascular system: Arrhythmias: atrial fibrillation, heart block including first-degree AV block, second-degree AV block, and complete AV block; premature atrial complex (PAC), atrial flutter, paroxysmal supraventricular tachycardia (PSVT), Wolff-Parkinson-White syndrome, premature ventricular complex (PVC), ventricular tachycardia, ventricular fibrillation, long QT syndrome. Cardiomyopathies: dilated cardiomyopathy, hypertrophic cardiomyopathy, restrictive cardiomyopathy. Angina: angina pectoris, stable angina, unstable angina, variant angina (Pinzmetal's angina). Heart valve diseases: mitral stenosis, mitral valve regurgitation, mitral valve prolapse, aortic stenosis, aortic regurgitation, tricuspid stenosis, tricuspid regurgitation. Other heart diseases: myocarditis, rheumatic heart disease, pericarditis, syncope, cardiac tumors such as myxoma. Vascular diseases: aortic aneurysm, aortitis, artiosclerosis including arteriosclerosis obliterans, atherosclerosis, aortic dissection, high blood pressure including essential hypertension, secondary hypertension and malignant hypertension; stroke, transient ischemic attack, arterial embolism, acute arterial occlusion, Raynaud's phenomenon, arteriovenous fistula, vasculitis, thoracic outlet syndrome, venous thrombosis, deep vein thrombosis, thrombophlebitis, varicose veins, spider veins, lymphedema.

Diseases affecting the brain: abcess, adenoma, agensis of corpus callosum, alzheimers, anencephaly, aneurysm, anoxia, Arnold Chiari Malformation, astocytoma, atrophy, colloid cyst, contusion, edema, encephalocele, ependymoma, glioblastoma, Hemangioblastoma; hemmorrhage, intrventricular, germinal plate, intracerebral, petechial; holoprosencephaly, hydranencephaly, hydrocephalus, immature fetal brain, cerebral infarct, subacute infarct, middle cerebral artery infarct, hemmorhagic infarct, cystic cerebellar infarcts, infarcts of the cerebral hemispheres, Lewey body, lissencephaly, lymphoma, meningioma, meningitis, meningitis and IVH, metachromatic leukodystrophy, metastatic carcinomas, multiple sclerosis, oligodendroglioma, polymicrogyria, porencephalic cyst, toxoplasma encephalitis, toxoplasma infection, tuberous sclerosis.

Diseases affecting the lungs include: Acute bronchitis, Acute Respiratory Distress Syndrome (ARDS), asbestosis, asthma, bronchiectasis, bronchiolitis, bronchopulmonary dysplasia, byssinosis, chronic bronchitis, coccidioidomycosis (Cocci), COPD, cystic fibrosis, emphysema, hantavirus pulmonary syndrome, histoplasmosis, human metapneumovirus, hypersensitivity pneumonitis, influenza, lung cancer, lymphangiomatosis, mesothelioma, nontuberculosis mycobacterium, pertussis, pneumoconiosis, pneumonia, primary ciliary dyskinesia, primary pulmonary hypertension, pulmonary arterial hypertension, pulmonary fibrosis, pulmonary vascular disease, respiratory syncytial virus, sarcoidosis, severe acute respiratory syndrome, silicosis, sleep apnea, sudden infant death syndrome, tuberculosis. (From: http://www.lungusa.org/lung-disease/list.html)

Diseases affecting the central nervous system: Broca aphasia, cerebello-olivary degeneration of Holmes, choroid plexus papilloma Kluver-Bucy syndrome, multiple sclerosis, locked-in syndrome, Parinaud syndrome, pituitary adenoma, Wallenberg syndrome, Weber syndrome, Wernicke aphasia, Wernicke-Korsakoff syndrome, Wilson's disease.

Diseases affecting the liver: Acetaminophen use, acute liver failure, alcoholic liver disease, alcoholic hepatitis, blood vessel disorders of the liver, Budd-Chiari syndrome, enlarged liver, fatty liver. Gilbert syndrome, jaundice, liver cysts, liver hemangioma, nonalcoholic steatohepatitis, portal hypertension, primary sclerosing cholangitis, Zellweger syndrome.

Diseases affecting the kidneys, prostate and urogenital tract: Acidosis, acquired cystic kidney disease, Alport syndrome, amyloidosis, analgesic nephropathy, anemia in kidney disease, autosomal dominant polycystic kidney disease, benign prostatic hyperplasia, chronic kidney disease, cystitis, cystocele, cysts, ectopic kidney, end-stage renal disease, enuresis, erectile dysfunction, focal segmental glomerulosclerosis, glomerar diseases, glomerulosclerosis, Goodpasture's syndrome, hematuria, hemodialysis, hemolytic uremic syndrome in children, Henoch-Schönlein purpura, hypertension, IgA nephropathy, impotence, incontinence, infection (bladder or kidney), interstitial cystitis, kidney cysts, kidney dysplasia, kidney failure, kidney transplantation, lupus nephritis, medullary sponge kidney, membranous nephropathy, mineral and bone disorder of chronic kidney disease, nephrotic syndrome in adults, nephrotic syndrome in children, nerve disease and bladder control, neurogenic bladder, nocturnal enuresis, painful bladder syndrome, peritoneal dialysis, pessary, Peyronie's disease, prostatitis, proteinuria, pyelonephritis, renal artery stenosis, renal cysts, renal osteodystrophy, renal tubularar acidosis, stress incontinence, transplantation, urinary tract infections, urostomy, continent urinary diversion, vesicoureteral reflux.

While there is published literature specifically describing mitochondrial dysfunction, it is believed that additional evidence will be published showing that many of the diseases listed above not presently indicated as mitochondrial dysfunction can also be considered to involve mitochondrial dysfunction and can be treated as such. Upon determination of the phospholipids deficiencies in each, based on the teachings herein, compositions containing the missing or deficient compounds can be prepared and administered as set forth herein to address those deficiencies as a treatment for the disease or malfunction.

In summary, but without limiting the scope of the inventions set forth herein, described herein are a broad range of plant and biological feed sources which contain phospholipids or phospholipids precursors. Processes have been described to extract and recover these lipids, particularly phospholipids or phospholipids precursors, from the various feed sources and to prepare tailored compositions having ratios and quantities of specific lipids, phospholipids or phospholipids precursors for delivery to patients to establish, maintain adjust or restore cell and mitochondrial health in the human body, or a specific organ system within the human body, or for treating a specific disease or phospholipid deficiency within human body.

As an example, new formulations comprising phospholipids obtained from plant and biological materials, referred to herein as New Lipid Formulations and Cyanithins, can be used to prepare formulations, such as listed in Table 21, for addressing organ specific requirements, these formulations included in the wafers as described below. These compositions can be used to maintain organ heath or to reestablish organ heath. Based on specific individual organ chemistry, obtained by diagnostic techniques, blood tests and cell analysis, these formulations can be further varied to enhance specific individual phospholipid deficiencies.

TABLE 21

| ORGAN SPECIFIC PHOSPHOLIPID COMPOSITIONS, %,* | | | | |
| --- | --- | --- | --- | --- |
| Treatment for: | New Lipid Formulation C or Cyanithin C | New Lipid Formulation G or Cyanithin G & others | New Lipid Formulation E or Cyanithin E | New Lipid Formulation S or Cyanithin S |
| Brain-grey | 39 | 8 | 40 | 13 |
| Brain-white | 31 | 37 | 16 | 16 |
| Heart | 40 | 31 | 26 | 3 |
| Lungs | 53 | 20 | 19 | 8 |
| Liver | 44 | 25 | 28 | 3 |
| Kidneys | 33 | 42 | 24 | 1 |
| Skeletal muscle | 48 | 23 | 26 | 3 |

TABLE 21-continued

| ORGAN SPECIFIC PHOSPHOLIPID COMPOSITIONS, %,* | | | | |
| --- | --- | --- | --- | --- |
| Treatment for: | New Lipid Formulation C or Cyanithin C | New Lipid Formulation G or Cyanithin G & others | New Lipid Formulation E or Cyanithin E | New Lipid Formulation S or Cyanithin S |
| Plasma | 70 | 27 | 3 | — |
| Platelets | 40 | 23 | 28 | 9 |

*These concentrations are guidelines and may constitute midpoints of a range, for example ±2%, or the top or bottom of a range, depending on the specific organ.

Table 21 provides standard compositions designed to duplicate normal compositions in the organs listed therein and maintain normal function of the specified body organs. Variations (increases) in the quantities of the specific phospholipid in each composition are then provided based on identified deficiencies, leading to an increase in the percentage of a particular phospholipid in the composition provided by specific New Lipid Formulations or Cyanithins. For instance, for heart mitochondria, PG is present as cardiolipin at approximately 50%. In aged mitochondria, the acyl chains of the PG are replaced with primarily arachidonic acid and docosahexadecaenoic acid. PG, PG precursors or acyl chains (linoleic acid) are therefore provided in excess of the "normal" ratio of phospholipids or acyl groups to compensate for any deficiencies. From about 1% to about 5% phosphatidylinositol (PI) can also be included. Alternatively, the deficient species may be provided as a sole treatment. In a like manner, compositions are provided to address deficiencies or imbalances in the body or one or more organ systems as a result of a disease, for example diabetes, which has systemic consequences and can cause multiple and different organ lipid deficiencies.

Identified herein are various phospholipids which are essential for normal health and normal cell function or are present in properly functioning body organs. Also shown herein are methods for generating and isolating these phospholipids or combinations of phospholipids from plant and biological sources. Still further, described herein chewable wafers for delivery of intended combinations of phospholipids for maintaining or restoring health, treating diseases or addressing mitochondrial dysfunction. These combination of phospholipids can be delivered as standardized composition tailored to provide a desired effect (i.e., weight loss, fatigue, cognitive improvement, etc.) or to address specific diseases. Alternatively, the phospholipids can specifically compounded to address specific individual deficiencies identified by blood tests, cell analysis, or other diagnostic procedures performed on the individual to be treated.

Accordingly, in a first embodiment, compositions are disclosed which are designed, when delivered in clinically effective amounts in chewable wafers, for maintaining cell and mitochondrial health. These compositions comprise a mixture of phospholipids or phospholipids precursors, wherein the ratio of the specific phospholipids in the mixture added to the wafer components generally corresponds to the ratio of said phospholipids in the body of a healthy individual or are intended to produce a healthy phospholipid balance in the body.

In a second embodiment, compositions are disclosed for restoring cell and mitochondrial health, these compositions comprising a mixture of phospholipids or phospholipid precursors, in the wafer, the quantity and selection of phospholipids or phospholipid precursors therein being chosen to restore the normal balance and improve tissues and organs of the body exhibiting deficits of phospholipids.

In a third embodiment, compositions for inclusion in the wafers are disclosed for maintaining cell and mitochondrial health of a specific organ system, for instance the heart, brain, liver, lungs, skeletal muscles, etc., within the human body, the compositions comprising mixtures of phospholipids or phospholipid precursors. The ratio of the specific phospholipids or precursors thereof in the mixture generally corresponds to the ratio of said phospholipids in that organ system of a healthy individual and provide long-term maintenance of healthy membrane phospholipid levels/content within tissues and organs in the body.

In a fourth embodiment, compositions are disclosed for restoring cell and mitochondrial health to a specific organ system within the human body comprising a mixture of phospholipids or phospholipids precursors, the quantity and selection of phospholipids or phospholipids precursors in the wafer being chosen to restore the normal balance of phospholipids within that organ system of the human body including enhanced quantities of individual phospholipids or phospholipid precursors to address specific deficiencies.

In a fifth embodiment, compositions are disclosed for treating a specific disease or specific phospholipid deficiency within the human body. In that instance the quantity of, or the ratio of, the specific phospholipids or phospholipids precursors in the mixture added to the wafer is chosen to restore the balance of phospholipids within the human body of an individual to a level equivalent to that of an individual not having the specific disease or deficiency or, if appropriate, to provide additional quantities to further enhance body functions and general wellbeing.

Thus, preparation and delivery of proper phospholipid combinations supports structure and function of cell membranes, provides fundamental components of cell membranes essential for proper growth, maturing and proper functioning of cells, influences membrane functions associated with membrane proteins to help correct imbalances and increases cell membrane fluidity. Other benefits of delivery of the compositions disclosed herein are to:
  repair cell membrane damage,
  repair mitochondrial membrane damage,
  increase mitochondrial function,
  reduce fatigue,
  promote systemic energy,
  sustain cellular energy levels,
  sustain long-lasting energy
  improve quality of life and nerve function
  support healthy structure and function of tissues, organs and systems within the body,
  support healthy cardiovascular function, improve digestive function, support healthy
  metabolism, help weight management, improve respiratory health, support immune function,
  promote mental clarity, mental focus, concentration,
  support healthy cognitive function and healthy nerve function,
  provide rapid feelings of increased energy,
  provide anti-aging benefits by reducing mt dna deletions, and
  support cellular detoxification.

Detailed Description of Wafer Formulation

In a preferred embodiment the wafer product includes inulin, caffeine and a lipid composition, generally referred to herein as NT Factor Lipids. Several variations of NT Factor Lipids are described in U.S. patent application Ser. No. 13/208,255, incorporate herein in its entirety by reference but the lipids for inclusion in the wafers is not limited to the disclosed NT Factor Lipids. In addition, the wafers may include other nutrients in addition to or as substitutes for the lipids.

Figure 24:
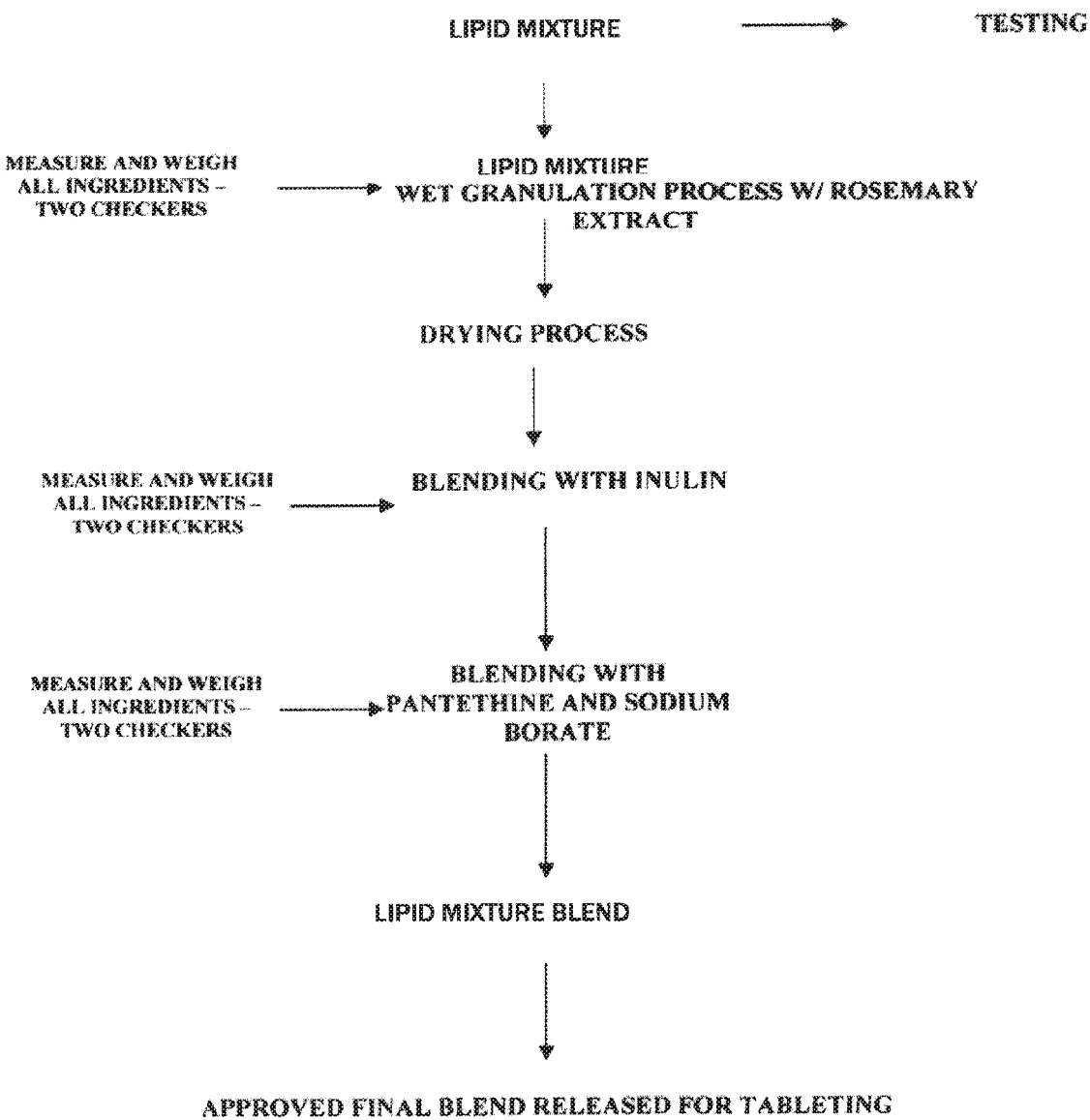
FIG. 24 is a schematic diagram illustrating the formation of a lipid blend for inclusion in a chewable wafer.
Figure 25:
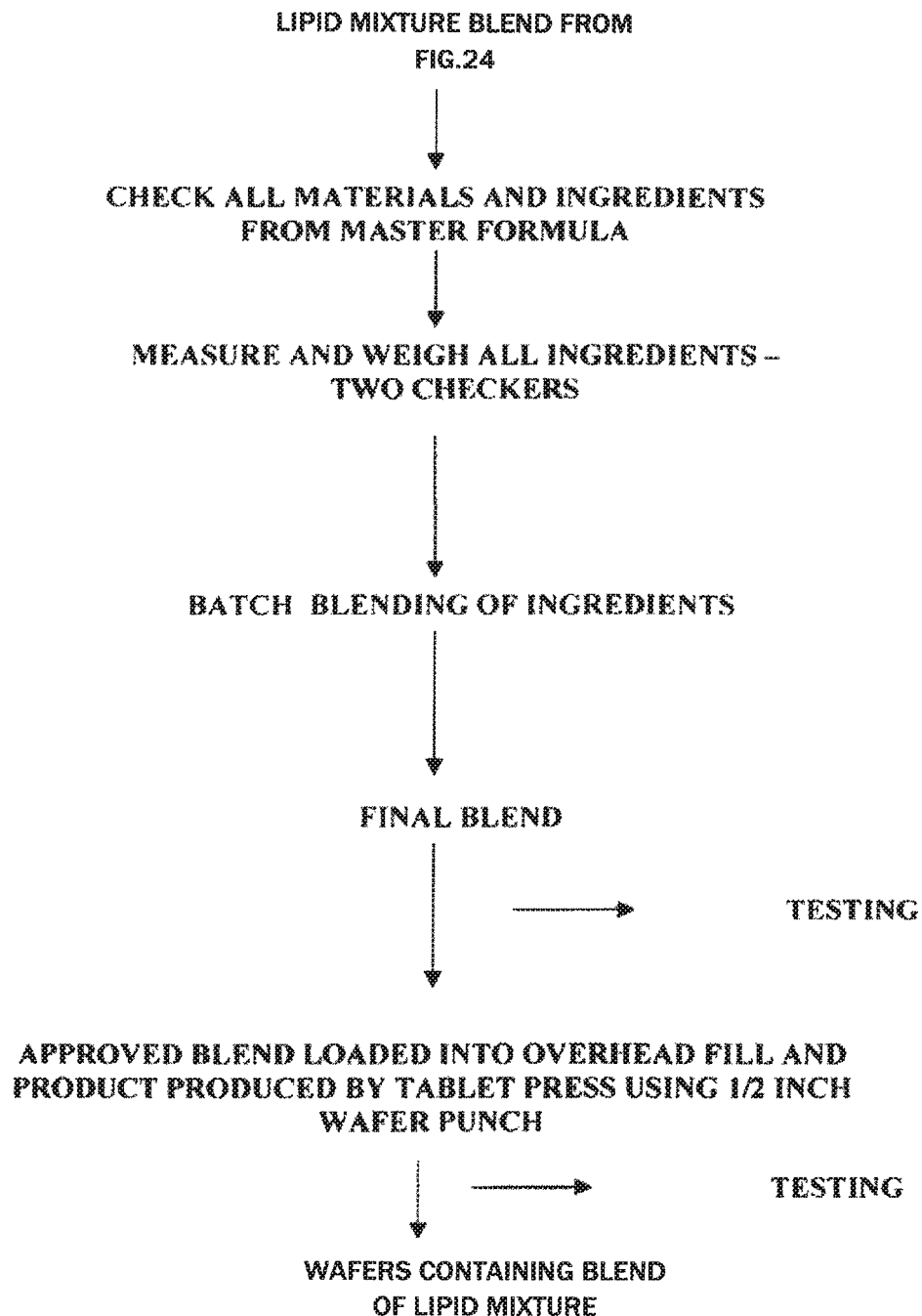
FIG. 25 shows the procedure for forming the chewable wafer from the lipid formulation provided by the procedure of FIG. 24.

Referring to FIG. 24, the lipid components of the NT Factor products are prepared by a wet granulation process which, in a preferred embodiment, includes coating with a rosemary extract to prevent lipid peroxidation. The resulting composition is then blended with inulin, which may be provided by extracts from artichoke, followed by blending with pantethine and sodium borate to form the base composition. The caffeine and any other ingredients for a particular therapeutic composition are then blended in to provide a final composition to be formed into a wafer.

Once the blending process is complete, the wafer can be formed using typical binding compounds, such as listed below as inactive ingredients or excipients, processing equipment and procedures standard in the industry for edible wafer manufacturing, which in some instances must be tailored to properly form wafers including the therapeutic composition. The powder blend of the therapeutic composition is fed into the feed hopper of a tableting machine by overhead fill, the powder is fed into the tableting machine for the formation of 6 mm thick, ½ inch wafers which are approximately 23 mm in diameter, the wafers are then packaged without being coated and then bottled in HDPE plastic bottles for distribution to retailers or customers. However, the wafer size is not critical and various different sized wafers may be provided. Also, the form of packaging, while preferred is not intended to limit the scope of the invention and other packaging techniques may be used.

In one preferred embodiment of the wafer useful for maintaining or restoring cell and mitochondrial health in an individual the phospholipid component of the composition comprises a mixture containing inulin and having about 19-29% phosphatidylcholine (PC), 15-25% phosphatidylethanolamine (PE), 3.5%-10% phosphatidic acid (PA), 10-18% phosphatidylinositol (PI), phosphatidylglycerol (PG) 2-10%, 10-20% glycolipids and 5-11% other phospholipids including phosphatidylserine (PS), and more particularly about 7% phosphatidic acid (PA), 5% phosphatidylglycerol (PG), about 24% phosphatidylcholine (PC), about 20% phosphatidylethanolamine (PE), about 14% phosphatidylinositol (PI), and less than about 8% phosphatidylserine (PS) or precursors for such phosphor lipids which are processed by the human body as the related phospholipids.

An embodiment for treating phospholipid deficiencies within the human cardiovascular system the phospholipid component of the wafer composition comprises a mixture containing inulin and having at least about 29% to about 33% phosphatidylglycerol (PG), at least about 38% to about 42% phosphatidylcholine (PC), at least about 24% to about 28% phosphatidylethanolamine (PE), and up to at least about 5% phosphatidylserine (PS) or precursors for PG, PC, PE or PS, and may alternatively include from about 1% to about 5% phosphatidylinositol (PI).

In an embodiment for treating phospholipid deficiencies within the human brain the phospholipid component of the wafer composition comprises a mixture containing inulin and having-least about 6% to about 39% phosphatidylglycerol (PG), at least about 29% to about 41% phosphatidylcholine (PC), at least about 14% to about 42% phosphatidylethanolamine (PE), and at least about 11%-18% phosphatidylserine (PS) or precursors for PG, PC, PE or PS, and from about 1% to about 5% phosphatidylinositol (PI).

In an embodiment for treating phospholipid deficiencies within the human respiratory system the phospholipid component of the wafer composition comprises a mixture containing inulin and having about 18% to about 22% phosphatidylglycerol (PG), at least about 51% to about 55% phosphatidylcholine (PC), at least about 17% to about 21% phosphatidylethanolamine (PE), at least about 6%-10% phosphatidylserine (PS) or precursors for PG, PC, PE or PS, and may alternatively include from about 1% to about 5% phosphatidylinositol (PI).

In an embodiment for treating phospholipid deficiencies within the human kidneys the phospholipid component of the wafer composition comprises a mixture containing inulin and having about 40% to about 44% phosphatidylglycerol (PG), at least about 31% to about 35% phosphatidylcholine (PC), at least about 22% to about 26% phosphatidylethanolamine (PE), at least about 3% phosphatidylserine (PS) or precursors for PG, PC, PE or PS, and may alternatively include from about 1% to about 5% phosphatidylinositol (PI).

In an embodiment for treating phospholipid deficiencies within the human skeletal system and muscles the phospholipid component of the wafer composition comprises a mixture containing inulin and having about 21% to about 25% phosphatidylglycerol (PG), at least about 46% to about 50% phosphatidylcholine (PC), at least about 24% to about 28% phosphatidylethanolamine (PE), and up to at least about 5% phosphatidylserine (PS) or precursors for PG, PC, PE or PS, and may alternatively include from about 1% to about 5% phosphatidylinositol (PI).

In an embodiment for treating phospholipid deficiencies in the plasma component of human blood the phospholipid component of the wafer composition comprises a mixture containing inulin and having about 25% to about 29% phosphatidylglycerol (PG), at least about 68% to about 72% phosphatidylcholine (PC) and at least up to about 5% phosphatidylethanolamine (PE), or precursors for PG, PC, PE or PS, and may alternatively include at least about 1% to about 5% phosphatidylinositol (PI) and phosphatidylserine (PS).

In an embodiment for treating phospholipid deficiencies in the platelet component of human blood the phospholipid component of the wafer composition comprises a mixture containing inulin and having about 21% to about 25% phosphatidylglycerol (PG), at least about 38% to about 42% phosphatidylcholine (PC), at least about 26% to about 30% phosphatidylethanolamine (PE), and at least about 7% to about 11% and at least about 1% to about 5% phosphatidylinositol (PI).

Composition 1

A phospholipid composition used as a starting materials is as follows:

TABLE 22

TYPICAL PHOSPHOLIPID PROFILE

| Species | % of Total | % of 18:2 Acyl Chains |
|---|---|---|
| Phosphatidylcholine (PC) | 31.62 | 11.61 |
| Phosphatidylinositol (PI) | 24.87 | 3.3 |
| Phosphatidyletanolamine (PE) | 18.86 | 6.86 |
| Phosphatadic Acid (PA) | 13.88 | 5.63 |
| Digalactosyldiacylglycerol (DGDG) | 5.88 | 1.23 |
| Phosphatidylglycerol (PG) | 2.37 | 0.275 |
| Lyso-Phosphatidylcholine (PC) | 0.982 | 0.614 |
| Lyso-Phosphatidyletanolamine (PE) | 0.698 | 0.35 |
| Phosphatidylserine (PS) | 0.472 | 0.067 |

TABLE 22-continued

TYPICAL PHOSPHOLIPID PROFILE

| Species | % of Total | % of 18:2 Acyl Chains |
|---|---|---|
| Monogalactosyldiacylglycerol (MGDG) | 0.311 | 0.149 |
| Lyso-Phosphatidylglycerol (PG) | 0.057 | 0.023 |

Sufficient rosemary extract is dissolved in an alcohol/citric acid solution and this solution is spray dried onto dry particles of the lipid composition to provide an even coating of the extract on the lipid particles. The coated lipid particles are then further dried at room temperature for about 24 hours and then blended with inulin, pantethine and sodium borate to provide the base composition. The base composition may also contain one or more of sodium, calcium, phosphorus, iron and potassium salts. In a preferred composition each wafer contains about 1069.8 mg of the lipid powder, 0.107 mg of rosemary extract, 153.4287 mg of inulin, 5.1250 mg of pantethine and 1.3558 mg of sodium borate, for a total weight of about 1250 mg.

In a preferred embodiment, to produce the wafer the inactive ingredients or excipients listed below are blended with the base composition so that the each wafer also contains:

Xylitol—1670.9 mg
Vegetable Stearic Acid—80 mg
Natural Mixed Berry Flavor—60 mg
Vegetable Stearate—40 mg
Beet Juice Powder—40 mg
Citric Acid—30 mg While the preferential wafer composition contains xylitol, stearic acid and stearate, beet juice powder, citric acid and a flavoring agent such as berry, one skilled in the art will recognize that other materials such as other flavoring agents, vitamins, or nutritional supplements can be added or customary substitutes therefor may be provided. Further, while the quantities of each set forth above provide a suitable solid chewable wafer for the specific lipid composition specified, it is recognized that these concentrations may vary and may have to be modified to provide a suitable end product which may be dependent on the lipids or other active ingredients included in the wafer. In recognition thereof, the wafer produced in accordance with Composition 1 is provided as an example of an acceptable end product and wafers compositions containing different combinations of active and inactive ingredients are then appropriately modified to provide a wafer end product having approximately the same consistency as far as taste, chewability and other characteristics exhibited by the product of Composition 1. for an average finished weight per wafer of 3152 mg. On a percent weight basis the final wafer contains:

Active Ingredients
Lipids—1,069.8 mg=33.94%
Inulin—153.4287 mg=4.87%
Pantethine—5.1250 mg=0.16%
Sodium Borate—1.3558 mg=0.04%
Inactive Ingredients or Excipients
Xylitol—1670.9 mg=53.01%
Vegetable Stearic Acid—80 mg=2.54%
Natural Mixed Berry Flavor—60 mg=1.90%
Vegetable Stearate—40 mg=1.27%
Beet Juice Powder—40 mg=1.27%

Citric Acid—30 mg=0.95%
Rosemary extract—1.25 mg=0.04%
Mixture of one or more of sodium, calcium, phosphorus, iron and potassium salts-20 mg=0.6%

While the example above uses lipids set forth in Composition 1, based on the teachings herein one skilled in the art can readily fabricate lipid containing wafers with any of the other lipid compositions set forth above or, for that matter, any other lipid combinations or nutritional substituents as may be prepared to address maintenance of proper nutritional and/or phospholipid balances in the body or organ systems thereof or to address known or diagnosed nutritional and/or phospholipid deficiencies in specific organs or disease related conditions. A preferred range of lipid components comprises about 19-29% phosphatidylcholine (PC), 15-25% phosphatidylethanolamine (PE), 3.5%-10% phosphatidic acid (PA), 10-18% phosphatidylinositol (PI), 2-10%, phosphatidylglycerol (PG), 2-10% glycolipids and phosphatidylserine (PS), identified in combination in the Examples below as "lipids". One particularly preferred additive to the above wafer composition is CoQ10. Further, in the alternative wafer compositions described below the Mixed Berry Flavor may be replaced by other additives and the various components of the base composition (the Active ingredients) and the carrier for the base composition may be varied. In the compositions below the quantities of the substituents in the carrier are not specified as they may be readily varied by one skilled in the art to provide a wafer composition of the proper consistency, taste and chewability.

Example 5—Chocolate Flavored Wafer with CoQ10

Coenzyme Q10 (CoQ10) is a substance found in every cell of the body. The body produces CoQ10 and the mitochondria in the cells utilize CoQ10 to produce energy more efficiently to aid in cell growth and maintenance. CoQ10 also functions as an antioxidant as well as help enzymes function to digest food and perform other body processes, as well as help protect the heart and skeletal muscles. It is claimed that CoQ10 is beneficial to prevent heart failure, cancer, muscular dystrophy, and periodontal disease as well as being potentially beneficial in preserving brain function, and fighting migraine headaches, mental diseases and preventing, treating or reducing neurodegenerative conditions such as Alzheimer and Parkinson. It is also said to boost energy and speed recovery from exercise. The following composition includes an effective amount of CoQ10 to provide at least some of these benefits.

Active Ingredients (Base Composition)
Lipids—900 mg containing Phosphorus (from phosphoglycolipids)—22 mg
Inulin—150 mg
CoQ10—100 mg
Boron (as Sodium Borate)—0.150 mg
Inactive Ingredients or Excipients (Carrier)
Xylitol
Cocoa powder and chocolate flavoring
Stearic Acid
Vegetable Stearate
Colorants
Silicon dioxide Example 6—Vitamin Additives for Improved Bone Health The combination of Vitamin K2 and Vitamin D is more effective in preventing bone loss than either nutrient alone. The following composition includes an effective amount of Vitamin K2 and Vitamin D to provide improved bone health.

Active Ingredients (Base Composition)
Lipids—1200 mg
Phosphorus (from phosphoglycolipids)—32 mg
Inulin—150 mg
Vitamin D3 (as cholecalciferol)—2500 IU
Vitamin K—45 mcg
Boron (as Sodium Borate)—0.150 mg
Inactive Ingredients or Excipients (Carrier)
Xylitol
One or more flavoring agents including vanilla flavoring
Stearic Acid
Vegetable Stearate
Silicon Dioxide Example 7—Carbohydrate Blocker Compositions containing extracts of white bean have been suggested as promoting weight loss by blocking the absorption of ingested carbohydrates, enhancing fat loss, reducing body mass index, promoting insulin sensitivity and aiding in maintaining healthy triglyceride levels. The following composition includes an effective amount of Phaseolamin extract to provide at least some of these benefits.

Active Ingredients (Base Composition)
Lipids—670 mg
Phosphorus (from phosphoglycolipids)—18 mg
Inulin—150 mg
Phaseolamin extract derived from white kidney bean (phaseous vulgaris)—400 mg
Boron (as Sodium Borate)—0.150 mg
Inactive Ingredients or Excipients (Carrier)
Xylitol
Orange and vanilla flavoring
Stearic Acid
Vegetable Stearate
Orange coloring
Citric acid
Silicon Dioxide Antioxidants in diet can reduce or eliminate the cell-damaging effects of free radicals; antioxidant supplements can act along with endogenous systems in the human body to address negative consequences of oxidative stress. The heart, lungs and the brain are particularly vulnerable to oxidative injury. Antioxidants have also been investigated as possible treatments for neurodegenerative diseases such as Alzheimer's disease, Parkinson's disease, and amyotrophic lateral sclerosis. There is evidence that certain vegetables and fruits and extracts from these vegetables and fruits can protect against a number of cancers and other diseases. Studies have shown that people who took regular antioxidants in fruits and vegetables seemed to have lesser incidence of these diseases. In addition, those who took fewer amounts of antioxidants, or had excessive exposure to pro-oxidants like cigarette smoking etc., had a higher risk of these disorders. The following compositions includes an effective amount of antioxidants to provide at least some of these benefits.

Example 8—Antioxidant Composition

Active Ingredients (Base Composition)
Lipids—785 mg
Phosphorus (from phosphoglycolipids)—21 mg
Inulin—150 mg
Vitamin C—100 mg Trans-reservatrol—25 mg
Freeze-dried Muskmelon (*Cucumis melo*) juice concentrate—10 mg containing Superoxide dismutase (SOD)—140 IU and catalase—0.02 IU.
Alpha Lipoic Acid—
CoQ10
Boron (as Sodium Borate)—0.150 mg
Inactive Ingredients or Excipients (Carrier)
Xylitol
One or more flavoring agents
Stearic Acid
Vegetable Stearate
Citric acid
Beet juice
Silicon dioxide Example 9—Vegetable Blend Active Ingredients (Base Composition)
Lipids—670 mg
Phosphorus (from phosphoglycolipids)—18 mg
Inulin—150 mg
Mixture of one or more of dried, powdered broccoli, broccoli sprouts, tomato, carrots, spinach, kale, brussel sprouts and onion or extracts thereof—350 mg
Boron (as Sodium Borate)—0.150 mg
Inactive Ingredients or Excipients (Carrier)
Xylitol-
Flavoring agents
Stearic Acid-
Vegetable Stearate
Citric acid
Beet juice
Silicon dioxide Example 10—Fruit Blend Active Ingredients (Base Composition)
Lipids—670 mg
Phosphorus (from phosphoglycolipids)—18 mg
Inulin—150 mg
Mixture of one or more of dried, powdered wild blueberry, cranberry, raspberry, raspberry seed, strawberry, prune, tart cherry, wild bilberry, grape and grape seed or extracts thereof—350 mg
Boron (as Sodium Borate)—0.150 mg
Inactive Ingredients or Excipients (Carrier)
Xylitol-
Flavoring agents
Stearic Acid-
Vegetable Stearate
Citric acid
Beet juice
Silicon dioxide Example 11—Vegetable and Fruit Blend Active Ingredients (Base Composition)
Lipids—670 mg
Phosphorus (from phosphoglycolipids)—18 mg
Inulin—150 mg
Mixture of one or more of dried, powdered broccoli, broccoli sprouts, tomato, carrots, spinach, kale, brussel sprouts and onion or extracts thereof—350 mg
Mixture of one or more of dried, powdered wild blueberry, cranberry, raspberry, raspberry seed, strawberry, prune, tart cherry, wild bilberry grape and grape seed or extracts thereof—350 mg—350 mg
Boron (as Sodium Borate)—0.150 mg
Inactive Ingredients or Excipients (Carrier)
Xylitol
Flavoring agents
Stearic Acid
Vegetable Stearate
Citric acid
Beet juice
Silicon dioxide Example 12—Caffeine Wafers Several different variation of a chewable wafer/tablet were prepared. Each wafer was ⅞" Diameter and had a total weight of about 3500 mg and included:
a) NT Factor Lipids®—(U.S. Pat. No. 8,877,239) Non-GMO Proprietary Blend—includes Inulin (150 mg) Soy Phosphoglycolipids, Fructo-oligosaccharides and Pantethine (a Coenzyme A precursor) (approximately 1200 mg) (NT Factor® and NT Factor Lipids® are registered trademarks of Nutritional Therapeutics, Inc.),
b) a Blend comprising 67 or 75 mg of Beadlet Caffeine, 50 or 100 mg of caffeine anhydrous powder, Green Tea Extract (as Green Tea extract (*Camellia sinensis*) (leaf) [standardized for 98% polyphenols (9.8 mg) and 45% Epigallocatechin-3-P-gallate (4.5 mg) containing 0.4 mg caffeine], and Yerba mate (as Yerba Mate extract (*Ilex paraguariensis*) from (leaves) [standardized for 8% caffeine (0.8 mg)]. (The total weight of the blend is approximately 137 mg containing 118.2 mg of caffeine (referred to as Lite) or 195 mg (8 hour wafer) with 176.2 mg caffeine), and
c) natural mixed berry, chocolate or mocha flavoring. The difference between the chocolate and mocha wafers was the addition of natural coffee flavoring in place of a portion of the chocolate flavoring in the wafer. (One skilled in the art will recognize that other flavoring agents or combinations thereof can be used.)

Example 12A: Low Dose Caffeine Wafers (Lite) (4 to 6 Hours)

Active Ingredients:
Lipids 1,069.8 mg
Inulin 153.4287 mg
Caffeine (total 118.2 mg)
  Beadlet Caffeine 67 mg
  Anhydrous Caffeine Powder—50 mg
  10 mg Green Tea Extract—(0.4 mg caffeine)
  10 mg Yerba Mate—(0.8 mg caffeine)
Pantethine 5.1250 mg
Sodium Borate—1.3558 mg
Inactive Ingredients or Excipients
Xylitol—1,805.25 mg
Mixed Berry or Cocoa Natural Flavor—136.788 mg
Vegetable Stearic Acid—80 mg
Vegetable Stearate—40 mg
Beet Juice Powder—40 mg
Citric Acid—30 mg
Rosemary Extract—1.25 mg
Optional (Nu Pareil spheres composed primarily of starch and sugar).

Example 12B: 8 Hour Caffeine Wafers—

Active Ingredients:
Lipids 1,069.8 mg

Inulin 153.4287 mg
Caffeine (total—176.2 mg)
  Anhydrous Caffeine Powder—100 mg
  Beadlet Caffeine 75 mg
  10 mg Green Tea Extract—(0.4 mg caffeine)
  10 mg Yerba Mate—(0.8 mg caffeine)
Pantethine 5.1250 mg
Sodium Borate-1.3558 mg
Inactive Ingredients or Excipients
Xylitol—1,777.25 mg
Mixed Berry, Cocoa (chocolate) or Coffee Natural Flavor—136.788 mg
Vegetable Stearic Acid—80 mg
Vegetable Stearate-40 mg
Dextrose—40 mg
Rosemary Extract—1.25 mg It typically takes 45 minutes for 99% of the caffeine ingested to be absorbed by the body and in humans the half-life for caffeine averages 4 to 6 hours which explains why the average strong cup of coffee or a 200 mg pill will lasts less than 6 hours.

Unexpectedly, it was found that the higher dose wafer, containing about 175 mg caffeine was approximately twice as effective as the over-the-counter 200 gm caffeine pill. The 175 mg wafer, irrespective of the flavoring agent showed an increased energy, alertness and focus lasting an average of 8 hours and, if the 2 moderate coffee drinkers and the 3 heavy drinkers with a demonstrated caffeine resistance are deleted from the analysis, the 175 mg wafer demonstrated a consistent efficacy of about 9.4 hours. Further, the Lite wafer, containing only 118 mg of caffeine appeared to have an efficacy equal to a 200 mg caffeine pill. It is believed that the

TABLE 23

| Patient | Chocolate or Berry Wafer | Did Wafer improve alertness? | Did wafer help you stay focused? | How long did you experience a higher level of energy, alertness and focus after taking? | How long did it take you to feel increased energy, alertness and focus?[3] | Please rate the taste and flavor of the wafers? |
|---|---|---|---|---|---|---|
| A F | Berry | Yes | Yes | 10 hours | 1 hour | FAIR |
| A R | Berry | Yes | Yes | 8 hours | 2 hours | Good |
| C D[1] | Chocolate | Yes | Yes | 6 hours | 1 hour | Good |
| C C | Chocolate | Yes | Yes | 10 hours | 45 minutes | Excellent |
| D F | Berry | Yes | Yes | 9 hours | 30 Minutes | Excellent |
| D P | Berry | Yes | YEs | 10 hours | 30 minutes | Good |
| E A[1] | Chocolate | Yes | Yes | 6 hours | 30 minutes | Chocolate Rocks |
| E H | Berry | Yes | Yes | 9 Hours | 15 minutes | Excellent |
| F N | Chocolate | Yes | Yes | 9 hours | 45 minutes | Excellent |
| G R | Berry | Yes | Yes | 8 hours | 15 minutes | Fair- Tastes bitter |
| J C | Berry | Yes | Yes | 10 hours | 15 minutes | Excellent |
| J D | Chocolate | Yes | Yes | 11 hours | 5 minutes | Excellent |
| K M | Chocolate | Yes | Yes | 10 hours | 15 minutes | Excellent |
| L C | Berry | Yes | YEs | 9 hours | 30 minutes | Good |
| M M[2] | | No | No | No noticeable change | No increased energy/alertness | Excellent |
| N F | Chocolate | Yes | Yes | 10 Hours | 30 Minutes | Excellent |
| O R | Chocolate | Yes | Yes | 10 hours | 15 minutes | Excellent |
| R O | Berry | Yes | Yes | 10 hours | 15 minutes | Excellent |
| P L | | Yes | Yes | 9 hours | 30 minutes | Good |
| P A | Berry | Yes | Yes | 8 hours | 30 Minutes | Excellent |
| R F | Chocolate | Yes | Yes | 10 hours | 10 minutes | Excellent |
| R M[2] | | Yes | No | Unsure | 1 hour | Good |
| T B[2] | Chocolate | Yes | Yes | 6 hours | 30 minutes | Good |
| Z L | Berry | Yes | Yes | 8 hours | 30 minutes | Good |
| TOTAL | | 96% | 92% | Range 6-11 Avg. 8.01 hr | Range 5-60 min Avg. 31.9 min. | |
| T S | Lite | Yes | Yes | 5 hours | 20 minutes | Excellent |
| J S | Lite | Yes | Yes | 4 hours | 15 minutes | Good |
| P W | Lite | yes | yes | 6 hours | 10 minutes | Excellent |

[1]Believed to be moderate coffee drinkers with built-up moderate tolerance to caffeine intake.
[2]Heavy coffee drinker. Positive response after increased caffeine dosage.
[3]Referred to as "efficacy".

One 8-ounce cup of brewed coffee contains from 65 to 120 milligrams of caffeine while a strong brew can contain up to 180 mg of caffeine. On the other hand, NoDoz® and Vivarin®, which are over the counter pills containing 200 mg caffeine, are advertised as restoring mental alertness or wakefulness when experiencing fatigue or drowsiness. While the effectiveness of a 200 mg dose or a cup of coffee will vary depending on the age, weight and caffeine tolerance of an individual, the time that it takes for a 200 mg dose of commercially available caffeine pills to begin taking affect and the time period the effect continues will vary. However, on average, it generally takes 10 to 30 minutes to begin to take effect and the effect lasts for about 3-5 hours.

significantly increased beneficial effect of the wafer compositions described herein is due to the synergistic combination of the caffeine with the NT factor lipids and inulin which provide enhanced cell membrane transport. While examples 12A and 12B and Table 23 demonstrate and utilize preferred compositions containing approximately 118 and 175 mg of caffeine it is contemplated that caffeine concentrations from 100 to 200 mg in a single wafer can be used.

Described above are examples of wafer compositions that can be formed. They are provided as suitable compositions for delivery of effective amounts of the active ingredients listed therein but are not intended as limitations on the scope of compositions. One skilled in the art will recognize, based on the descriptions and teachings herein that numerous alternative compositions which include the lipids and inulin can be formed and ingredients from one or more examples can be combined to form alternative lipid containing edible wafers. Preparation and delivery of proper phospholipid combinations not only supports structure and function of cell membranes, provides fundamental components of cell membranes essential for proper growth, maturing and proper functioning of cells, influences membrane functions associated with membrane proteins to help correct imbalances and Increases cell membrane fluidity, but also provides a more beneficial biological environment for delivering and transporting caffeine into the body as well as to the caffeine receptors in the brain so as to allow the caffeine to be more effective and the beneficial effects to last longer than prior art caffeine delivery mechanisms. Other benefits of delivery of the compositions disclosed herein are to:

repair cell membrane damage,
repair mitochondrial membrane damage,
increase mitochondrial function,
reduce fatigue,
promote systemic energy,
sustain cellular energy levels,
sustain long-lasting energy
improve quality of life and nerve function
support healthy structure and function of tissues, organs and systems within the body,
promote mental clarity, mental focus, concentration,
support healthy cognitive function and healthy nerve function,
provide rapid feelings of increased energy,
provide anti-aging benefits,
address damage due to oxidative free radicals,
aid in weight loss, and
support cellular detoxification.

The addition to the chewable wafer of caffeine in the quantities described expands the utility of the wafers so produced. The capability of delivering the desired caffeine, inuline and phospholipids, as well as other desirable nutritional constituents in a chewable wafer form allows individuals to consume desired supplements in a patient friendly form that beneficially aids in compliance with medically established protocols, while allowing the individual to remain alert, perform tasks in a more focused and energetic manner.

I claim:

1. An edible wafer comprising:
   a) a base composition comprising a combination of inulin, phospholipids and caffeine in therapeutically effective amounts, and
   b) a carrier for the base composition comprising xylitol, a flavoring agent, stearic acid and/or vegetable stearate, and optionally further comprising a colorant,
   said wafer effective, when consumed by an individual, to increase alertness and allow the individual to perform tasks in a more focused and energetic manner, wherein the phospholipids in the base composition comprise about 19-29% phosphatidylcholine (PC), 15-25% phosphatidylethanolamine (PE), 3.5%-10% phosphatidic acid (PA), 10-18% phosphatidylinositol (PI), 2-10% phosphatidylglycerol (PG), 10-20% glycolipids and phosphatidylserine (PS).

2. The wafer of claim 1 being about 0.875 inch in diameter, having a total weight of about 3500 mg and containing 100 to 200 mg of caffeine.

3. The wafer of claim 2 containing about 118 mg of caffeine providing increased alertness, focus and energy for 4-6 hours.

4. The wafer of claim 2 containing about 175 mg of caffeine providing increased alertness, focus and energy for 8-9.4 hours.

5. The wafer of claim 1, wherein the flavoring agent is chocolate, mocha or wild berry.

6. The wafer of claim 1 further including sodium borate as an active ingredient.

7. An edible wafer comprising:
   a) a base composition comprising a combination of inulin, phospholipids and about 100-200 mg of caffeine in therapeutically effective amounts, and
   b) a carrier for the base composition comprising xylitol, a flavoring agent, stearic acid and/or vegetable stearate and optionally further comprising a colorant,
   said wafer effective, when consumed by an individual, to increase alertness and allow the individual to perform tasks in a more focused and energetic manner for 4-9.4 hours, wherein the base composition comprises a combination of phospholipids comprising phosphatidylcholine, phosphatidylethanolamine, phosphatidic acid, phosphatidylinositol, phosphatidylglycerol, glycolipids and phosphatidylserine.

8. The wafer of claim 7 containing about 118 mg of caffeine providing increased alertness, focus and energy for 4-6 hours.

9. The wafer of claim 7 containing about 175 mg of caffeine providing increased alertness, focus and energy for 8-9.4 hours.

10. The wafer of claim 7 further including sodium borate as an active ingredient.

* * * * *